(12) United States Patent
Lynch et al.

(10) Patent No.: US 9,908,849 B2
(45) Date of Patent: Mar. 6, 2018

(54) IMIDAMIDE SPHINGOSINE KINASE INHIBITORS

(71) Applicant: University of Virginia Patent Foundation, Charlottesville, VA (US)

(72) Inventors: Kevin R. Lynch, Charlottesville, VA (US); Timothy L. Macdonald, Charlottesville, VA (US); Thomas P. Mathews, Charlottesville, VA (US); Andrew Kennedy, Charlottesville, VA (US); Yugesh Kharel, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 0 days.

(21) Appl. No.: 15/242,330

(22) Filed: Aug. 19, 2016

(65) Prior Publication Data

US 2017/0166525 A1    Jun. 15, 2017

Related U.S. Application Data

(63) Continuation of application No. 13/390,207, filed as application No. PCT/US2010/045660 on Aug. 16, 2010, now Pat. No. 9,421,177.

(60) Provisional application No. 61/233,963, filed on Aug. 14, 2009.

(51) Int. Cl.
| A61K 31/40 | (2006.01) |
| C07D 207/09 | (2006.01) |
| C07C 257/16 | (2006.01) |

(52) U.S. Cl.
CPC ............ *C07D 207/09* (2013.01); *A61K 31/40* (2013.01); *C07C 257/16* (2013.01); *C07C 2101/02* (2013.01); *C07C 2101/08* (2013.01); *C07C 2101/14* (2013.01); *C07C 2103/74* (2013.01)

(58) Field of Classification Search
CPC .............................. A61K 31/40; C07D 207/09
See application file for complete search history.

(56) References Cited

U.S. PATENT DOCUMENTS

| 7,338,961 B2 | 3/2008 | Smith et al. |
| 9,421,177 B2 | 8/2016 | Lynch et al. |
| 2006/0194802 A1 | 8/2006 | Abdellaoui et al. |
| 2007/0135523 A1 | 6/2007 | Makovec et al. |
| 2011/0106241 A1 | 5/2011 | Lynch et al. |
| 2012/0214858 A1 | 8/2012 | Lynch et al. |

FOREIGN PATENT DOCUMENTS

| WO | WO-2007039781 A2 | 4/2007 |
| WO | WO-2011020116 A1 | 2/2011 |

OTHER PUBLICATIONS

Foss et al. (Bioorg Med Chem. Aug. 15, 2009; 17(16): 6123-6136).*
Clemens et al. (Bioorg. Med. Chem. Lett. 13 (2003) 3401-3404).*
Hengst et al. (Bioorg. Med. Chem. Lett. 20 (2010) 7498-7502).*
Hale et al. (J. Med. Chem., 2004, 47, 6662-6665).*
Mathews et al. (J. Med. Chem. 2010, 53, 2766-2778).*
"U.S. Appl. No. 13/390,207, Advisory Action dated May 11, 2015", 3 pgs.
"U.S. Appl. No. 13/390,207, Advisory Action dated Jun. 16, 2014", 3 pgs.
"U.S. Appl. No. 13/390,207, Advisory Action dated Aug. 20, 2014", 3 pgs.
"U.S. Appl. No. 13/390,207, Final Office Action dated Mar. 6, 2015", 11 pgs.
"U.S. Appl. No. 13/390,207, Final Office Action dated Apr. 4, 2014", 10 pgs.
"U.S. Appl. No. 13/390,207, Non Final Office Action dated Sep. 11, 2014", 8 pgs.
"U.S. Appl. No. 13/390,207, Non Final Office Action dated Oct. 18, 2013", 10 pgs.
"U.S. Appl. No. 13/390,207, Notice of Allowance dated Apr. 11, 2016", 8 pgs.
"U.S. Appl. No. 13/390,207, Preliminary Amendment filed Feb. 13, 2012", 2 pgs.
"U.S. Appl. No. 13/390,207, Response filed Jan. 17, 2014 to Non Final Office Action dated Oct. 18, 2013", 12 pgs.
"U.S. Appl. No. 13/390,207, Response filed Feb. 10, 2015 to Non Final Office Action dated Sep. 11, 2014", 10 pgs.
"U.S. Appl. No. 13/390,207, Response filed May 1, 2015 to Final Office Action dated Mar. 6, 2015", 10 pgs.
"U.S. Appl. No. 13/390,207, Response filed Jun. 4, 2014 to Final Office Action dated Apr. 4, 2014", 10 pgs.
"U.S. Appl. No. 13/390,207, Response filed Aug. 4, 2014 to Advisory Action dated Jun. 16, 2014", 10 pgs.
"U.S. Appl. No. 13/390,207, Response filed Aug. 23, 2013 to Restriction Requirement dated May 23, 2013", 3 pgs.
"U.S. Appl. No. 13/390,207, Restriction Requirement dated May 23, 2013", 8 pgs.
"International Application Serial No. PCT/US2010/045660, International Search Report dated Jan. 5, 2011", 3 pgs.
"International Application Serial No. PCT/US2010/045660, Written Opinion dated Jan. 5, 2011", 4 pgs.
Bektas, Meryem, et al., "A sphingosine kinase inhibitor induces cell death in temozolomide resistant glioblastoma cells", Cancer Chemother Pharmacol. 2009 64(5) 1053-8, (Oct. 2009), 9 pgs.
Coward, Jesse, et al., "Safingol (L-threo-sphinganine) induces autophagy in solid tumor cells through inhibition of PKC and the PI3-kinase pathway", Autophagy 5:2; 2009, (Feb. 16, 2009), 184-193.

(Continued)

*Primary Examiner* — Robert Havlin
(74) *Attorney, Agent, or Firm* — Schwegman Lundberg & Woessner, P.A.

(57) ABSTRACT

Imidamide (amidine) analogs that can inhibit the activity of sphingosine kinase 1 and sphingosine kinase 2 (SphK1 & SphK2) are provided. The compounds can prevent angiogenesis in tumors.

5 Claims, 34 Drawing Sheets

(56) References Cited

OTHER PUBLICATIONS

French, Kevin J., "Antitumor Activity of Sphingosine Kinase Inhibitors", J Pharmacol Exp Ther. 2006 318(2), (2006), 596-603.

Jung, In Duk, et al., "Sphingosine kinase inhibitor suppresses a Th1 polarization via the inhibition of immunostimulatory activity in murine bone marrow-derived dendritic cells", International Immunology, vol. 19, No. 4, (Jan. 16, 2007), 411-426.

Jung, In Duk, et al., "Sphingosine kinase inhibitor suppresses dendritic cell migration by regulating chemokine receptor expression and impairing p38 mitogen-activated protein kinase", 2007 Blackwell Publishing Ltd,Immunology, 121,, (2007), 533-544.

Kubinyi, H., "3D QSAR in Drug Design: Ligand-Protein Interactions and Molecular Similarity", vol. 2-3, Springer, (1998), 6 pgs.

Lai, Wen-Qi, et al., "Anti-Inflammatory Effects of Sphingosine Kinase Modulation in Inflammatory Arthritis", Journal of Immunology,181(11), (2008), 8010-8017.

Lee, et al., "CAPLUS Abstract of: Korean Journal of Medicinal Chemistry", (1994), 1 pg.

Paugh, Steven W., et al., "Aselective sphingosine kinase 1 inhibitor integrates multiple molecular therapeutic targets in human leukemia", Blood, vol. 112, No. 4; 1382-1391, (Aug. 15, 2008), 11 pgs.

Ricci, Clara, et al., "In vitro anti-leukaemia activity of sphingosine kinase inhibitor", 2008 Blackwell Publishing Ltd, British Journal of Haematology, 144, 350-357, (Nov. 19, 2008), 8 pgs.

Teruaki, Nishiuma, et al., "Inhalation of sphingosine kinase inhibitor attenuates airway inflammation in asthmatic mouse model", Am J Physiol Lung Cell Mol Physiol 294:, (2008), L1085-L1093.

Wermuth, "The Practice of Medicinal Chemsitry, 2d ed", Ch. 9-10 provided, (2003), 768 pgs.

* cited by examiner

Fig. 1A
Synthesis of VPC95287
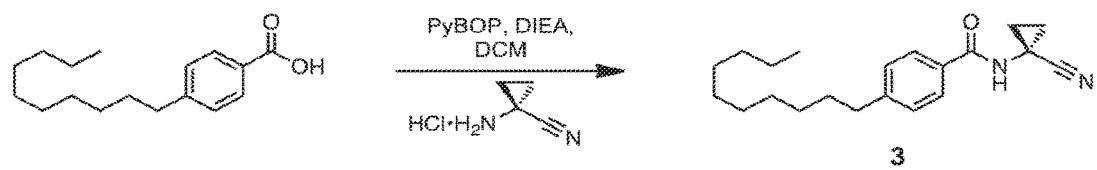
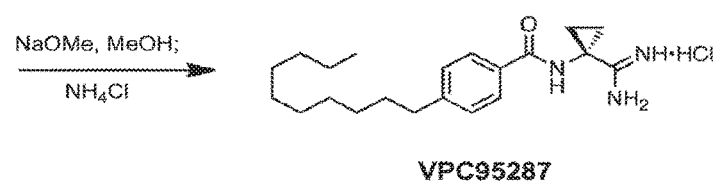
Fig. 1B
Synthesis of VPC95287
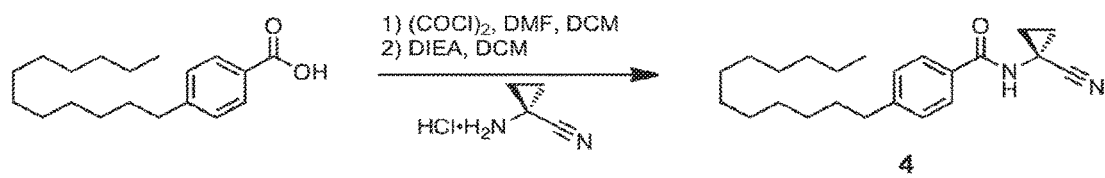
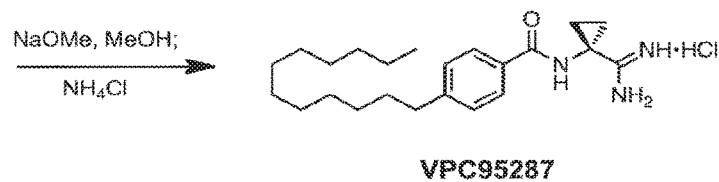

Synthesis of VPC171167

Synthesis of VPC95291

Synthesis of VPC95301

Synthesis of VPC143064

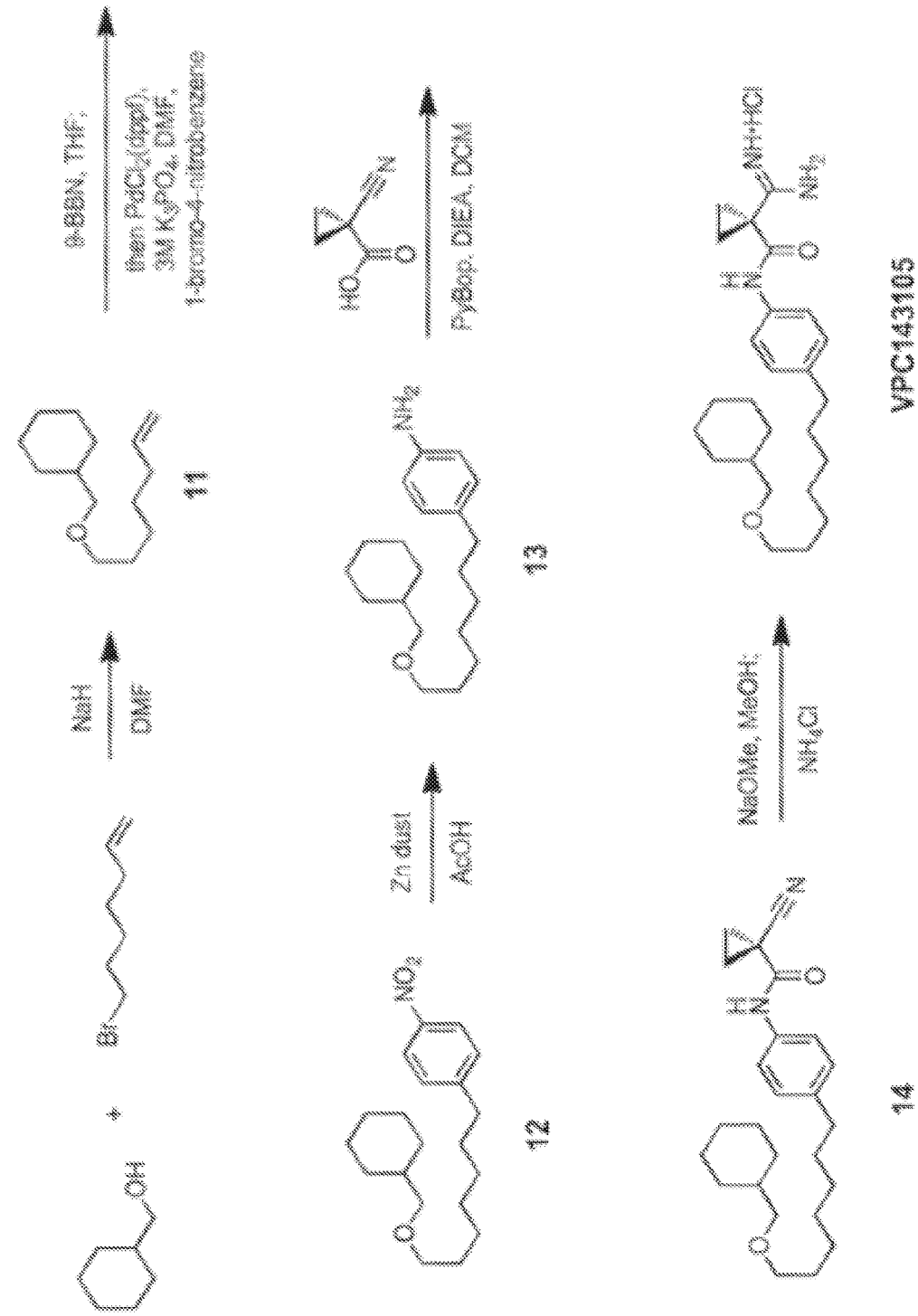
Fig. 1G Synthesis of VPC143105

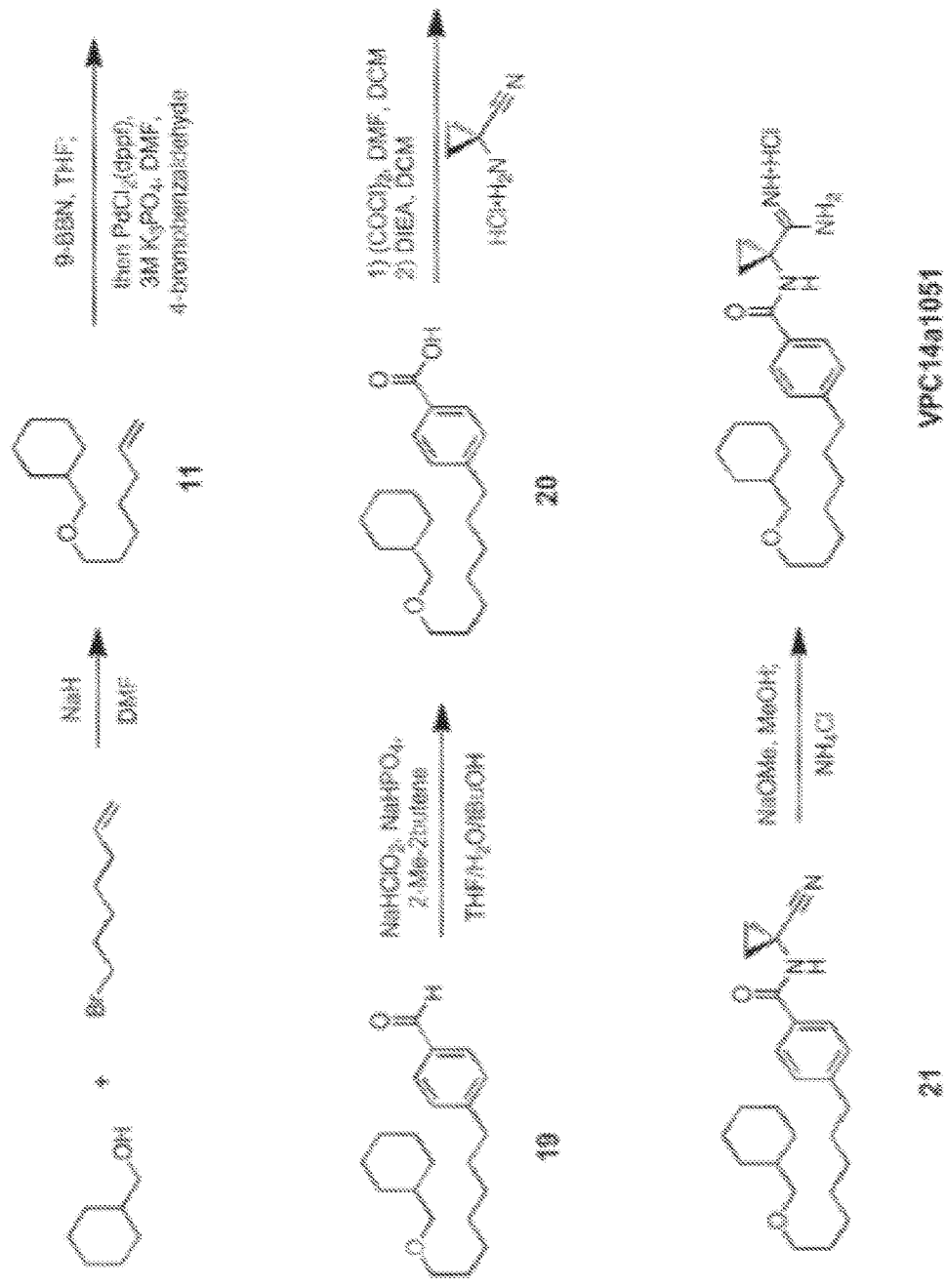

Synthesis of VPC143144

Synthesis of VPC143057

Synthesis of VPC96091

Synthesis of VPC95229

Synthesis of VPC96143

Synthesis of VPC143237

Synthesis of VPC96115

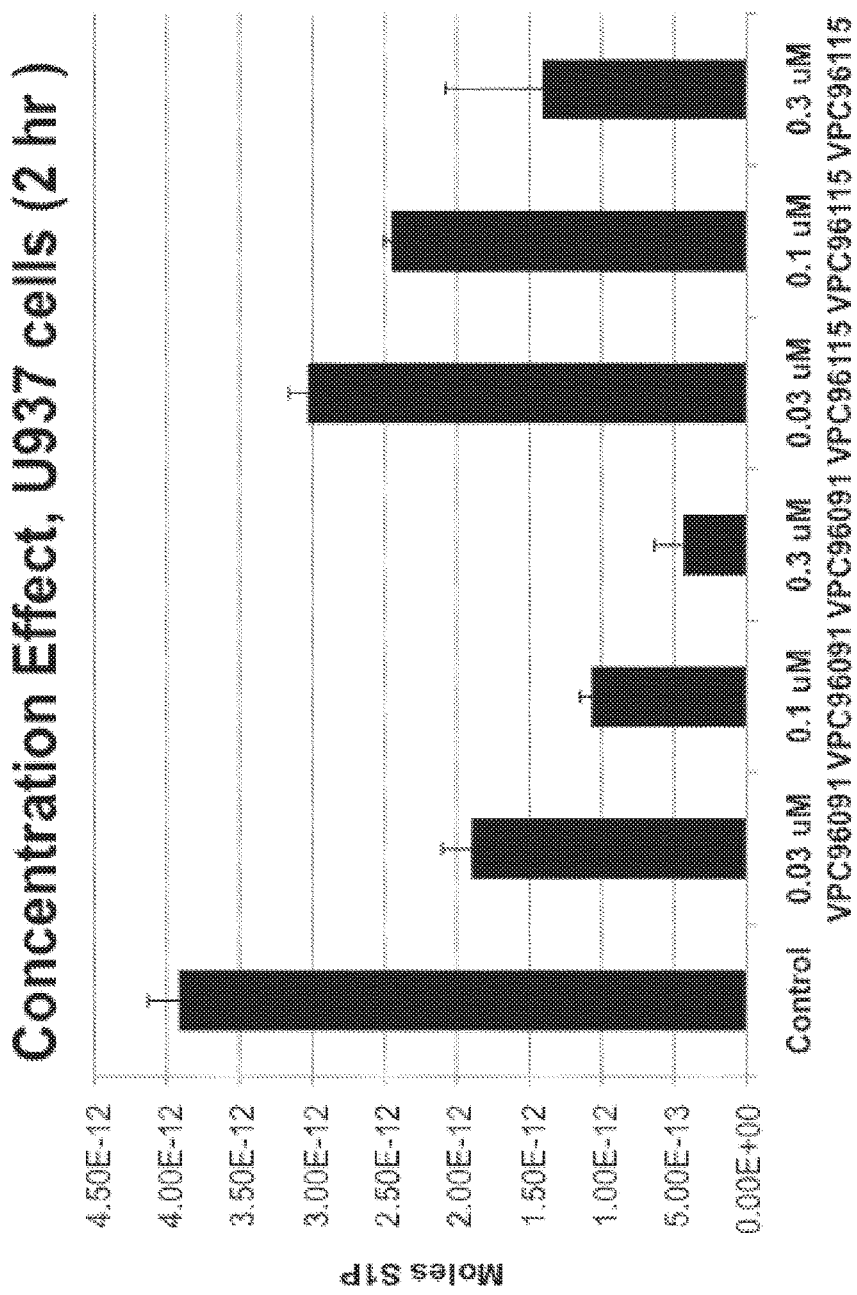

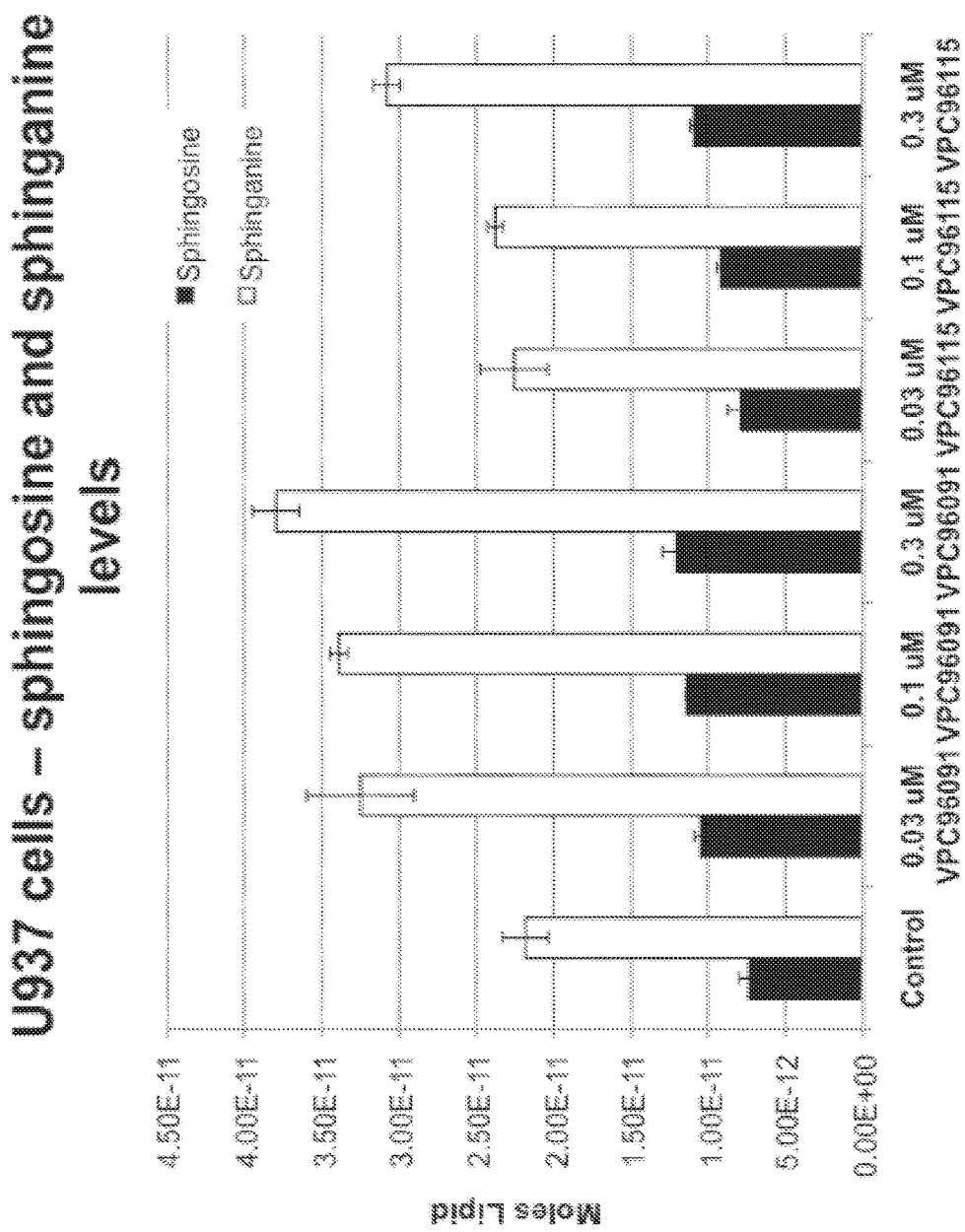

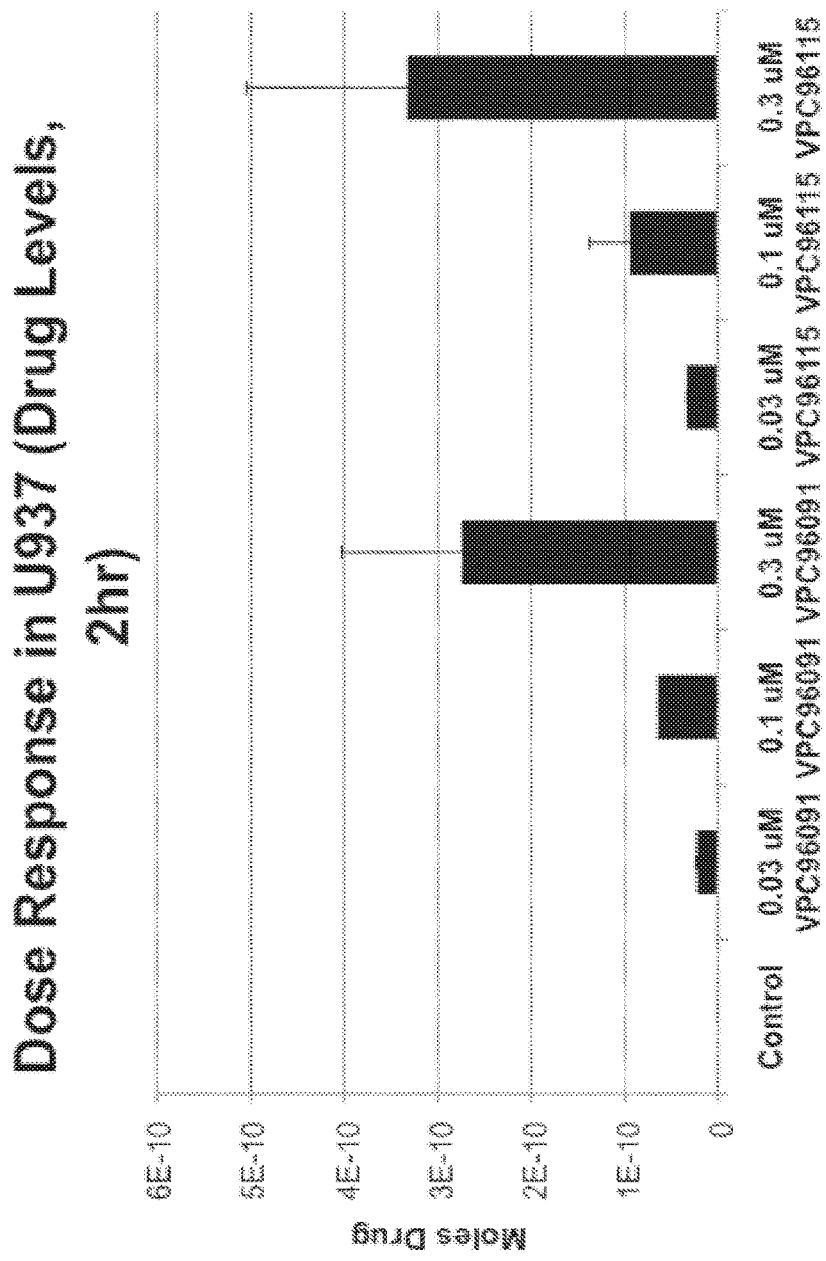

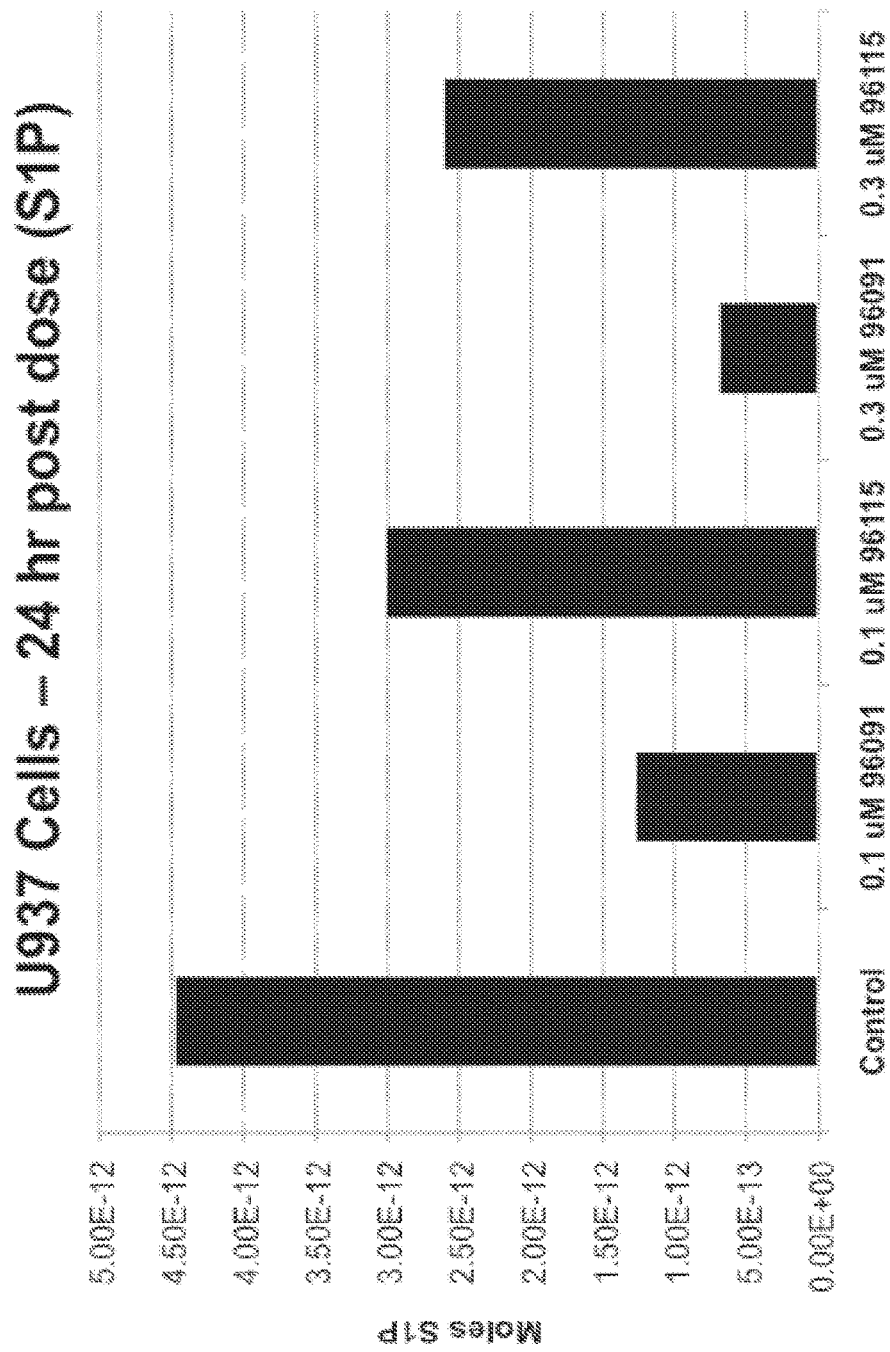

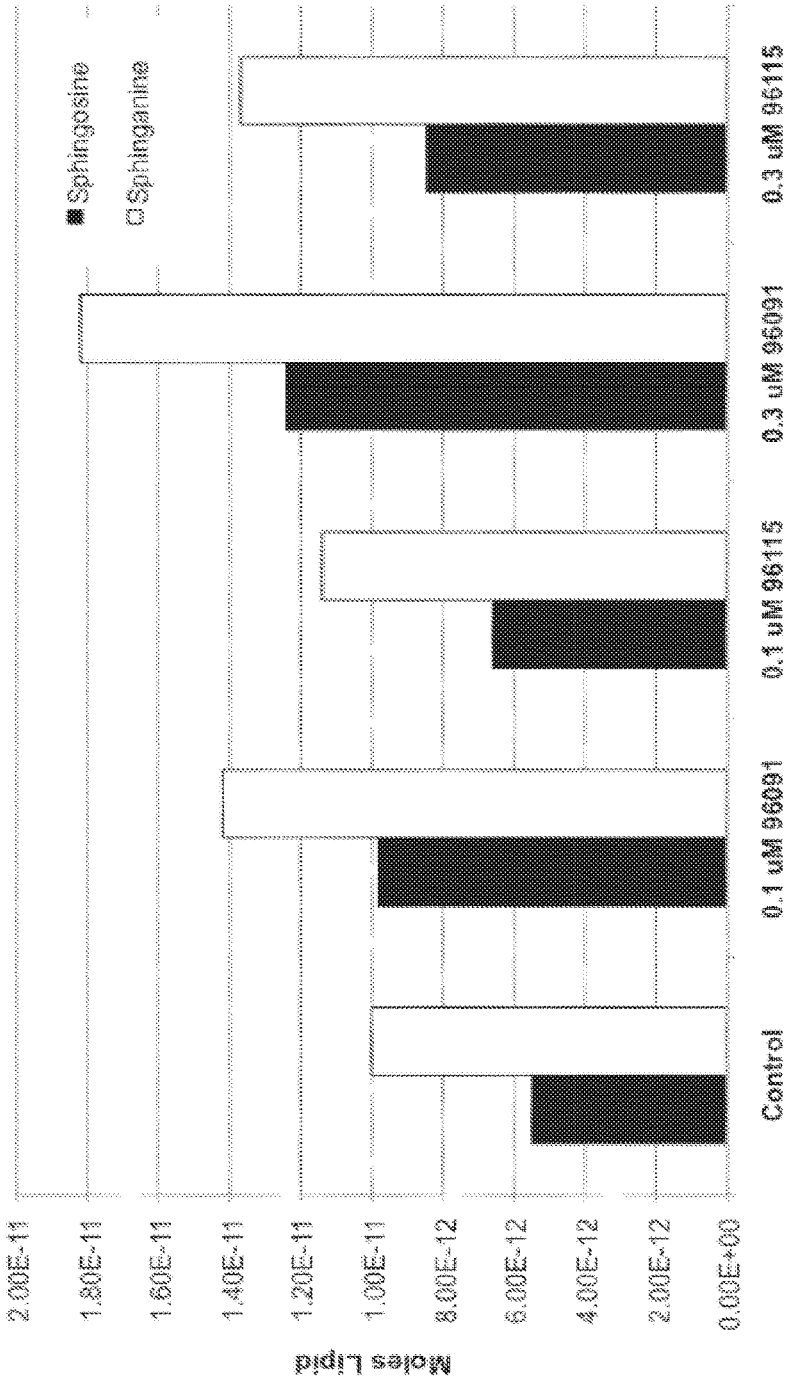

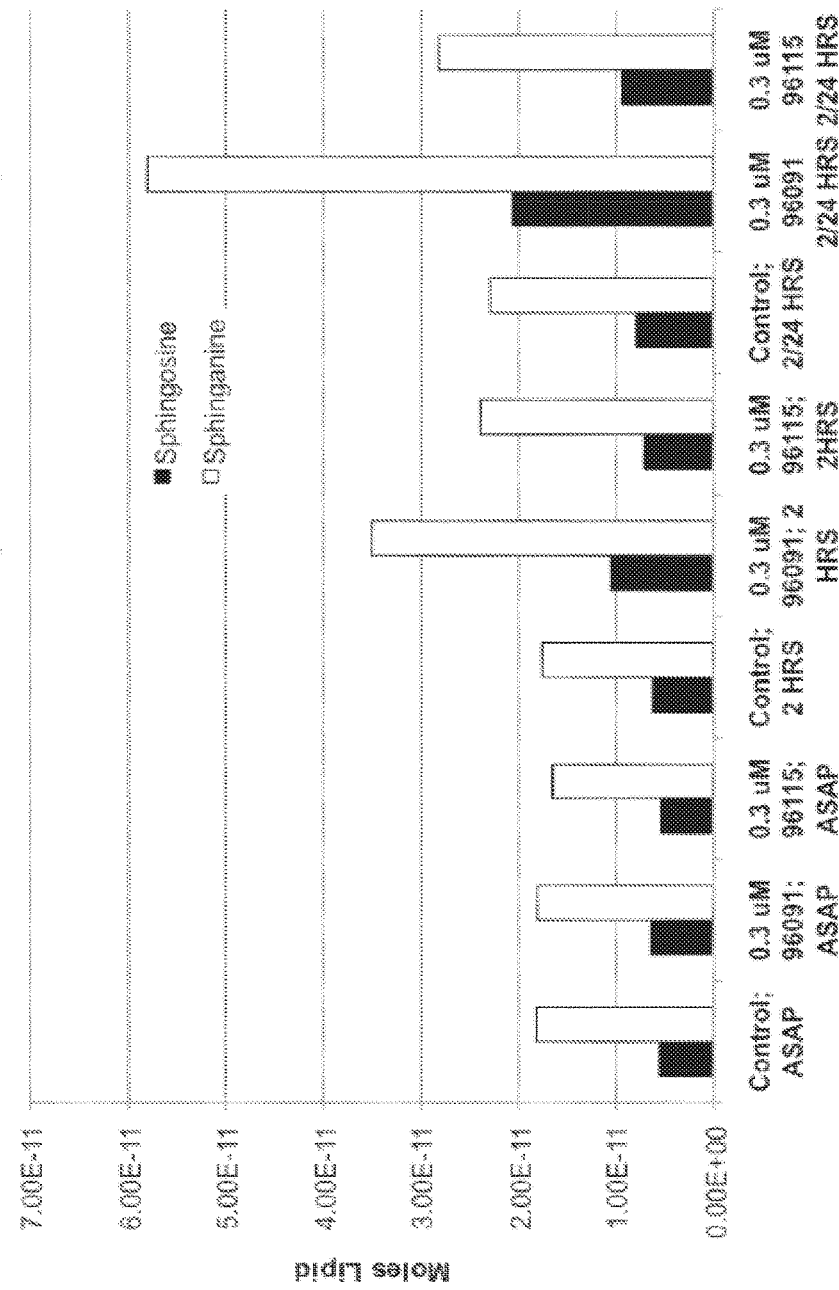

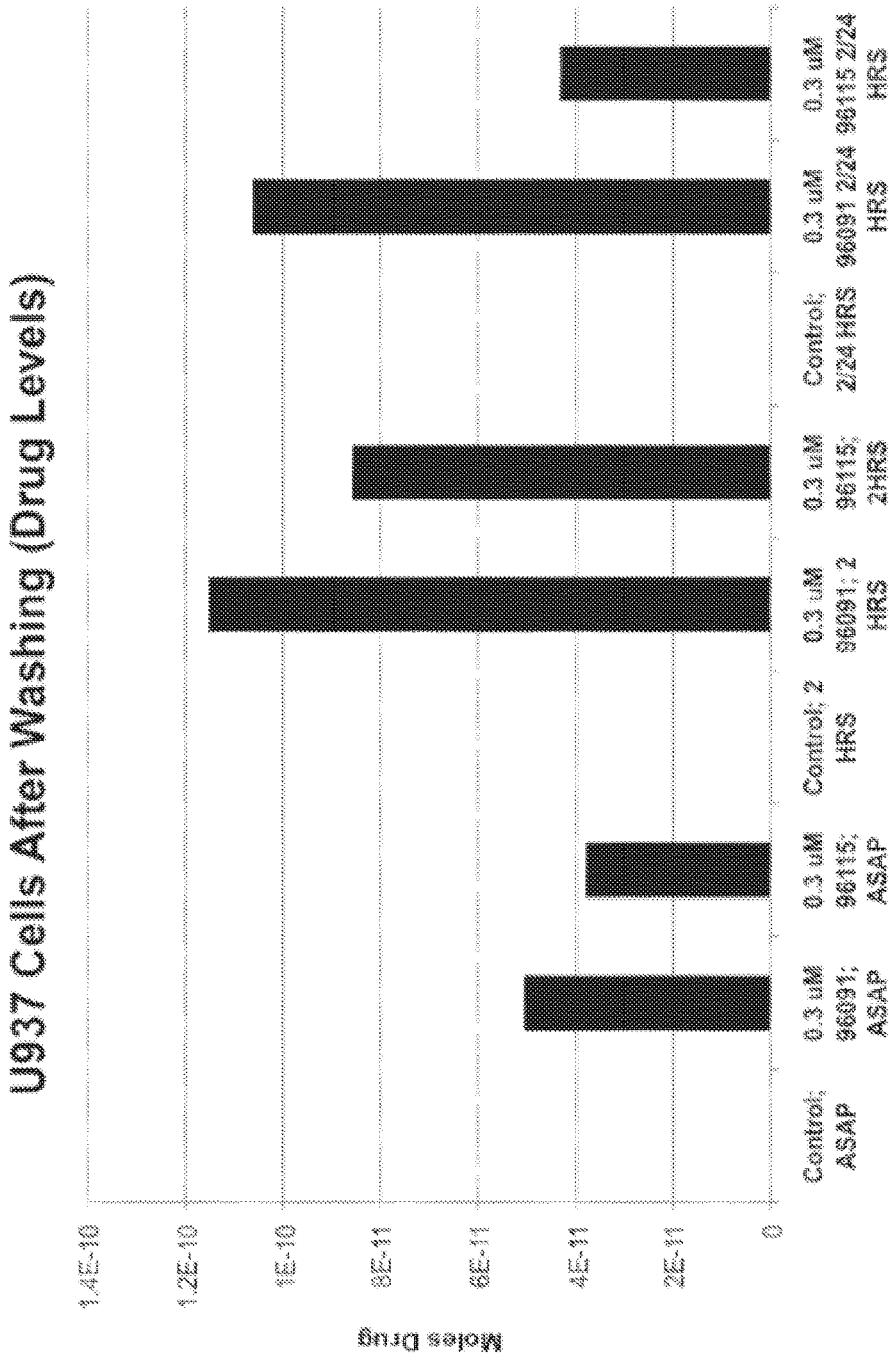

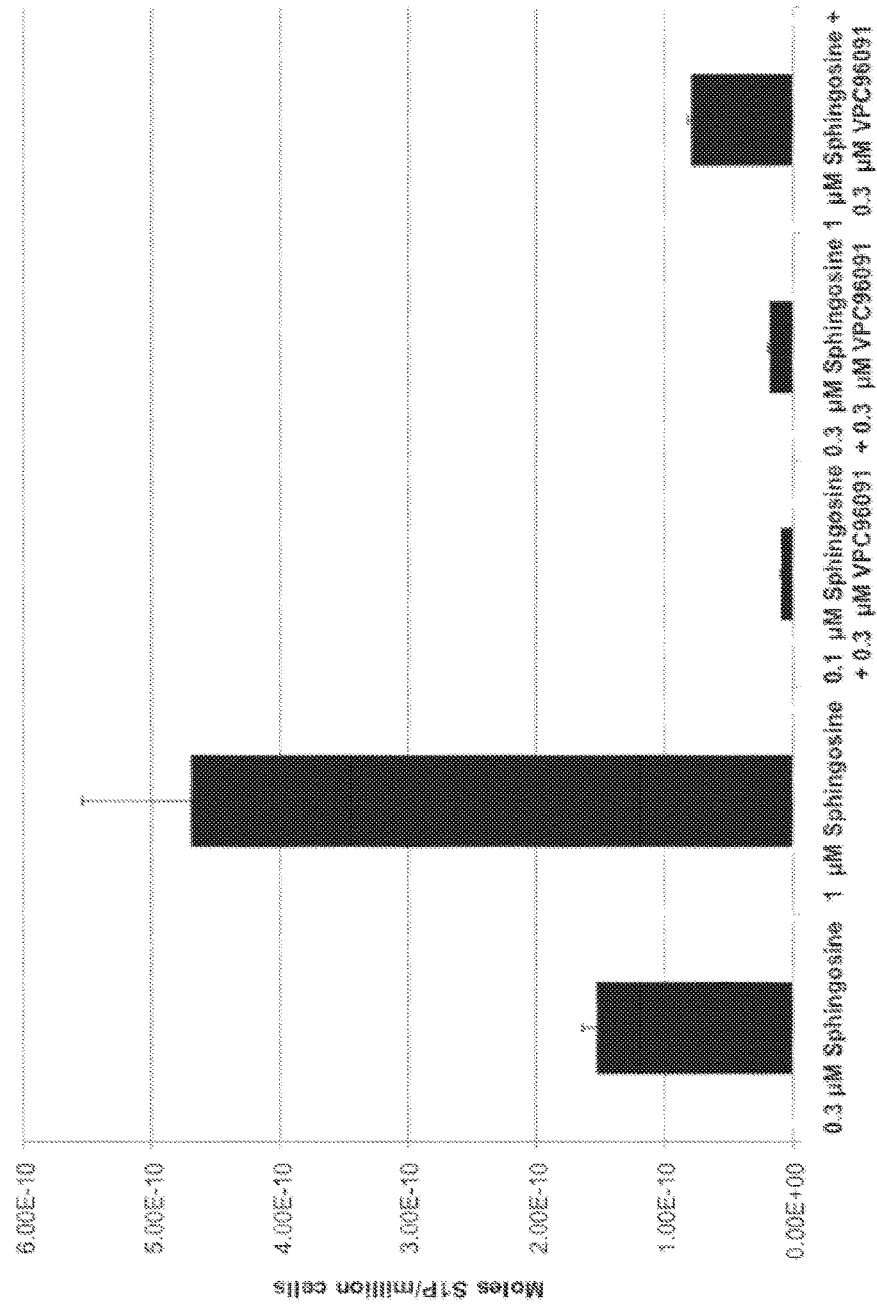

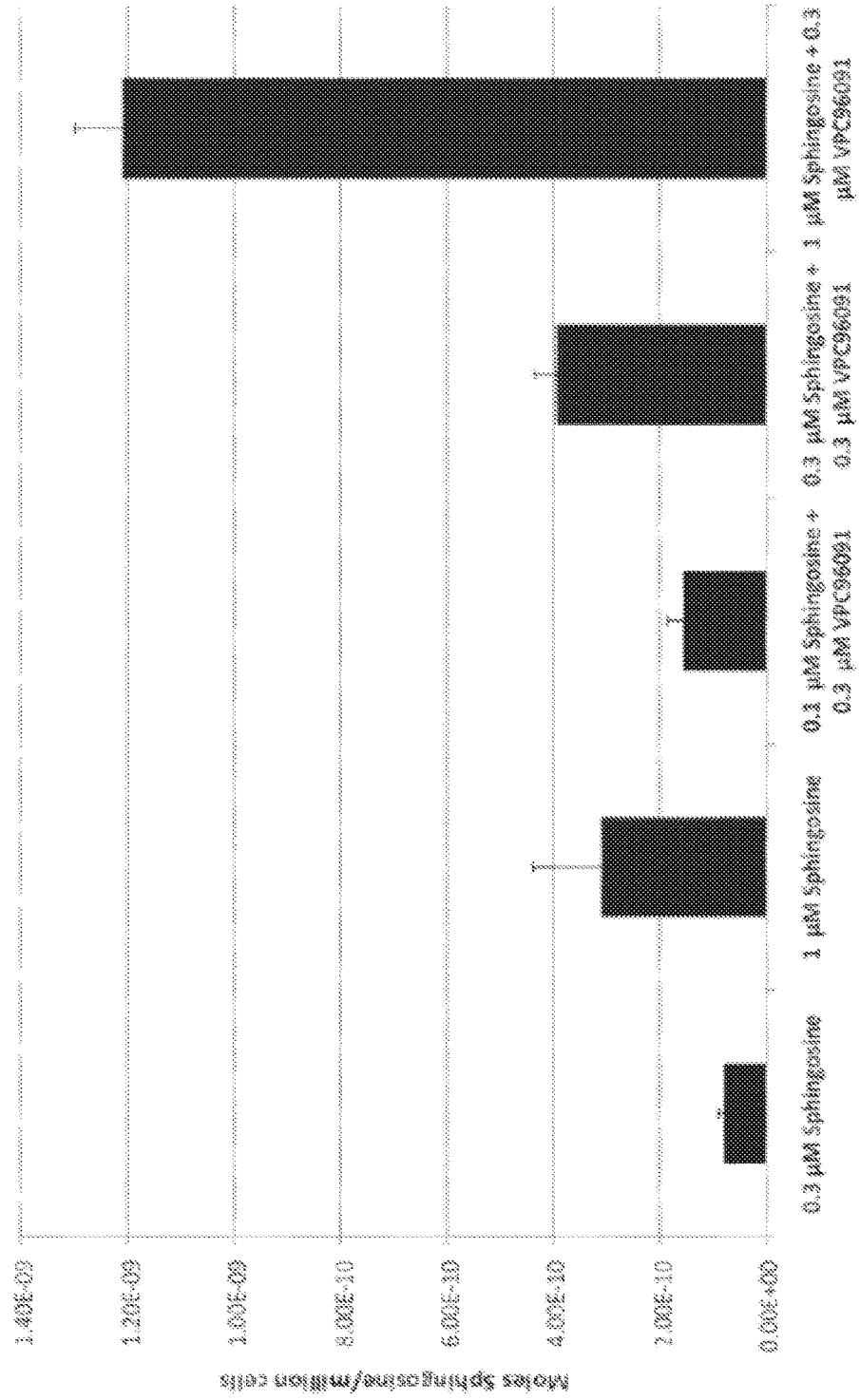

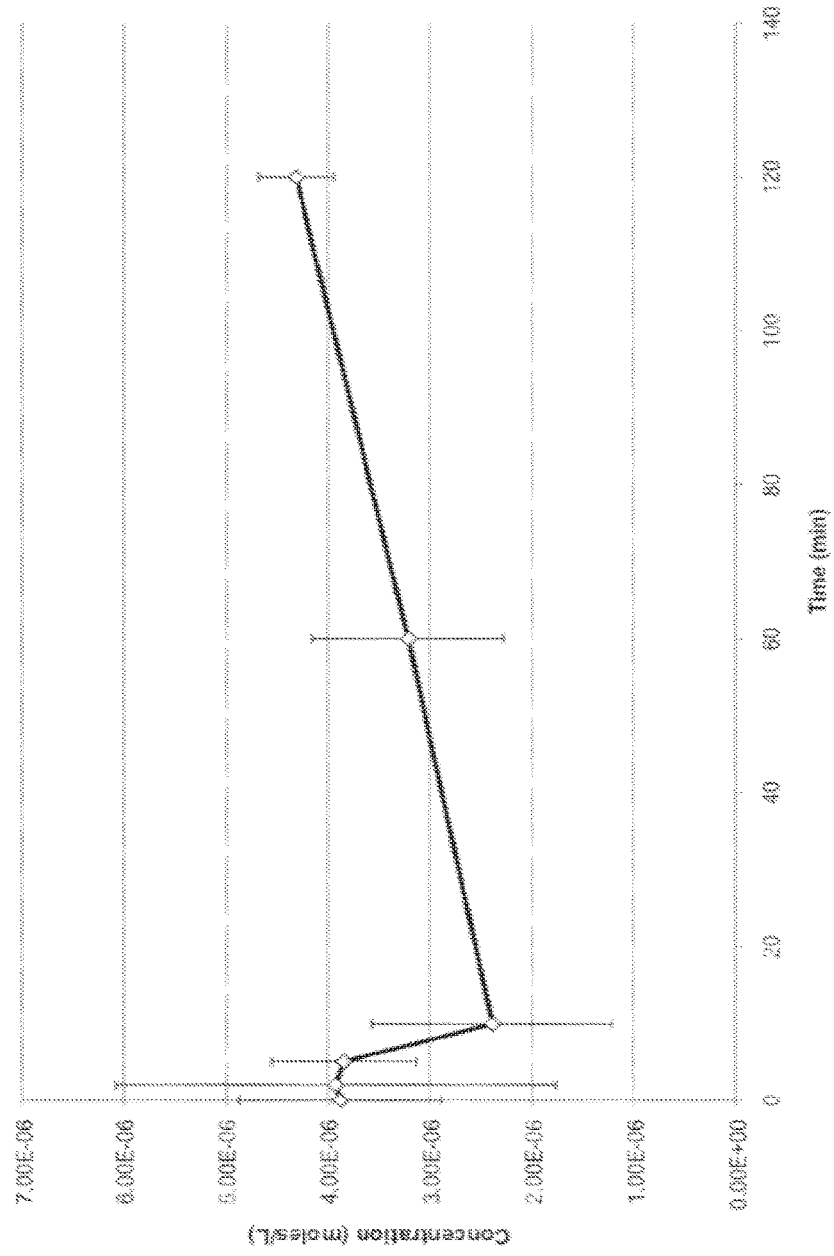

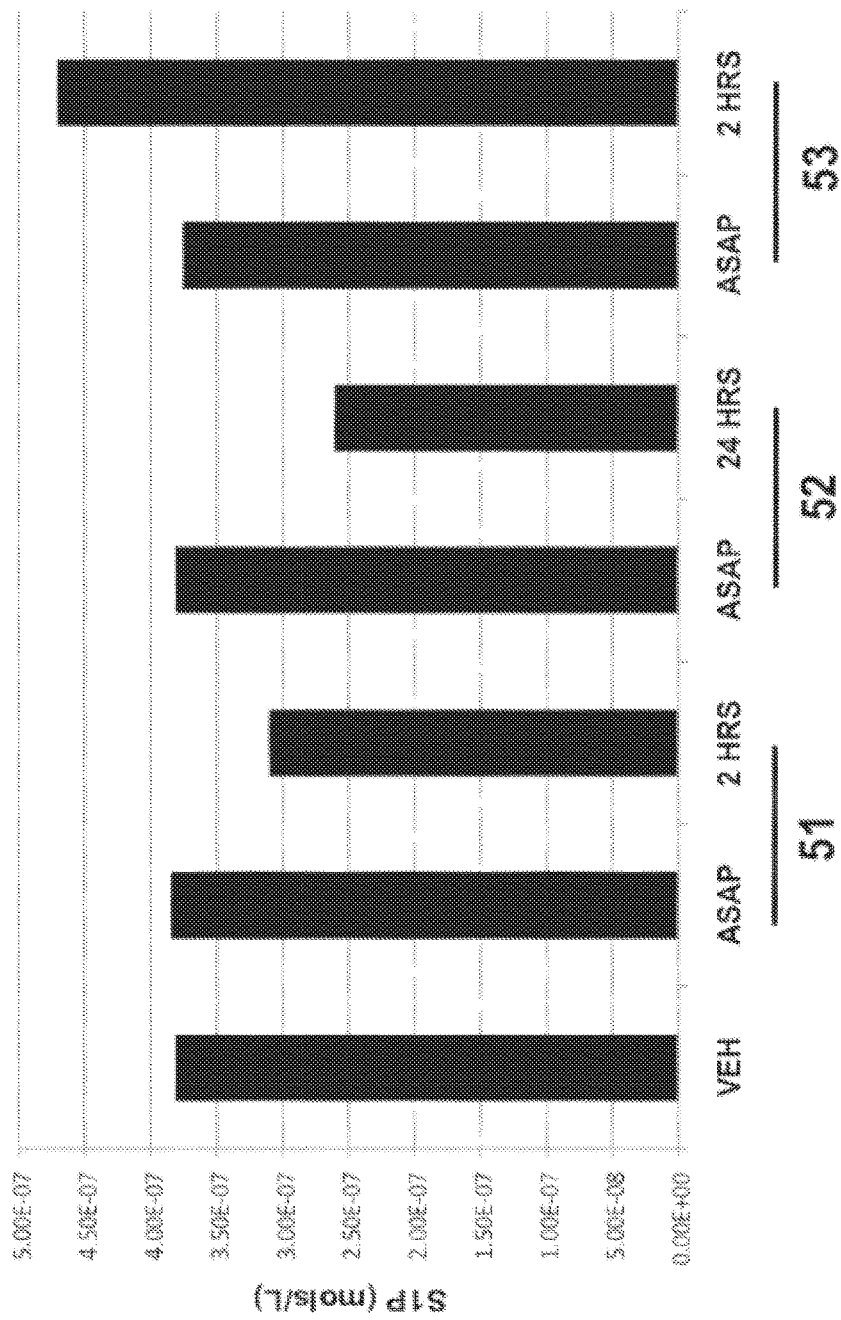

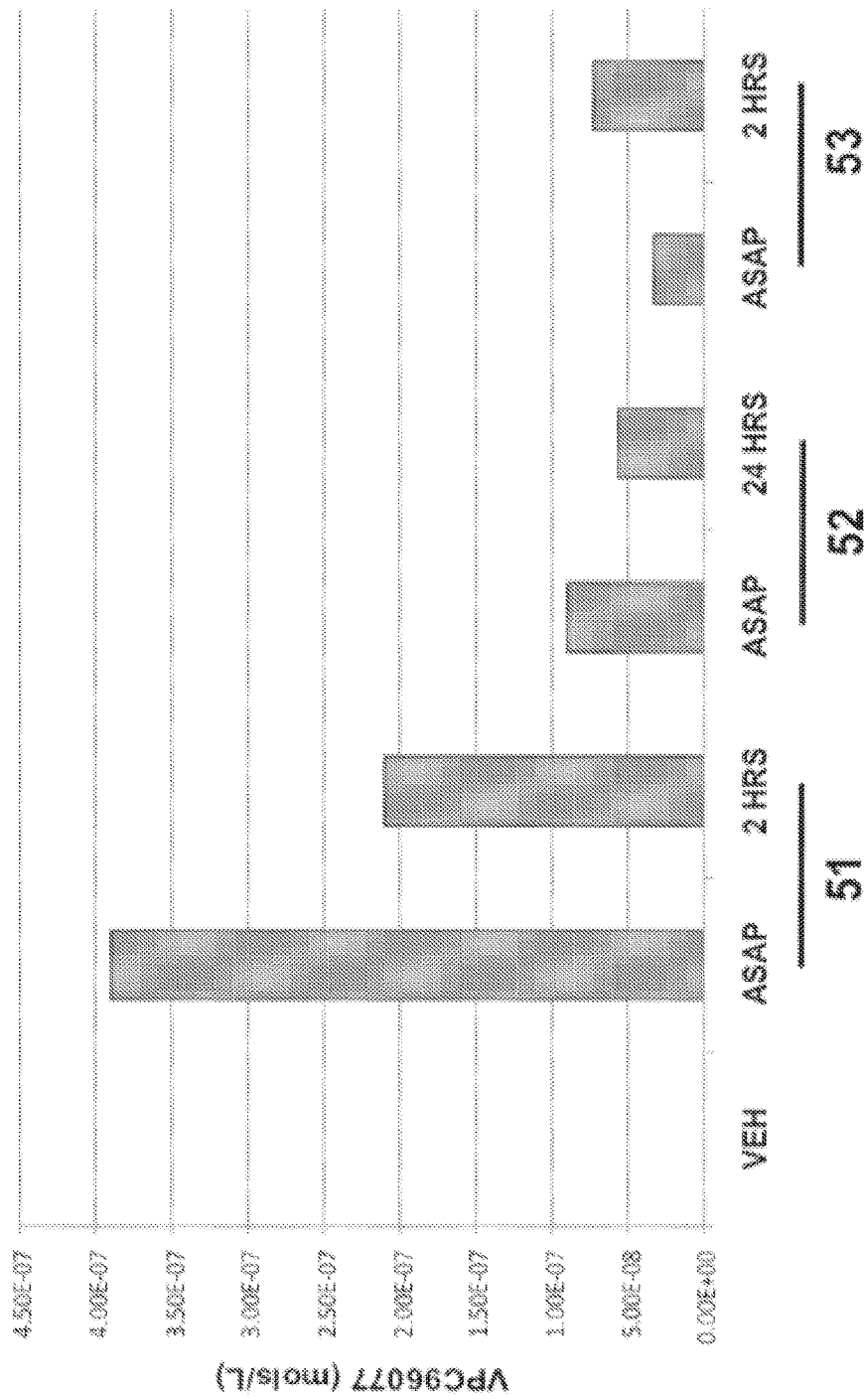

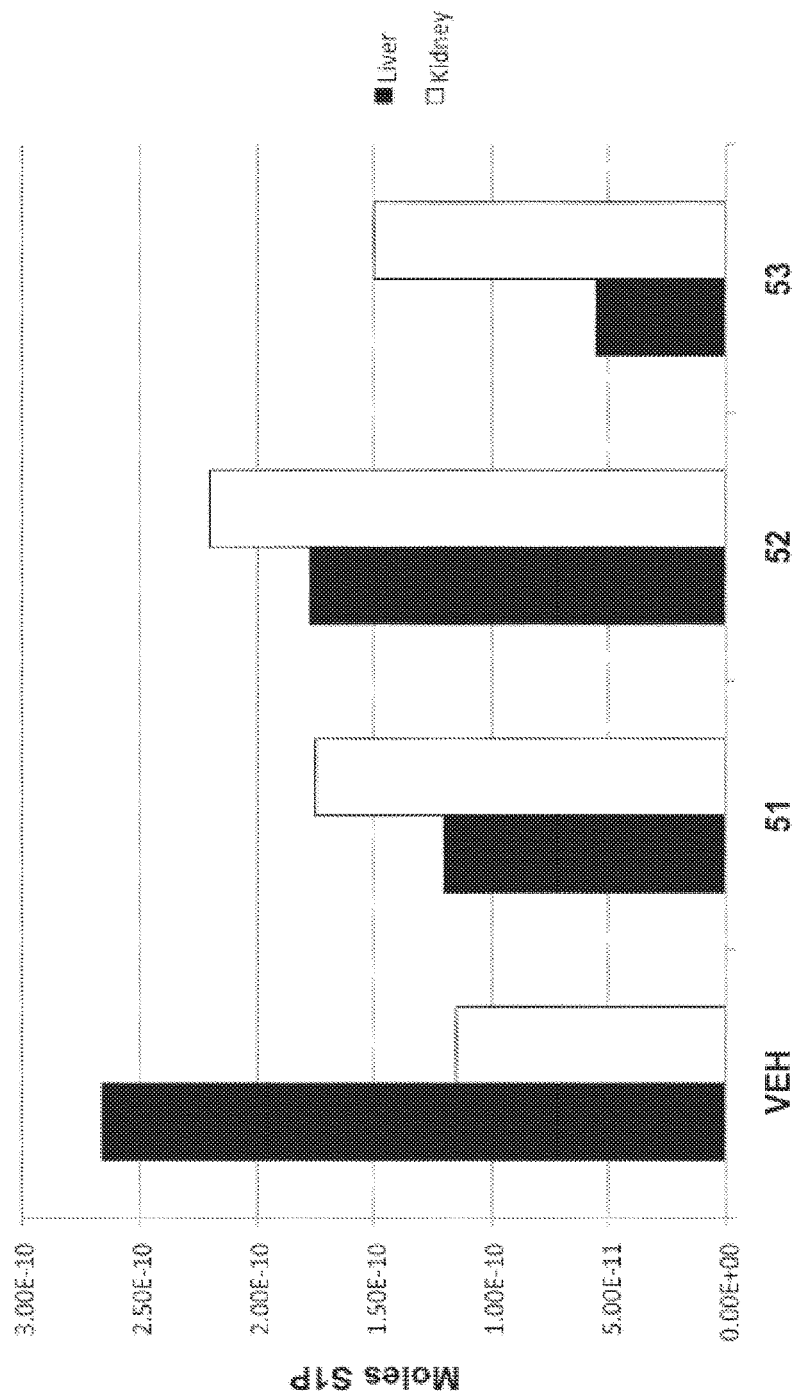

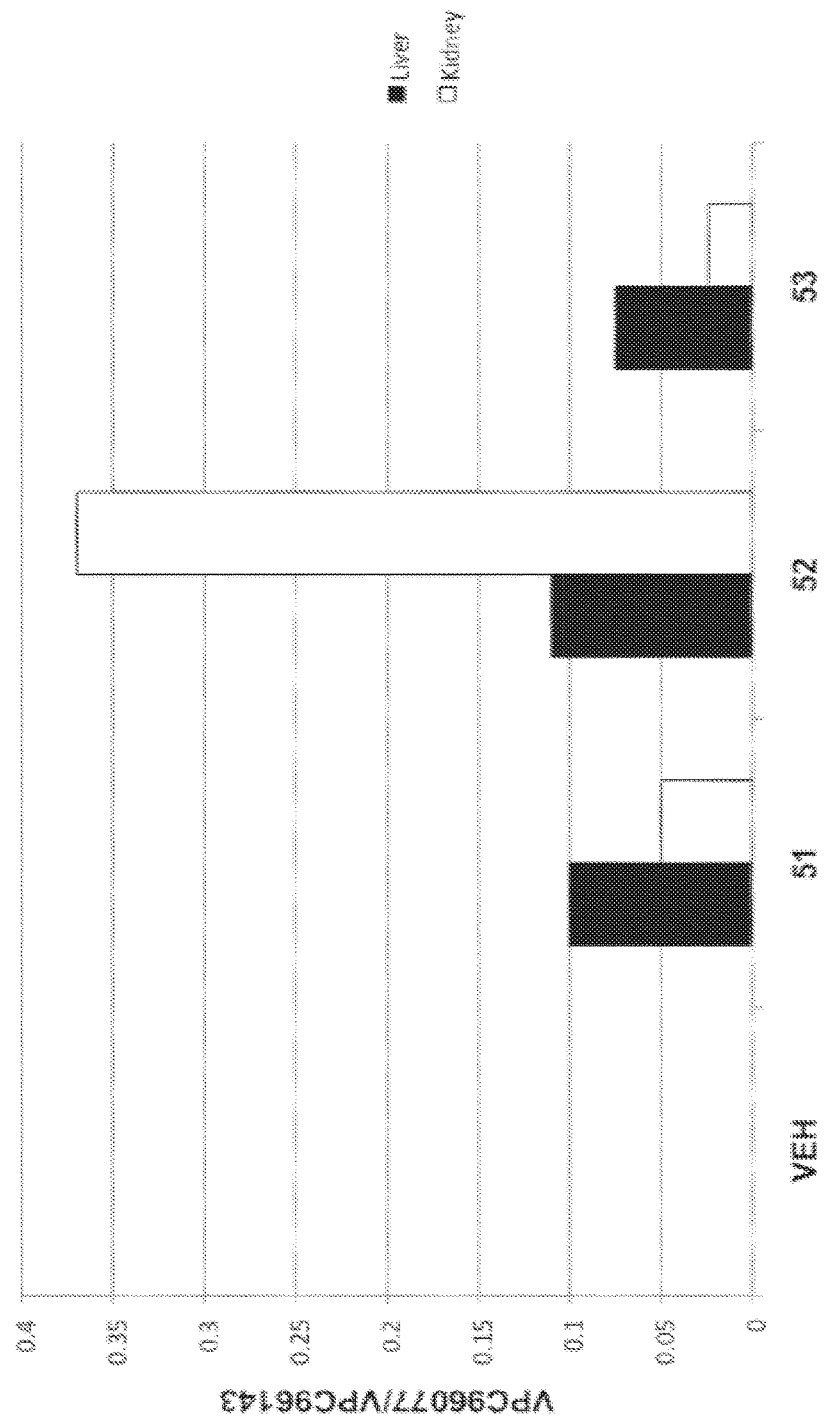

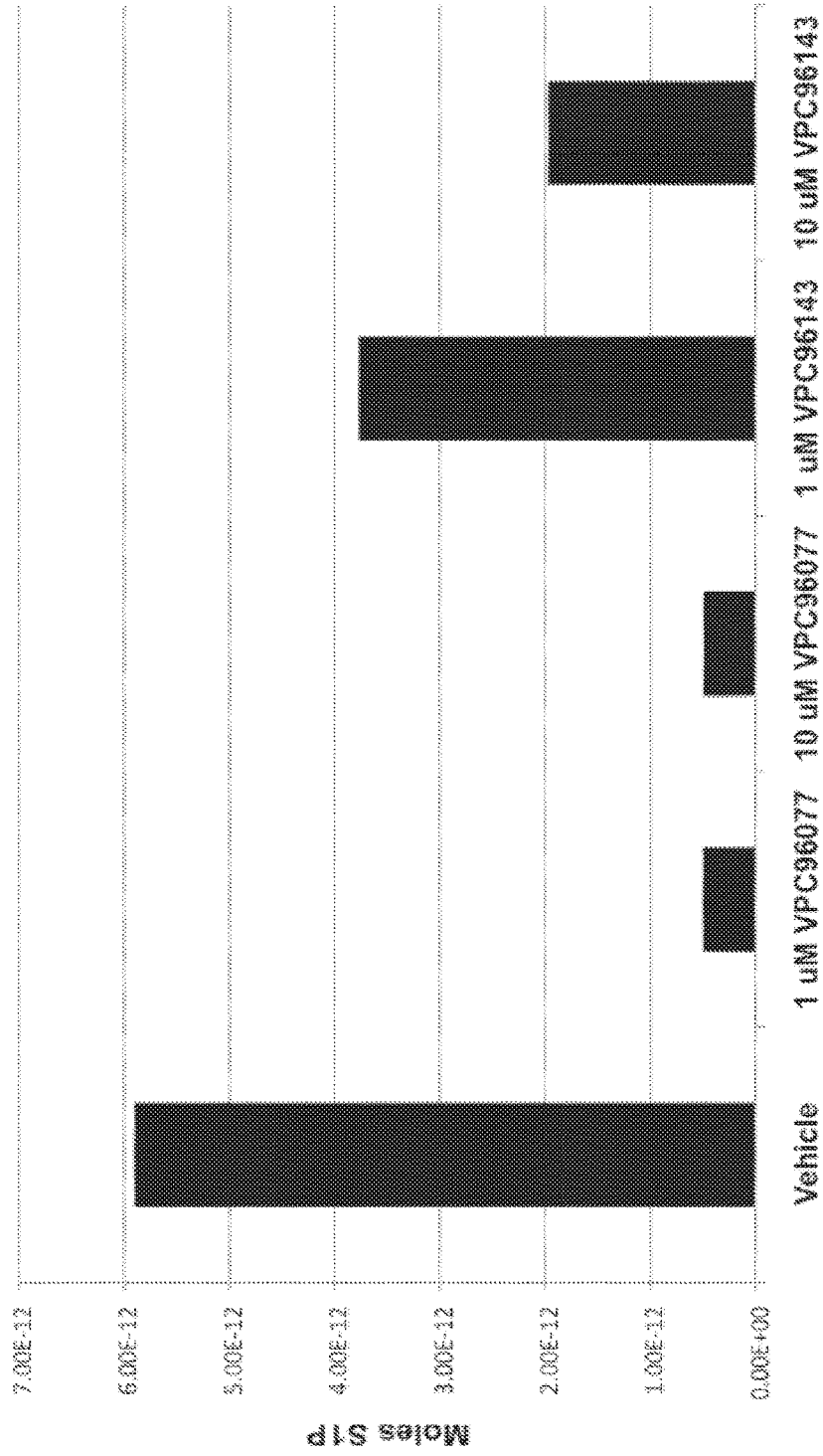

IMIDAMIDE SPHINGOSINE KINASE INHIBITORS

PRIORITY

This application is a continuation of U.S. patent application Ser. No. 13/390,207 that was filed on Apr. 27, 2012 and now is U.S. Pat. No. 9,421,177 and that was a national stage of international application PCT/US2010/045660 filed on Aug. 16, 2010, and that claims priority from U.S. Provisional Application No. 61/233,963, filed Aug. 14, 2009, the disclosures of which applications are incorporated by reference.

GOVERNMENT FUNDING

This invention was made in part with United States Government support under Grant No. RO1 GM 067958 awarded by the National Institutes of Health. The United States Government has certain rights in the invention.

BACKGROUND

Sphingosine 1-phosphate (S1P) is a lysophospholipid mediator that evokes a variety of cellular responses by stimulation of five members of the endothelial cell differentiation gene (EDG) receptor family. The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. Ultimately, this S1P-driven signaling results in cell survival, increased cell migration and, often, mitogenesis. The recent development of agonists targeting S1P receptors has provided insight regarding the role of this signaling system in physiologic homeostasis. For example, the immuno-modulator, FTY720 (2-amino-2-[2-(4-octylphenyl) ethyl] propane 1,3-diol), that following phosphorylation, is an agonist at 4 of 5 S1P receptors, revealed that enhancing S1P tone influences lymphocyte trafficking. Further, S1P type 1 receptor (S1P1) antagonists cause leakage of the lung capillary endothelium, which suggests that S1P may be involved in maintaining the integrity of the endothelial barrier in some tissue beds. S1P is synthesized by the action of two enzymes, sphingosine kinase types 1 and 2 (SphK1, SphK2), in transferring a phosphate residue from ATP to sphingosine (the enzymes also catalyze the phosphorylation of sphinganine to yield sphinganine 1-phosphate (dihydroS1P)).

Sphingosine 1-phosphate (S1P) has been demonstrated to induce many cellular processes, including those that result in platelet aggregation, cell proliferation, cell morphology, tumor-cell invasion, endothelial cell chemotaxis and angiogenesis. For these reasons, sphingosine kinases are good targets for therapeutic applications such as wound healing and tumor growth inhibition.

The importance of sphingosine kinase 1 and 2 (SphK1 & SphK2) in survival and proliferation has also been recognized. SphK1 & SphK2 catalyze the phosphorylation of the endogenous lipid D-erythro sphingosine to sphingosine 1-phosphate (S1P). SphK1 & SphK2 are also responsible for the equilibrium between the anti-apoptotic S1P and its pro-apoptotic metabolic precursor sphingosine and its precursor, ceramide. Thus, SphK1 & SphK2 have been proposed to be important drug targets. However, only a small number of compounds have been shown to inhibit the sphingosine kinases, including DL-threo-dihydrosphingosine, N,N-dimethylsphingosine and short-chain DL-erythro-sphingosine analogues. However, these compounds are not suitable as in vivo inhibitors and cannot address questions concerning SphK mediated disease states.

Traditional methods of inhibiting sphingosine kinases have centered on targeting the ATP binding site of the kinase, a strategy that has enjoyed moderate success. However, such methods suffer from limited of selectivity across a wide array of kinases. Additionally, the sequence of the ATP binding domain of SphK1 & SphK2 is conserved across a number of diacylglycerol (DAG) kinase family members, rendering the traditional strategy problematic.

Currently, there is a need for novel, potent, and selective agents that inhibit the substrate-binding domain of the sphingosine kinases (e.g., human SphK1 and SphK2) that have enhanced potency, selectivity, and oral bioavailability. In addition, there is a need in the art for identification of, as well as the synthesis and use of such compounds. The present invention satisfies these needs.

SUMMARY

The present invention provides, in one aspect, compounds that inhibit sphingosine kinase 1 and sphingosine kinase 2 (SphK1 & SphK2) enzymes. Accordingly, there is provided compounds of Formula IA:

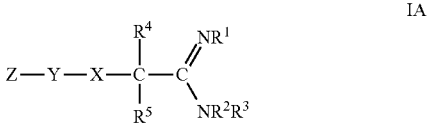

wherein: $R^1$ is hydrogen or OH; $R^2$ and $R^3$ are independently hydrogen, $(C_1-C_4)$alkyl; or halo$(C_1-C_3)$alkyl;

$R^4$ is $NH_2$ or $(C_1-C_4)$alkyl;

$R^5$ is hydrogen or $(C_1-C_4)$alkyl;

X and Y are independently $CR^6R^7$, $NR^8$, O, S or C=O (carbonyl); $R^6$ and $R^7$ are independently H or $(C_1-C_7)$alkyl; $R^8$ is H or $(C_1-C_7)$alkyl;

X and Y are independently $CR^6R^7$, $NR^8$, O, S or C=O (carbonyl);

$R^6$ and $R^7$ are independently H or $(C_1-C_7)$alkyl; $R^8$ is H or $(C_1-C_7)$alkyl;

wherein $R^4$ and one of $R^5$, $R^6$, $R^7$, or $R^8$ together with the atoms to which they are attached form a ring, optionally including one or more heteroatoms; wherein the heteroatoms are O, S, N or $NR^{10}$; where $R^{10}$ is hydrogen, or $(C_1-C_7)$alkyl;

Z is $(C_6-C_{20})$alkyl, $(C_6-C_{20})$alkenyl, $(C_6-C_{20})$alkynyl, $(C_6-C_{20})$alkoxy, $(C_6-C_{26})$alkoxyalkyl, $(C_6-C_{12})$cycloalkyl, $(C_6-C_{10})$aryl, $(C_{12}-C_{20})$alkylaryl, $(C_{12}-C_{20})$alkoxylaryl $(C_7-C_{30})$arylalkyl, $(C_2-C_{10})$heterocyclic, $(C_4-C_{10})$heteroaryl, or $(C_4-C_{10})$heteroaryl$(C_1-C_{20})$alkyl; and $R^{10}$ is hydrogen, or $(C_1-C_7)$alkyl; wherein the Z groups are optionally substituted with 1, 2, 3, 4, 5, 6, or 7 substituents; where the substituents are halo, halo$(C_1-C_{10})$alkyl, cyano, $-NR^aR^b$, $(C_1-C_{20})$alkoxy, $(C_2-C_{26})$alkoxyalkyl, $(C_3-C_{12})$cycloalkyl, $(C_6-C_{10})$aryl, $(C_7-C_{30})$alkylaryl, $(C_2-C_{10})$heterocyclic, or $(C_4-C_{10})$-heteroaryl; wherein one or more of the carbon atoms in the Z alkyl groups can be independently replaced with non-peroxide oxygen, sulfur or $NR^c$; where each $R^a$, $R^b$, or $R^c$ is independently H or $(C_1-C_7)$alkyl. The invention includes pharmaceutically acceptable salts of the compounds of Formula IA.

In another aspect, the disclosed compounds and methods are directed to SphK enzyme inhibitors that have activity as selective inhibitors of the SphK1 enzyme or SphK2 enzyme or have activity as inhibitors of both SphK1 and SphK2 enzymes.

In another aspect, the present invention provides a method for inhibiting angiogenesis in a tumor, including contacting cancerous cells with an effective amount of a compound of Formula IA, or a pharmaceutically acceptable salt or ester thereof.

In another aspect, the present invention provides compositions and methods for the use of SphK inhibitors for the treatment of neoplastic disease. In one aspect, this treatment is effected by application of SphK inhibitors that are efficacious by virtue of their anti-angiogenic properties.

In another aspect, the present invention provides a method for preventing or treating diseases that involve excess vascular growth, e.g. retinal degenerative diseases such as macular degeneration, comprising contacting the affected area with an effective amount of the compound of Formula IA. For example the compound can be injected into the posterior eye in depot form.

In another aspect, the invention provides a method for repairing a vascular injury following catheterization, including contacting the lumen of the affected vessel with an effective amount of the compound of Formula IA. In another aspect, the invention includes coating indwelling stents with a compound of Formula IA.

In another aspect, the invention provides a method for parenteral delivery of a compound of formula IA prior to and/or following intravascular stenting.

In another aspect, the present invention provides compositions and methods for the use of SphK inhibitors to prevent and inhibit vascular restenosis following a vascular injury. For example, the injury can be due to balloon angioplasty. In another aspect, the present invention includes a method for treating subjects to prevent vascular restenosis.

In another aspect, the present invention provides compositions and methods for the use of SphK inhibitors to prevent asthma attacks. In one aspect, the asthma could be due to over production of cysteinyl leukotrienes. In another aspect, the present invention includes a method for treating subjects suffering from asthma.

In another aspect, the present invention provides a metal stent coated directly on the surface with of a compound of Formula IA. The compound of Formula IA is delivered to the stented vessel wall by direct contact of the stent struts with the vessel wall.

In another aspect, the present invention provides a compound of Formula IA incorporated into a non-degradable polymer or co-polymer, such as but not restricted to polyethylene-co-vinyl acetate (PEVA) and poly n-butyl methacrylate, and coating a bare metal stent with the polymer.

In another aspect, the present invention provides a compound of Formula IA is incorporated into a biodegradable polymer or co-polymer, such as but not limited to poly lactic acid glycolic acid (PLGA) or phosphorylcholine, and coating a bare metal stent with the polymer. The compound of Formula IA is delivered to the stented vessel wall by elution from the biodegradable polymeric surface on the stent.

In another aspect, the present invention provides a compound of Formula IA incorporated into a stent device that contains a nanoporous surface modification, such as but not limited to a ceramic, metal or other material coated on the bare metal stent as a nanoporous surface modification. The compound of Formula IA is delivered to the stented vessel wall by elution from the nanoporous surface.

In another aspect, the present invention provides a non-metallic biodegradable or non-degradable stent device combined with a compound of Formula IA. The compound of Formula IA is delivered to the stented vessel wall by elution from the non-metallic biodegradable or non-biodegradable stent matrix.

In another aspect, the invention provides a compound of Formula IA, a pharmaceutically acceptable salt or ester thereof for use in medical treatment (for example, treatment of neoplastic disease).

In another aspect, the invention provides a compound of Formula IA, a pharmaceutically acceptable salt or ester thereof for use in medical treatment for example treatment of fibrotic disease such as pulmonary fibrosis.

In another aspect, the invention provides a compound of Formula IA, a pharmaceutically acceptable salt or ester thereof for use in medical treatment for example treatment of sepsis.

In another aspect, the invention provides a compound of Formula IA, a pharmaceutically acceptable salt or ester thereof for use in medical treatment for example treatment of autoimmune diseases such as multiple sclerosis, psoriasis, rheumatoid arthritis or uveitis.

In another aspect, the invention provides a method for the use of a compound of Formula IA or a pharmaceutically acceptable salt or ester thereof to prepare a medicament for inhibiting tumor growth, metastasis or tumor angiogenesis. In another aspect, the invention provides a method for the use of a compound of Formula IA or a pharmaceutically acceptable salt or ester thereof to prepare a medicament for preventing or treating a vascular injury, fibrosis, sepsis, asthma, or an autoimmune disease in a mammalian species (for example, a human).

The present invention also includes pharmaceutical compositions including the disclosed compounds. More particularly, such compounds can be formulated as pharmaceutical compositions using standard pharmaceutically acceptable carriers, fillers, solubilizing agents and stabilizers known to those skilled in the art. For example, a pharmaceutical composition including a disclosed compound, analog, derivative, or modification thereof, as described herein, is used to administer the appropriate compound to a subject.

In another aspect, the invention provides for the use of a compound of Formula IA or a pharmaceutically acceptable salt or ester thereof to prepare a medicament for repairing a vascular injury following catheterization. In another aspect, the invention includes use of a compound of Formula IA for coating indwelling stents.

In another aspect, the invention provides novel intermediates and processes disclosed herein that are useful for preparing compounds of Formula IA, including the generic and specific intermediates as well as the synthetic processes described herein.

In another aspect, the present invention provides synthetic schemes and methods of use of compounds having Formula IA and analogs or derivatives thereof. In another aspect, the invention provides synthetic and modification schemes for preparing analogs and derivatives of the compounds of Formula IA, as well as compositions and methods for the use of such analogs and derivatives.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The details of one or more embodiments of the invention are set forth in the accompanying description below. Other features, objects, and advantages of the invention will be apparent from the description and drawings, and from the claims.

BRIEF DESCRIPTION OF THE DRAWINGS

FIGS. 2A and 2B illustrate the effect of various concentrations of a compound of Formula 1A on S1P (2A) and sphingosine (Sph) and dihydroSph (2B) accumulation in U937 cells; ca. 5 million cells per point, treatment time 2 hours.

FIG. 2C illustrates accumulation of a test compound of Formula IA in U937 cells (about 100× concentration from surrounding media) after 2 hours of treatment.

FIGS. 3A and 3B illustrate the S1P levels after 24 hours of application of a test compound of Formula IA, e.g., very low levels of sphinganine 1-phosphate (dhS1P, 3B) in U937 cells—off scale on 3A.

FIGS. 4A and 4B illustrate treated U937 cells at times, as soon as possible (asap), 2 hours, or 2 hours/wash, then incubate 24 hours.

FIG. 4C illustrates retention of a compound of the Formula IA in U937 cells after 24 hours in drug free media.

FIG. 5A illustrates the shows effect on synthesis of S1P by a test compound of the Formula IA, in this instance VPC96091. Cells were supplemented with exogenous sphingosine (Sph) at noted concentrations and intracellular S1P was measured with, or without addition of the test compound.

FIG. 5B illustrates the converse effect of that illustrated in slide 5A, i.e., accumulation of intracellular Sph in cells treated with Sph and a test compound of the Formula IA, in this instance VPC96091.

FIGS. 6B and 6C illustrate the change (decrease) in levels of enzyme products, S1P (6B) or dhS1P (6C), in whole rat blood following IV injection of 10 mpk of test compound VPC96091.

FIGS. 7A-7D illustrate the effect of dosing the amidoxime pro-drug, VPC96143, in three mice (#51, 52, 53) at 20 mpk. FIG. 7A illustrates plasma S1P levels. FIG. 7B illustrates accumulation in plasma of the amidine congener, VPC96077, of the amidoxime, VPC96143, and thus the conversion of the amidoxime to the amidine in vivo. FIG. 7C illustrates tissue (liver, kidney) S1P levels. FIG. 7D illustrates the ratio of amidine:amidoxime in liver and kidney.

FIGS. 8A, 8B, 9A, and 9B illustrate the effect on S1P levels and pro-drug conversion using human monocyte U937 cells.

DETAILED DESCRIPTION

Figure 1C:
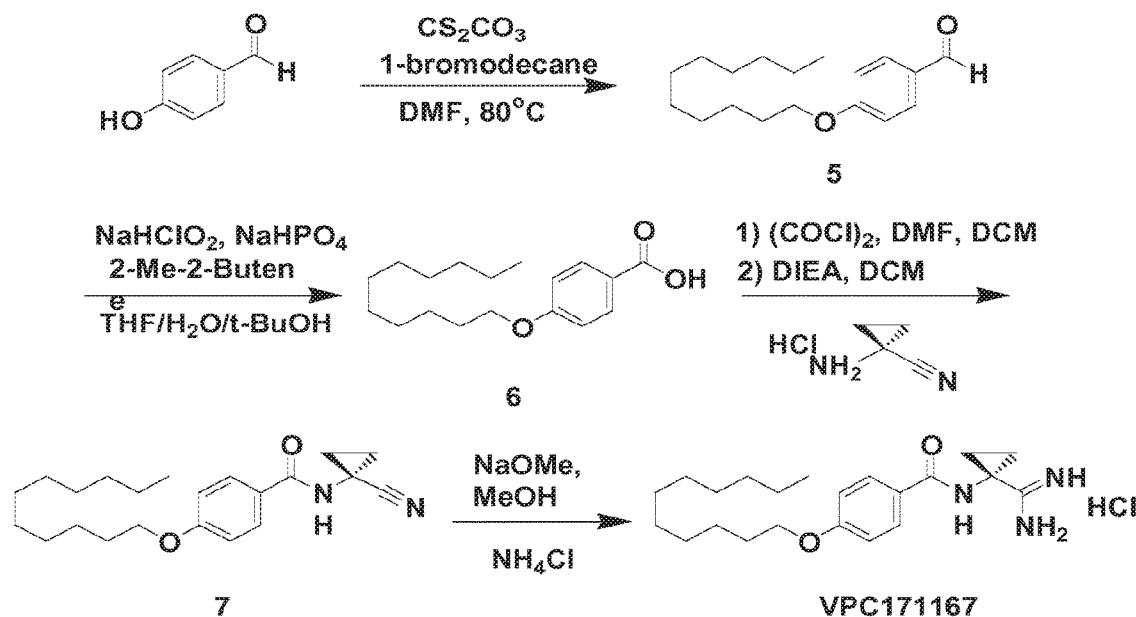
FIGS. 1A-1P illustrate syntheses of compounds of Formula IA.
Figure 1D:
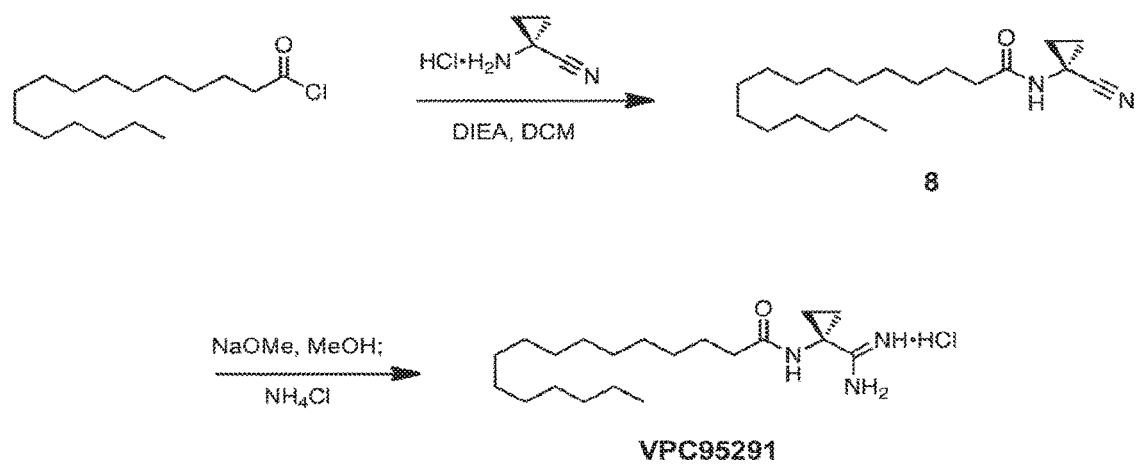
Figure 1E:
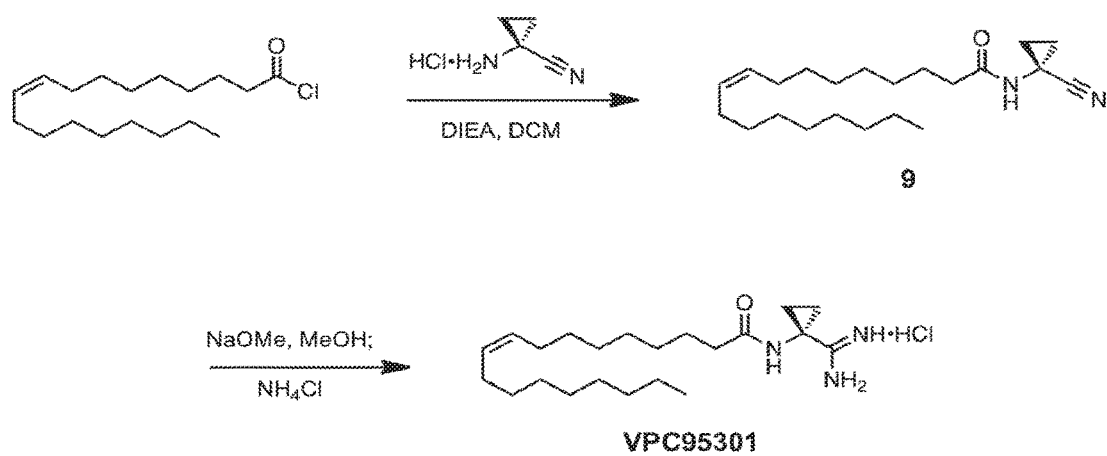
Figure 1F:
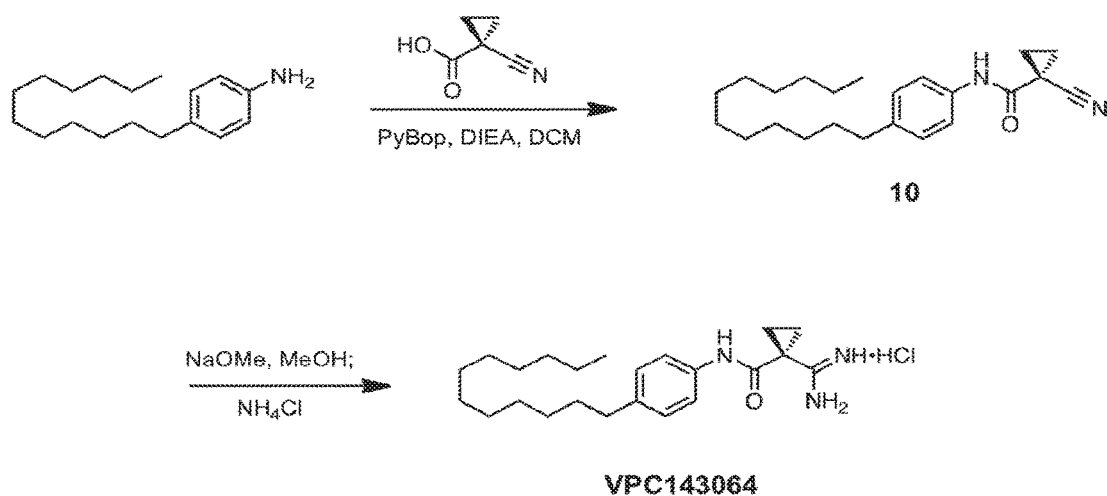
Figure 1H:
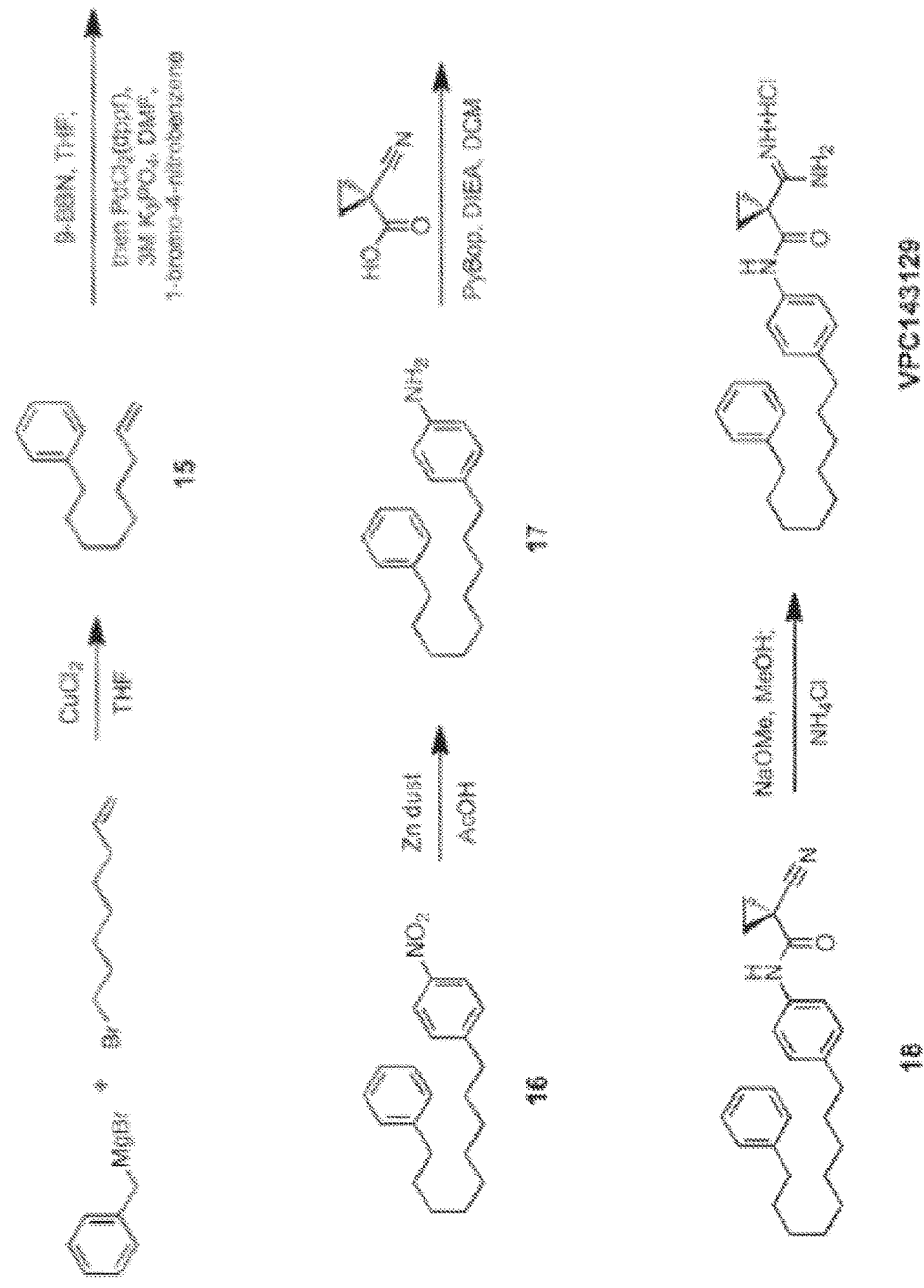
Figure 1J:
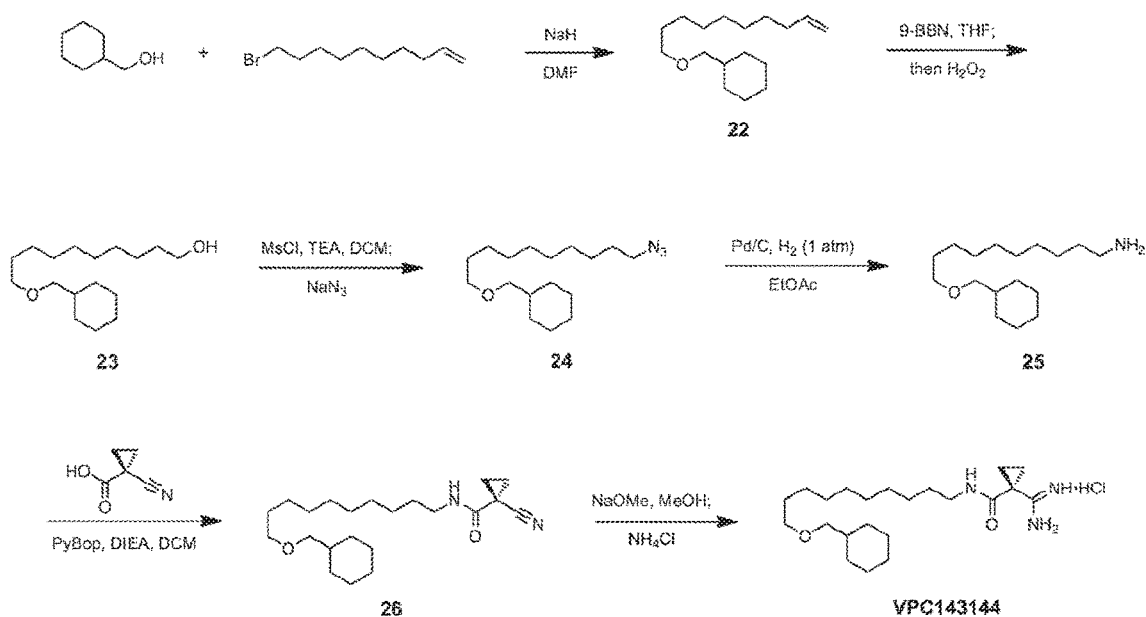
Figure 1K:
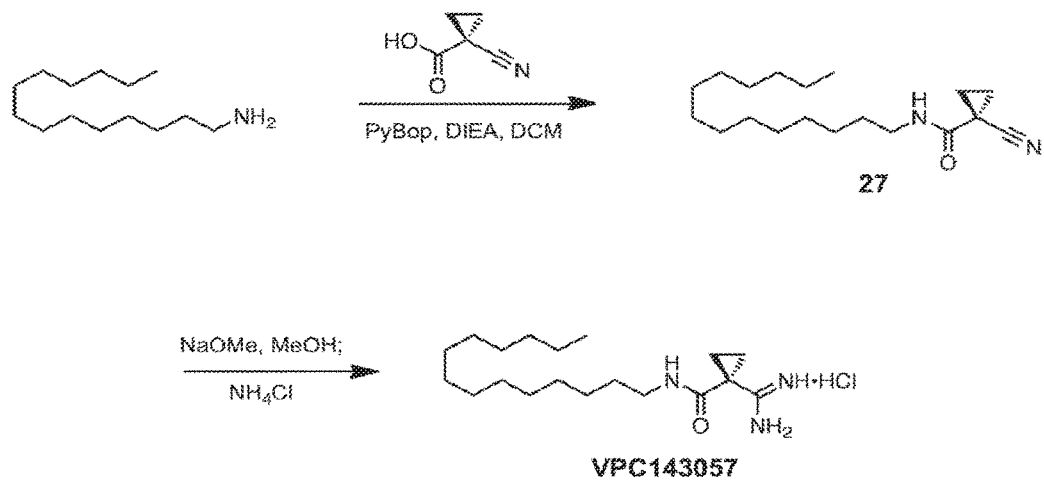
Figure 1L:
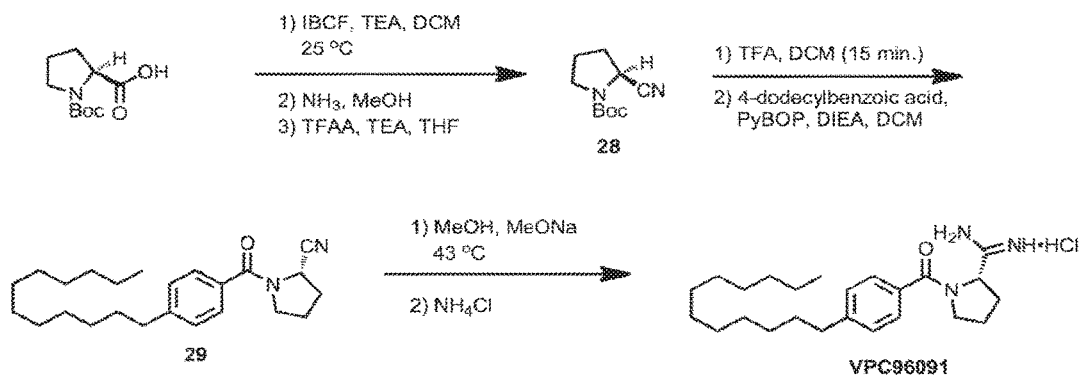
Figure 1M:
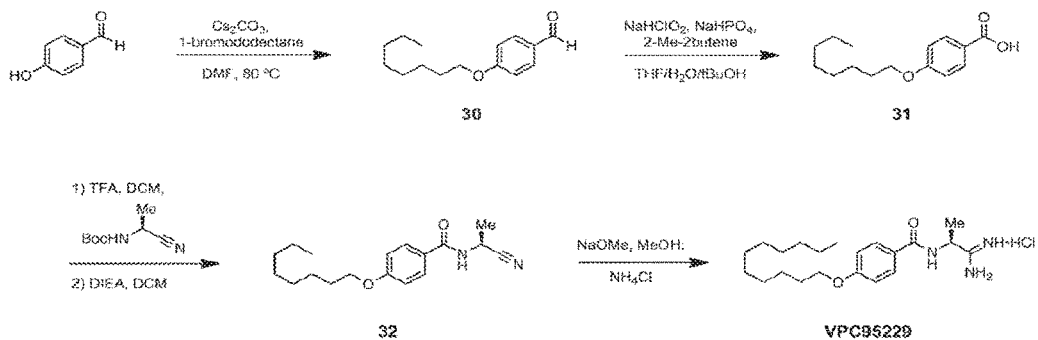
Figure 1N:
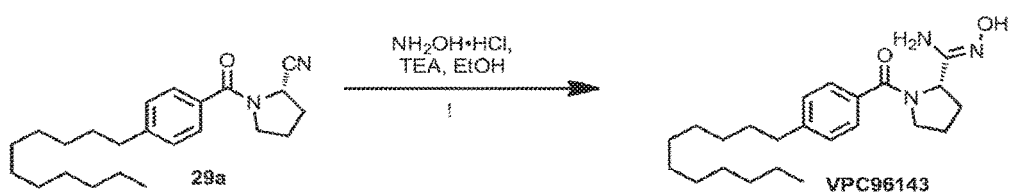
Figure 1O:
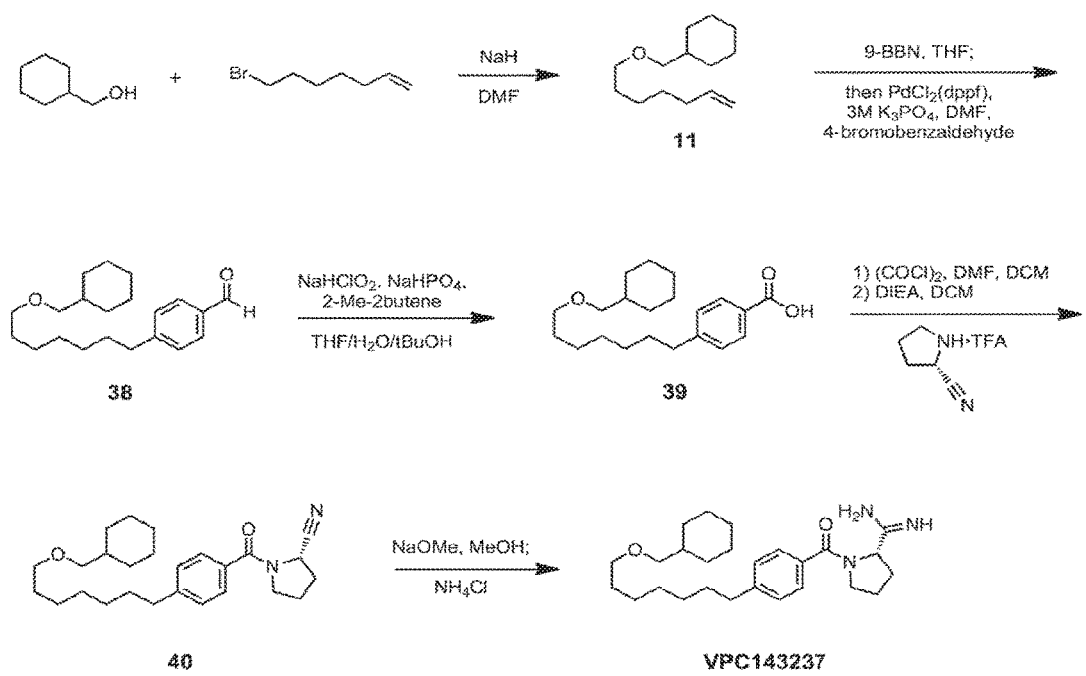
Figure 1P:
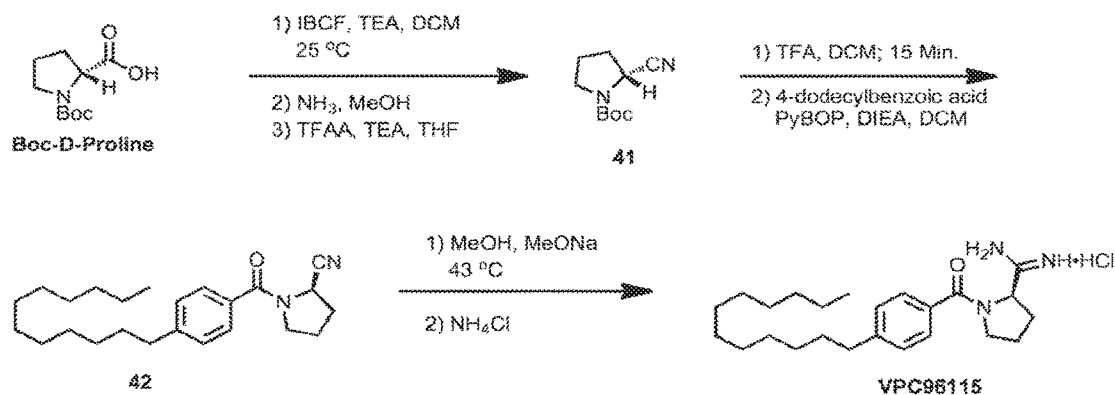
Figure 1Q:
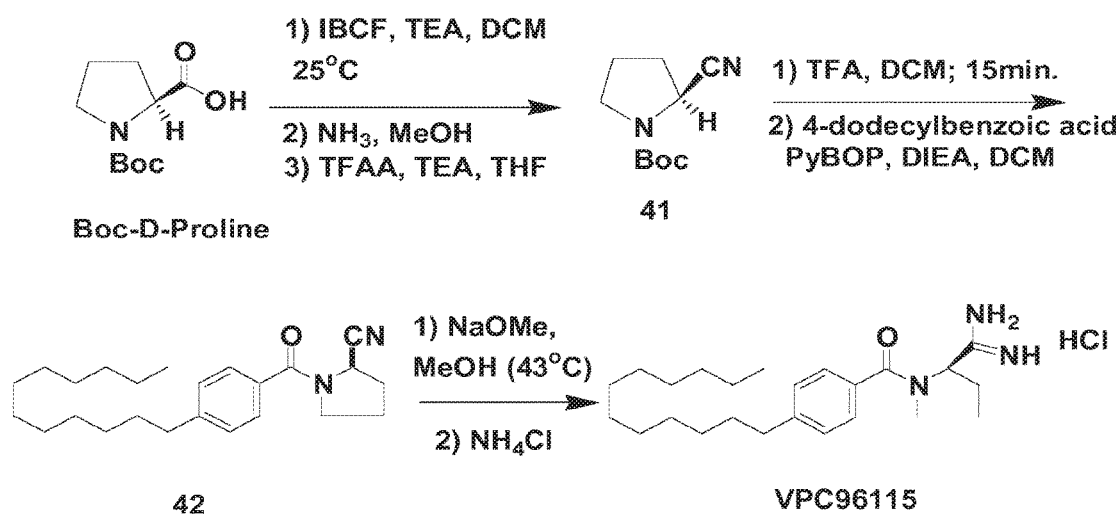
Figure 4A:
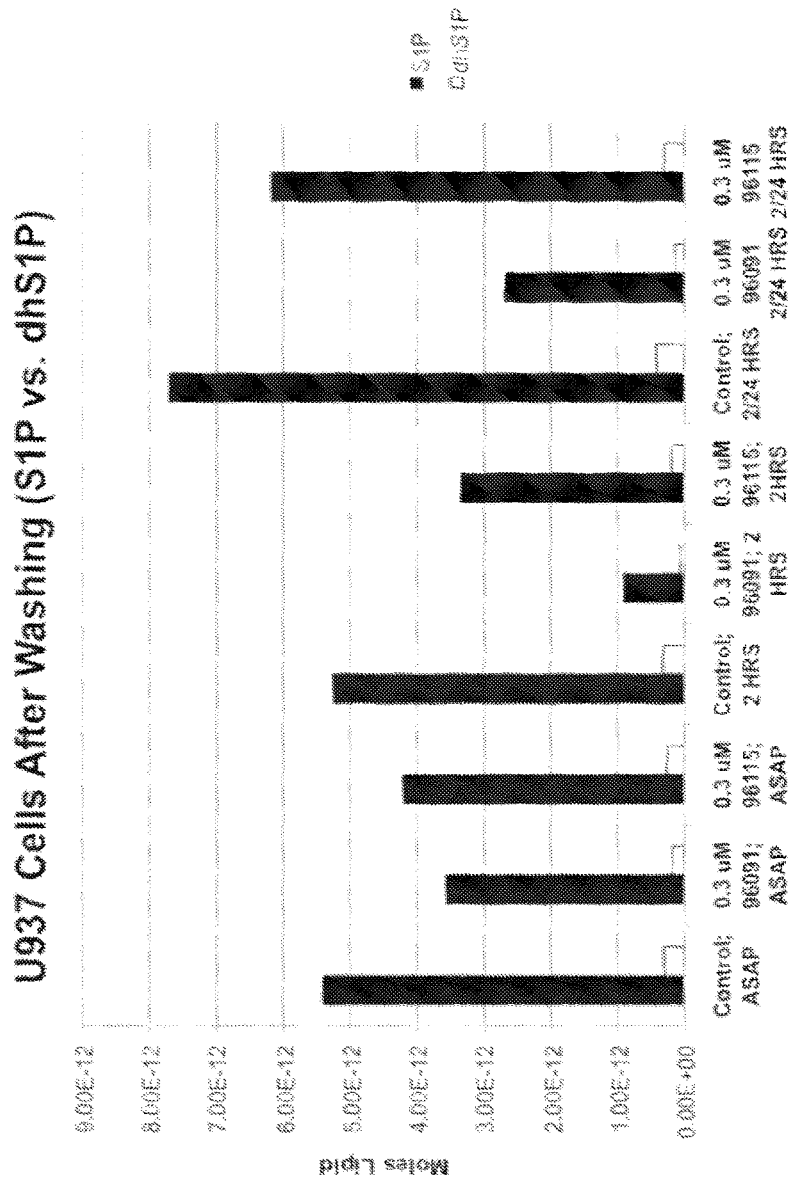
Figure 6A:
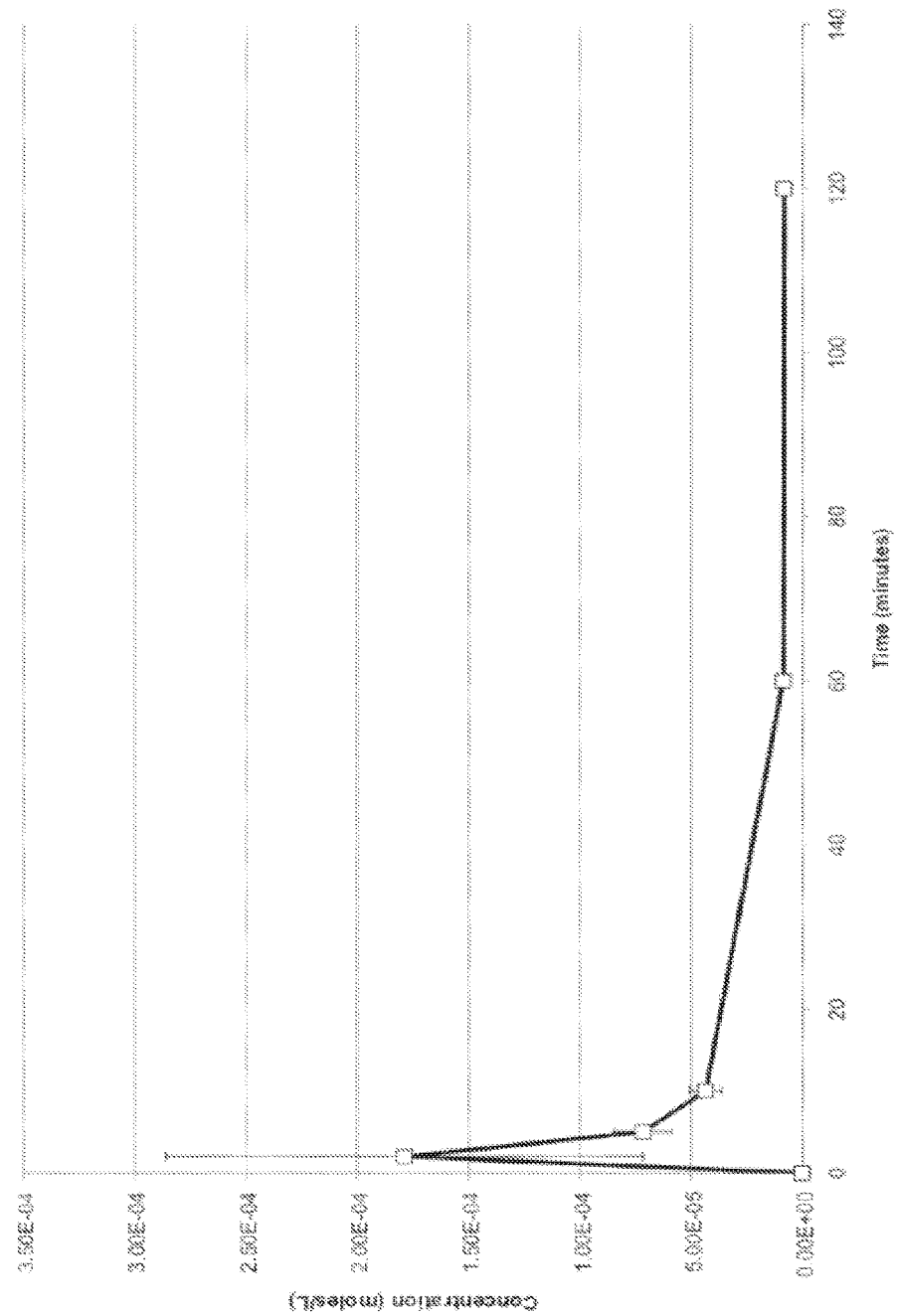
FIG. 6A illustrates the persistence of test compound VPC96091 in whole blood after IV injection of 10 mg/kg (mpk) in rats.
Figure 6B:
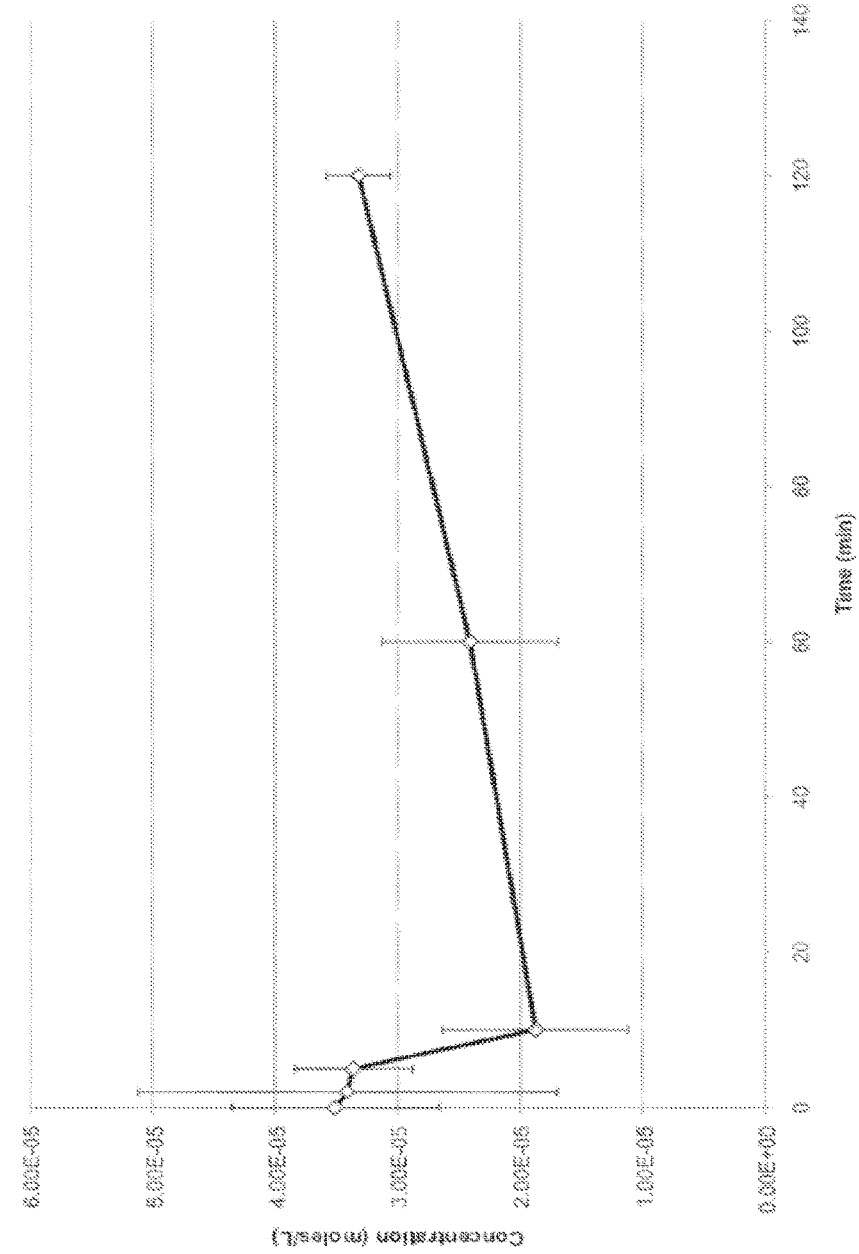
Figure 6D:
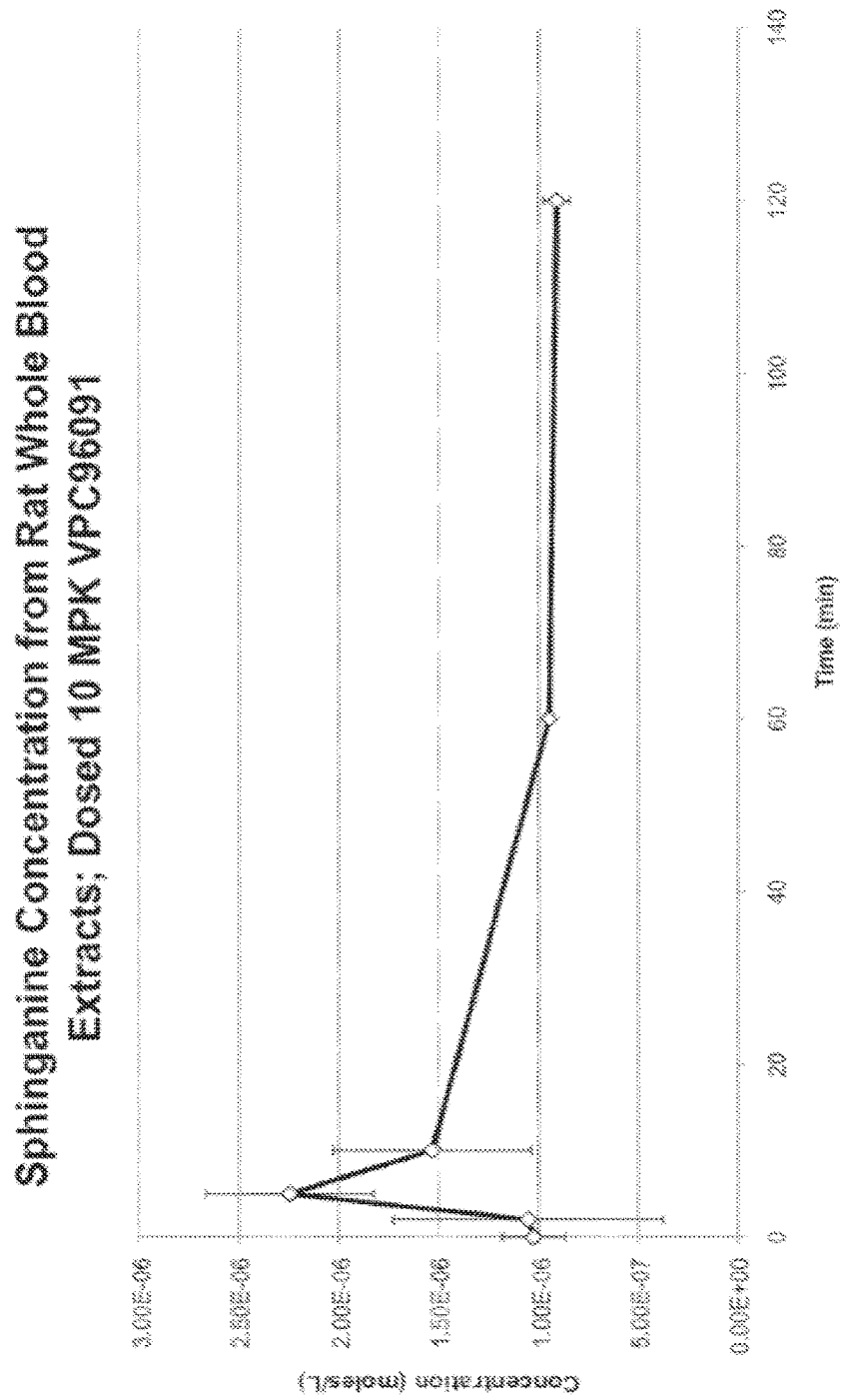
FIGS. 6D and 6E illustrate the inverse change (increase) in levels of enzyme substrates, Sph (6D) or dhSph (6E), in whole rat blood following IV injection of 10 mpk VPC96091.
Figure 6E:
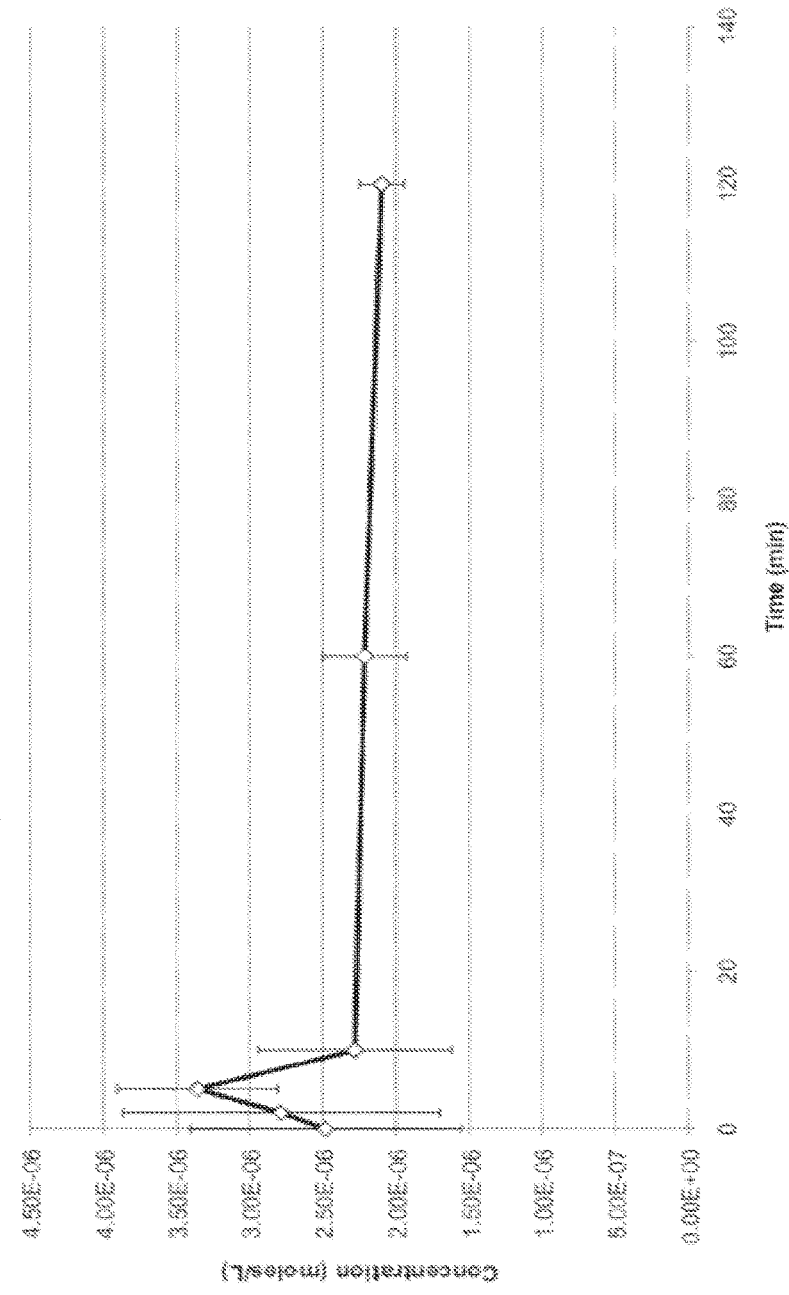

The following abbreviations are used herein: sphingosine kinase (types 1 and 2): SphK, sphingosine 1-phosphate, S1P, and sphinganine 1-phosphate (dhS1P).

In describing and claiming the invention, unless otherwise defined, all technical and scientific terms used herein have the same meaning as commonly understood by one of ordinary skill in the art to which this invention belongs. Although any materials and methods similar or equivalent to those described herein can be used in the practice or testing of the present invention, the preferred materials and methods are described herein. Each of the following terms has meaning associated with it in this section. Exemplary and preferred values listed below for radicals, substituents, and ranges are for illustrations only; they do not exclude other defined values or other values within defined ranges for the radicals and substituents.

The terms "a," "an," "the," "at least one," and "one or more" are used interchangeably. Thus, for example, a composition that comprises "an" element means one element or more than one element.

The term "receptor agonists" are compounds that mimic the action of S1P at one or more of its receptors but may have differing potency and/or efficacy.

The term "receptor antagonists" are compounds that 1) lack intrinsic agonist activity and 2) block agonist (e.g., S1P) activation of the S1P receptor(s), often in a manner that is both fully surmountable and reversible ('competitive antagonist').

The term "affected cell" refers to a cell of a subject afflicted with a disease or disorder, which affected cell has an altered phenotype relative to a subject not afflicted with a disease or disorder.

Cells or tissue are "affected" by a disease or disorder if the cells or tissue have an altered phenotype relative to the same cells or tissue in a subject not afflicted with a disease or disorder.

A disease or disorder is "alleviated" if the severity of a symptom of the disease or disorder, the frequency with which such a symptom is experienced by a patient, or both, is reduced.

An "analog" of a chemical compound is a compound that, by way of example, resembles another in structure but is not necessarily an isomer (e.g., 5-fluorouracil is an analog of thymine).

The terms "cell," "cell line," and "cell culture" may be used interchangeably.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue is obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

A "detectable marker" or a "reporter molecule" is an atom or a molecule that permits the specific detection of a compound having the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" means an amount sufficient to produce a selected effect. For example, an effective amount of an S1P receptor antagonist is an amount that decreases the cell signaling activity of the S1P receptor.

A "functional" molecule is a molecule in a form in which it exhibits a property by which it is characterized. By way of example, a functional enzyme is one which exhibits the characteristic catalytic activity by which the enzyme is characterized.

The term "inhibit" refers to the ability of a disclosed compound to reduce or impede a described function. Inhibition is by at least 10%, preferably by at least 25%, more preferably by at least 50%, even more preferably by at least 75%, and most preferably, the function is inhibited by at least 95%.

The term "selective" refers to the ability of the disclosed compounds to inhibit one of the sphingosine kinase 1 or sphingosine kinase 2 (SphK1 & SphK2) enzymes and not the other enzyme. Preferably, the selective compound will have a Ki value for one enzyme that is less than, by at least an order of magnitude (e.g., a ten-fold difference), the Ki value for the other enzyme or in inhibition of one of the SphK enzymes over the other enzyme.

An "effective amount" means an amount sufficient to produce a selected effect. For example, an effective amount of a sphingosine kinase 1 or sphingosine kinase 2 (SphK1 & SphK2) inhibitor is an amount that inhibits substrate (sphingosine) binding of the sphingosine kinases and thereby the conversion of sphingosine to S1P.

A "functional" molecule is a molecule in a form in which it exhibits a property by which it is characterized. By way of example, a functional enzyme is one that exhibits the characteristic catalytic activity by which the enzyme is characterized.

The term "inhibit" refers to the ability of a disclosed compound to reduce or impede a described function. Inhibition is by at least 10%, preferably by at least 25%, more preferably by at least 50%, even more preferably by at least 75%, and most preferably, the function is inhibited by at least 95%.

The term "instructional material" includes a publication, a recording, a diagram, or any other medium of expression that can be used to communicate the usefulness of the disclosed compounds in the kit for effecting alleviation of the various diseases or disorders recited herein. Optionally, or alternately, the instructional material may describe one or more methods of alleviating the diseases or disorders in a cell or a tissue of a mammal. The instructional material of the kit may, for example, be affixed to a container which contains a disclosed compound or be shipped together with a container which contains the identified compound. Alternatively, the instructional material may be shipped separately from the container with the intention that the instructional material and the compound be used cooperatively by the recipient.

The term "parenteral" means not through the alimentary canal but by some other route such as subcutaneous, intramuscular, intraspinal, or intravenous.

The term "purified" and similar terms relate to the isolation of a molecule or compound in a form that is substantially free (at least 75% free, preferably 90% free, and most preferably at least 95% free) from other components normally associated with the molecule or compound in a native environment. The term "purified" does not necessarily indicate that complete purity of the particular molecules achieved during the process. A "very pure" compound refers to a compound that is greater than 90% pure. A "highly purified" compound refers to a compound that is greater than 95% pure.

A "sample" refers preferably to a biological sample from a subject, including, but not limited to, normal tissue samples, diseased tissue samples, biopsies, blood, saliva, feces, semen, tears, and urine. A sample can also be any other source of material obtained from a subject, which contains cells, tissues, or fluid of interest. A sample can also be obtained from cell or tissue culture.

The term "standard," refers to something used for comparison. For example, a standard can be a known standard agent or compound which is administered or added to a control sample and used for comparing results when measuring said compound in a test sample. Standard can also refer to an "internal standard", such as an agent or compound which is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term "treating" includes prophylaxis of the specific disorder or condition, or alleviation of the symptoms associated with a specific disorder or condition or preventing or eliminating said symptoms.

The disclosed compounds are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours, "r.t." for room temperature, "THF" for tetrahydrofuran, and "rac" for racemic mixture).

The values listed below for radicals, substituents, and ranges, are for illustration only; they do not exclude other defined values or other values within defined ranges for the radicals and substituents. The disclosed compounds include compounds of Formula IA having any combination of the exemplary values, preferred values, and more preferred values described herein.

The term "halogen" or "halo" includes bromo, chloro, fluoro, and iodo. The term "haloalkyl", refers to an alkyl radical bearing at least one halogen substituent, non-limiting examples include, but are not limited to, chloromethyl, fluoroethyl or trifluoromethyl and the like. The term "$C_1$-$C_{20}$ alkyl" refers to a branched or linear alkyl group having from one to twenty carbons. Non-limiting examples include, but are not limited to, methyl, ethyl, n-propyl, iso-propyl, butyl, iso-butyl, sec-butyl, tert-butyl, pentyl, hexyl, heptyl, octyl and the like. The term "$C_2$-$C_{20}$ alkenyl", refers to an olefinically unsaturated branched or linear group having from two to twenty carbon atoms and at least one double bond. Typically, $C_2$-$C_{20}$ alkenyl groups include, but are not limited to, 1-propenyl, 2-propenyl, 1,3-butadienyl, 1-butenyl, hexenyl, pentenyl, hexenyl, heptenyl, octenyl and the like. The term ($C_2$-$C_{20}$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl, and the like. The term "($C_1$-$C_{20}$)alkoxy" refers to an alkyl group attached through an oxygen atom. Examples of ($C_1$-$C_{20}$)alkoxy can be methoxy, ethoxy, propoxy, isopropoxy, butoxy, iso-butoxy, sec-butoxy, pentoxy, 3-pentoxy, hexyloxy, heptoxy, or octoxy, and the like. The term ($C_2$-$C_{26}$)alkoxyalkyl can be methoxy methyl, methoxy ethyl, ethoxy methyl, ethoxy ethyl, and the like.

The term "$C_3$-$C_{12}$ cycloalkyl" includes groups having one ring or multiple rings. Non-limiting examples include be cyclopropyl, cyclobutyl, cyclopentyl, cyclohexyl, cycloheptyl, cyclooctyl, adamantyl and the like.

The term "optionally substituted" refers to zero, one, two, three, four, five, six or seven substituents, wherein the substituents are each independently selected. Each of the independently selected substituents may be the same or different than other substituents. Non-limiting examples of the substituents include halo, halo($C_1$-$C_{10}$)alkyl, cyano, amino (—NR$^a$R$^b$), ($C_1$-$C_{20}$)alkoxy, ($C_2$-$C_{26}$)alkoxyalkyl, ($C_3$-$C_{12}$)cycloalkyl, ($C_6$-$C_{10}$)aryl, ($C_7$-$C_{30}$)alkylaryl, ($C_2$-$C_{10}$)heterocyclic, or ($C_4$-$C_{10}$)-heteroaryl; wherein one or more of the carbon atoms in the Z alkyl groups can be independently replaced with non-peroxide oxygen, sulfur or NR$^c$; where each R$^a$, R$^b$, or R$^c$ is independently hydrogen or ($C_1$-$C_7$)alkyl.

The term "($C_6$-$C_{14}$)aryl" refers to a mono or bicyclic carbocyclic ring system having one or two aromatic rings including, but not limited to, phenyl, benzyl, naphthyl, tetrahydronaphthyl, indanyl, indenyl, and the like.

The term "optionally substituted aryl" includes aryl compounds having zero, one, two, three or four substituents, and a substituted aryl includes aryl compounds having one, two, three or four substituents, wherein the substituents include groups such as, for example, alkyl, halo, amino or those substituents listed herein.

The term "($C_6$-$C_{14}$)aryl($C_1$-$C_{20}$)alkyl", "($C_7$-$C_{30}$)arylalkyl" or "aralkyl" refers to an alkyl group substituted with a mono or bicyclic carbocyclic ring system having one or two aromatic rings including, a group such as phenyl, naphthyl, tetrahydronaphthyl, indanyl, indenyl, and the like. Non-limiting examples of arylalkyl include benzyl, phenyl ethyl, and the like.

The term "($C_2$-$C_{10}$)heterocyclic group" refers to an optionally substituted mono- or bicyclic carbocyclic ring system containing one, two, or three heteroatoms (optionally in each ring) wherein the heteroatoms are non-peroxide oxygen, sulfur, and nitrogen (NR).

The term "($C_4$-$C_{10}$)heteroaryl" refers to an optionally substituted mono- or bicyclic carbocyclic ring system containing one, two, or three heteroatoms (optionally in each ring) wherein the heteroatoms are non-peroxide oxygen, sulfur, and nitrogen (NR$^c$). Non-limiting examples of heteroaryl groups include furyl, thienyl, pyridyl, and the like.

The term "bicyclic" represents either an unsaturated or saturated stable bridged or fused bicyclic carbon ring. The bicyclic ring may be attached at any carbon atom which affords a stable structure. Typically a bicyclic ring system can have from about 7 to about 12 atoms in the ring system. The term includes, but is not limited to, naphthyl, dicyclohexyl, dicyclohexenyl, and the like.

A "derivative" of a compound refers to a chemical compound that may be produced from another compound of similar structure in one or more steps, such as replacement of hydrogen by an alkyl, acyl, or amino group.

The term "pharmaceutically acceptable carrier" includes any of the standard pharmaceutical carriers, such as a phosphate buffered saline solution, hydroxypropyl beta-cyclodextrins (HO-propyl beta cyclodextrins), water, emulsions such as an oil/water or water/oil emulsion, and various types of wetting agents. The term also encompasses any of the agents approved by a regulatory agency of the U.S. Federal government or listed in the US Pharmacopeia for use in animals, including humans.

The term "pharmaceutically-acceptable salt" refers to salts which retain the biological effectiveness and properties of the disclosed compounds and which are not biologically or otherwise undesirable. In many cases, the disclosed compounds are capable of forming acid or base salts by virtue of the presence of amino or carboxyl groups or groups similar thereto.

An "effective amount" means an amount sufficient to produce a selected effect. For example, an effective amount of an S1P receptor agonist is an amount that decreases the cell signaling activity of the S1P receptor.

The disclosed compounds can contain one or more asymmetric centers in the molecule. In accordance with the present disclosure any structure that does not designate the stereochemistry is to be understood as embracing all the various optical isomers, as well as racemic mixtures thereof.

The disclosed compounds may exist in tautomeric forms and the invention includes both mixtures and separate individual tautomers. For example, the following structure:

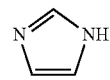

is understood to represent a mixture of the structures:

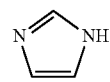

as well as

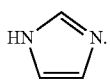

The terms 16:0, 18:0, 18:1, 20:4 or 22:6 hydrocarbon refers to a branched or straight alkyl or alkenyl group, wherein the first integer represents the total number of carbons in the group and the second integer represent the number of double bonds in the group.

The disclosed compounds can contain one or more asymmetric centers in the molecule. In accordance with the present disclosure any structure that does not designate the stereochemistry is to be understood as embracing all the various optical isomers, as well as racemic mixtures thereof.

It will be appreciated by those skilled in the art that the disclosed compounds having chiral centers may exist in and be isolated in optically active and racemic forms. It is to be understood that the disclosed compounds encompass any racemic, optically active or stereoisomeric form, or mixtures thereof, of the compound, which possess the useful properties described herein, such as the S,R; S,S; R,R; or R,S diastereomers. It is well known in the art how to prepare such optically active forms (for example, resolution of the racemic form by recrystallization techniques, synthesis from optically-active starting materials, chiral synthesis, or by chromatographic separation using a chiral stationary phase) and how to determine sphingosine kinase activity using the standard tests described herein, or using other similar tests which are well known in the art. In addition, some compounds may exhibit polymorphism.

Potential uses of SphK inhibitors include, but are not limited to, anti-angiogenesis, treating neoplastic disease, preventing restenosis, treating autoimmune disorders and treating vascular injury.

The compounds of Formula IA are useful for treating a disease or disorder including administering to a subject in need thereof of a therapeutically acceptable amount of a compound of Formula IA, or a pharmaceutical composition comprising a therapeutically effective amount of a compound of Formula IA, and a pharmaceutically-acceptable carrier.

The disclosed compounds are directed to improved SphK inhibiting compounds and derivatives thereof, where, for example, the compounds have been modified to enhance their oral availability and thus increase their efficacy in oral pharmaceutical formulations. The compounds of the present invention are believed to act as inhibitors of SphK enzymes. More particularly, the pro-drug derivatives, amidoximes of the present invention hydroxy derivatives that have enhanced oral availability relative to the parent compound. As shown herein the amidoximes (administered orally) can be reduced to amidines by cells and tissues.

Exemplary and preferred values listed below for radicals, substituents, and ranges, are for illustration only; they do not exclude other defined values or other values within defined ranges for the radicals and substituents.

Exemplary values for $R^1$, hydrogen, or hydroxy.

Exemplary values for $R^2$ and $R^3$ are independently hydrogen, methyl, or ethyl.

Additional exemplary values for $R^2$ and $R^3$ are hydrogen.

Exemplary values for X and Y are independently NH and C=O.

Additional exemplary values for X and Y together are —C(=O)NR$^8$— or —NR$^c$(=O)—.

Exemplary values for R include hydrogen, methyl, ethyl, propyl or isopropyl.

Additional exemplary values for $R^4$ and $R^5$ together with the atom to which they are attached include cyclopropyl, cyclobutyl, cyclopentyl, or cyclohexyl.

Additional exemplary values for $R^4$ and $R^5$ together with the atom to which they are attached include cyclopropyl.

Exemplary values for $R^4$ and $R^8$ together with the atom to which they are attached include cyclopentyl, cyclohexyl or pyrrolidinyl.

Additional exemplary values for $R^4$ and $R^8$ together with the atom to which they are attached include pyrrolidinyl.

Exemplary values for Z include $(C_{10}$-$C_{18})$alkyl, $(C_{10}$-$C_{18})$alkenyl, or $(C_7$-$C_{18})$alkylphenyl.

Additional exemplary values for Z include compounds where the alkyl chain in the alkylphenyl group has 9, 10, 11, 12, 13, 14, 15, or 16, carbon atoms.

Additional exemplary values for Z include $(C_5$-$C_{17})$alkylphenyl,

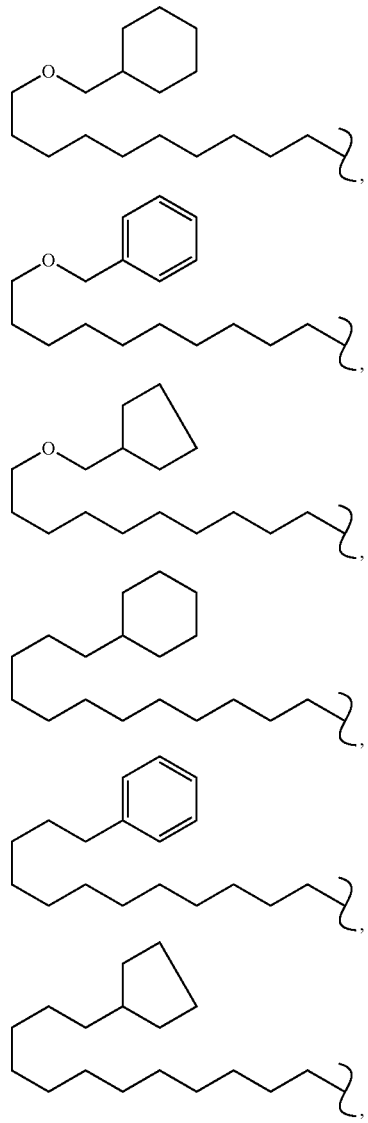

-continued

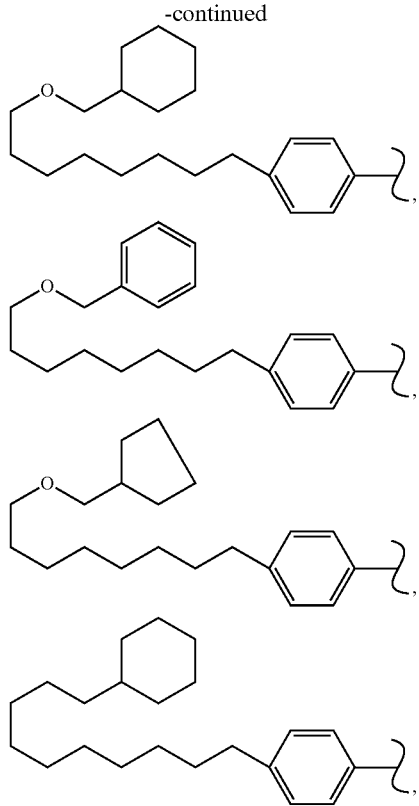

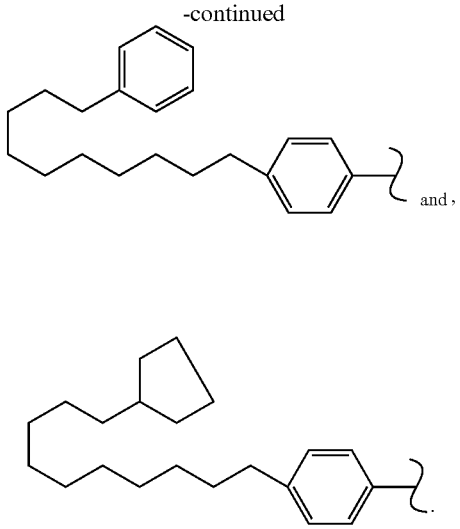

and,

Exemplary heteroatom groups for replacing carbon atoms in a ring or alkyl include O or $NR^{10}$.

Exemplary values for $R^{10}$ include hydrogen, methyl, ethyl, propyl or isopropyl.

Exemplary compounds of the invention have formulas shown in table 1 or salts thereof (the compounds are shown as amidoximes or hydrochloride salts of the claimed compounds). Table 1 includes: Inhibitory constants (Ki) of test compounds, all values in micromolar concentrations. ND not determined

TABLE 1

| Amidine No. | Amidoxime | Amidine (HCl salt) | SphK1 (μM) | SphK2 (μM) |
|---|---|---|---|---|
| VPC96031 | | | 25 | 23 |
| VPC95287 | | | 5 | 4 |
| VPC96047 | | | 0.2 | 0.5 |
| VPC96021 | | | 10 | 32 |
| VPC96055 | | | 36 | 10 |
| VPC171117 | | | >100 | 90 |

TABLE 1-continued

| Amidine No. | Amidoxime | Amidine (HCl salt) | SphK1 (μM) | SphK2 (μM) |
|---|---|---|---|---|
| VPC171147 | | | 60 | 20 |
| VPC171159 | | | NA | NA |
| VPC171167 | | | 4 | 10 |
| VPC171137 | | | 40 | 45 |
| VPC143033 | | | 3 | 4 |
| VPC143081 | | | 0.4 | 5 |

TABLE 1-continued

| Amidine No. | Amidoxime | Amidine (HCl salt) | SphK1 (μM) | SphK2 (μM) |
|---|---|---|---|---|
| VPC143064 | | | 0.3 | 6 |
| VPC143065 | | | 8.4 | >100 |
| VPC143066 | | | 30 | >100 |
| VPC143078 | | | 5 | 38 |
| VPC143129 | | | 0.5 | >10 |

TABLE 1-continued
| Amidine No. | Amidoxime | Amidine (HCl salt) | SphK1 (μM) | SphK2 (μM) |
|---|---|---|---|---|
| VPC143119 | 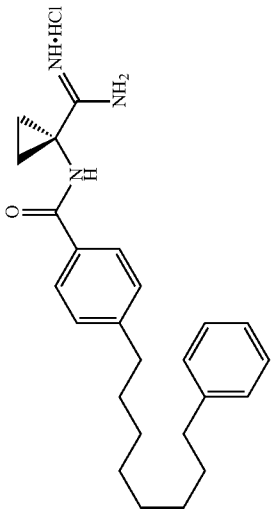 | 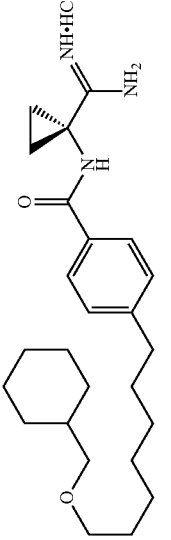 | 1.3 | >10 |
| VPC143113 | 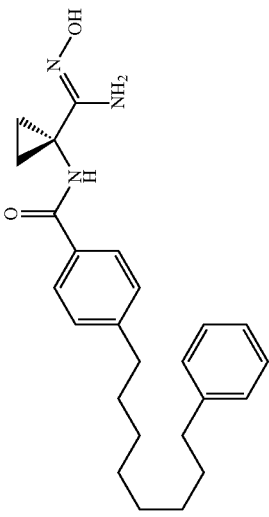 | 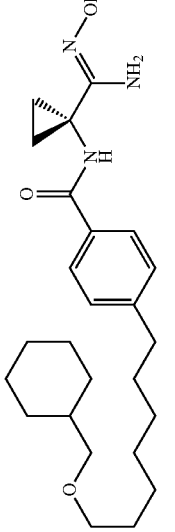 | 0.39 | 12 |
| VPC143105 | 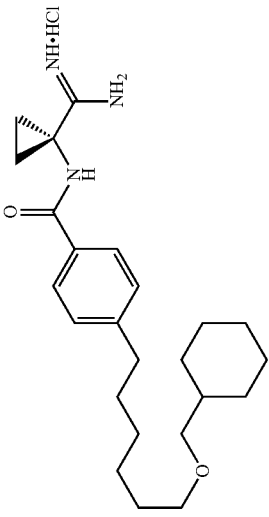 | 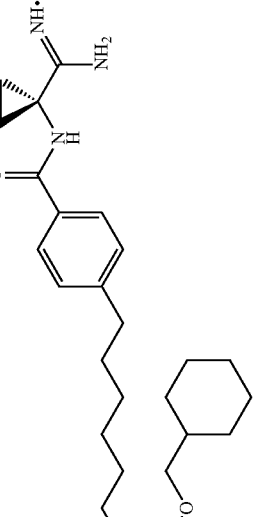 | 0.24 | 7 |
| VPC143126 | 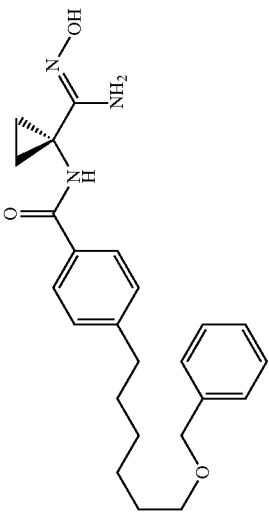 | 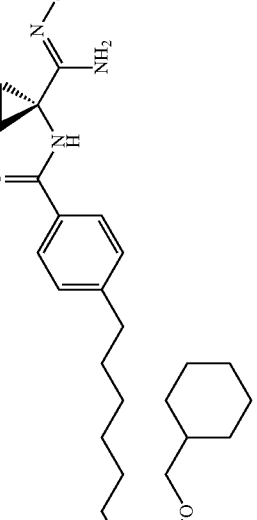 | 0.8 | >20 |

TABLE 1-continued

| Amidine No. | Amidoxime | Amidine (HCl salt) | SphK1 (μM) | SphK2 (μM) |
|---|---|---|---|---|
| VPC143144 | | | 0.11 | 26 |
| VPC14a1058 | | | 0.45 | 25 |
| VPC143154 | | | 0.17 | 18 |
| VPC14a1051 | | | 0.13 | 15 |
| VPC143090 | | | 1.5 | 4.6 |

TABLE 1-continued

| Amidine No. | Amidoxime | Amidine (HCl salt) | SphK1 (μM) | SphK2 (μM) |
|---|---|---|---|---|
| VPC143057 | | | 6 | 7.5 |
| VPC143046 | | | 5.4 | >100 |
| VPC14a1002 | | | 9 | >100 |
| VPC95291 | | | 0.75 | 2.6 |
| VPC95301 | | | 8 | 50 |
| VPC95127 | | | >100 | 60 |

TABLE 1-continued

| Amidine No. | Amidoxime | Amidine (HCl salt) | SphK1 (µM) | SphK2 (µM) |
|---|---|---|---|---|
| VPC95297 | | | 5 | 4 |
| VPC96077 | | | 0.3 | 2 |
| VPC96091 | | | 0.1 | 1.5 |
| VPC96115 | | | 16 | 5 |
| VPC143237 | | | 0.075 | 15 |

TABLE 1-continued

| Amidine No. | Amidoxime | Amidine (HCl salt) | SphK1 (μM) | SphK2 (μM) |
|---|---|---|---|---|
| VPC143v47 | (structure) | (structure) | NA | NA |
| VPC143v48 | (structure) | (structure) | NA | NA |

Pharmaceutically acceptable base addition salts can be prepared from inorganic and organic bases. Salts from inorganic bases, include but are not limited to, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included are amines where the two or three substituents, together with the amino nitrogen, form a heterocyclic or heteroaryl group. Mon-limiting examples of amines include, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful, for example, carboxylic acid amides, including carboxamides, lower alkyl carboxamides, dialkyl carboxamides, and the like.

In cases where compounds of Formula IA are sufficiently basic or acidic to form stable nontoxic acid or base salts, preparation and administration of the compounds, as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Inorganic salts may also be formed, including hydrochloride, sulfate, nitrate, bicarbonate, and carbonate salts.

The compounds of the formulas above include all enantiomers thereof.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of Formula IA can be formulated as pharmaceutical compositions and administered to a mammalian host, such as a human patient in a variety of forms adapted to the chosen route of administration, e.g., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Exemplary solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of Formula IA to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of Formula IA can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of Formula IA in a liquid composition, such as a lotion, will be from about 0.1 to about 25 weight percent, preferably from about 0.5-10 weight percent. The concentration in a semi-solid or solid composition such as a gel or a powder will be about 0.1-5 weight percent preferably about 0.5-2.5 weight percent based on the total weight of the composition.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed method includes a kit comprising an inhibitor compound of Formula IA and instructional material that describes administering the inhibitor compound or a composition comprising the inhibitor compound to a cell or a subject. This should be construed to include other embodiments of kits that are known to those skilled in the art, such as a kit comprising a (preferably sterile) solvent for dissolving or suspending the inhibitor compound or composition prior to administering the compound or composition to a cell or a subject. Preferably, the subject is a human.

The disclosed compounds and methods, as described above or as discussed in the Examples below, there can be employed conventional chemical, cellular, histochemical, biochemical, molecular biology, microbiology, and in vivo techniques, which are known to those of skill in the art. Such techniques are explained fully in the literature.

Without further description, it is believed that one of ordinary skill in the art can, using the preceding description and the following illustrative examples, make and utilize the disclosed compounds.

In another aspect the invention provides compounds having the formula IB:

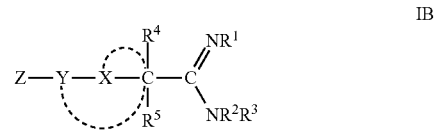

Wherein:
$R^1$ is H or OH;
$R^2$ and $R^3$ are independently H, $(C_1-C_4)$alky; or halo$(C_1-C_3)$alkyl;
$R^4$ is absent, H, $NH_2$ or $(C_1-C_4)$alkyl;
$R^5$ is absent, H or $(C_1-C_4)$alkyl;
or $R^4R^5$ together are $CH_2$—$CH_2$ (cyclopropyl), $CH_2$—$CH_2$—$CH_2$ (cyclobutyl), $CH_2$—$CH_2$—$CH_2$—$CH_2$ (cyclopentyl) or $CH_2$—$CH_2$—$CH_2$—$CH_2$—$CH_2$ (cyclohexyl);
X and Y are independently $CR^6R^7$, $NR^8$, O, S or C=O (carbonyl);
$R^6$ and $R^7$ are independently H or $(C_1-C_7)$alkyl
$R^8$ is H or $(C_1-C_7)$alkyl or $R^6$ and $R^7$ together, or $R^8$ are $(C_2-C_4)$ forming ring structures as shown;

Z is $(C_{10}-C_{20})$alkyl, $(C_{10}-C_{20})$alkenyl, $(C_{10}-C_{20})$alkynyl, $(C_{10}-C_{20})$alkoxy, $(C_{10}-C_{26})$alkoxyalkyl, $(C_{10}-C_{12})$cycloalkyl, $(C_6-C_{10})$aryl, $(C_6-C_{20})$alkylaryl, $(C_6-C_{20})$alkoxylaryl $(C_7-C_{30})$arylalkyl, $(C_2-C_{10})$heterocyclic, $(C_4-C_{10})$heteroaryl, or $(C_4-C_{10})$heteroaryl$(C_1-C_{20})$alkyl.

The invention includes pharmaceutically acceptable salts or esters of the compounds of Formula IB.

Processes for preparing compounds of Formula IA or for preparing intermediates useful for preparing compounds of Formula IA are provided as further embodiments. Intermediates useful for preparing compounds of Formula IA are also provided as further embodiments. The processes are provided as further embodiments and are illustrated in the schemes herein wherein the meanings of the generic radicals are as given above unless otherwise qualified.

Processes for preparing compounds of Formula IA or for preparing intermediates useful for preparing compounds of Formula IA are provided as further embodiments of the invention. Intermediates useful for preparing compounds of Formula IA are also provided as further embodiments of the invention. The compounds of the invention can be prepared using starting materials and methods known in the art.

The invention is now described with reference to the following Examples and Embodiments. Without further description, it is believed that one of ordinary skill in the art can, using the preceding description and the following illustrative examples, make and utilize the disclosed compounds. The following working examples therefore, are provided for the purpose of illustration only and specifically point out the preferred embodiments, and are not to be construed as limiting in any way the remainder of the disclosure. Therefore, the examples should be construed to encompass any and all variations which become evident as a result of the teaching provided herein.

Examples—Materials and Methods

The following abbreviations are used throughout specific and general experimental procedures: acetonitrile (MeCN), acetic acid (AcOH), chloroform ($CHCl_3$), ethyl acetate (EtOAc), iso-propanol (i-PrOH), methanol (MeOH), trifluoroacetic acid (TFA), water ($H_2O$), hydrochloric acid (HCl), sodium sulfate ($Na_2SO_4$), sodium carbonate ($Na_2CO_3$), sodium bicarbonate ($NaHCO_3$), Magnesium Sulfate ($MgSO_4$), potassium carbonate ($K_2CO_3$), phosphorus pentoxide ($P_2O_5$), lithium hydroxide (LiOH), aqueous (aq.), hour (h), minute (min), room temperature (r.t.).

Except as indicated otherwise, reactions were monitored by thin layer chromatography (TLC) using 0.25 mm Whatman precoated silica gel plates. Flash chromatography was performed with the indicated solvents and Dynamic Adsorbents silica gel (particle size 0.023-0.040 mm).

All non-aqueous reactions were carried out in oven or flame-dried glassware under an argon or nitrogen atmosphere with dry solvents and magnetic stirring, unless otherwise stated. The argon and nitrogen were dried by passing through a tube of Drierite. Anhydrous diethyl ether ($Et_2O$), toluene, dichloromethane ($CH_2Cl_2$), methanol (MeOH), and tetrahydrofuran (THF) and N,N-dimethylformamide (DMF) were purchased from Aldrich or VMR Chemicals and used as received. THF was dried over activated molecular sieves (4 Å) prior to use. All other reagents were purchased from Acros chemicals and Aldrich chemicals.

Except as indicated otherwise, reactions were monitored by thin layer chromatography (TLC) using 0.25 mm Whatman precoated silica gel plates. Flash chromatography was performed with the indicated solvents and Dynamic Adsorbents silica gel (particle size 0.023-0.040 mm).

Proton ($^1H$) and carbon ($^{13}C$) NMR spectra were recorded on a Varian UnityInova 500/51 or Varian UnityInova 300/54 at 300K unless otherwise noted. Chemical shifts are reported in ppm (δ) values relative to the solvent as follows: $CDCl_3$ (δ 7.24 for proton and δ 77.0 for carbon NMR), DMSO-$d_6$ (δ 2.50 for proton and δ 39.5 for carbon NMR) $CD_3OD$ (δ 3.31 for proton and δ 47.6 for carbon NMR).

High performance liquid chromatography—mass spectrometry (LCMS) was carried out on a Waters 2695 separations module and a Finnigan LCQ series mass spectrometer. All compounds were evaluated for purity using a Thompson Instrument Company Advantage $C_{18}$ column. Columns were outfitted with 5 μM beads with a 60 Å pore size; columns were 250 mm in length and 4.6 mm in diameter. Mobile phase A consisted of HPLC grade $H_2O$ and 0.01% TFA; mobile phase B consisted of MeCN and 0.01% TFA. LCMS identification and purity utilized a binary gradient starting with 90% A and 10% B and linearly increasing to 100% B over the course of 10 minutes, followed by and isocratic flow of 100% B for an additional 10 minutes. A flow rate of 1 mL/min. was maintained throughout the HPLC method. The purity of all products was determined by integration of the total ion count (TIC) spectra and integration of the ultraviolet (UV) spectra at 214 nm; a Waters 486 Tunable Absorbance Detector was used to collect all UV data. Retention times are abbreviated as $t_R$; mass to charge ratios are abbreviated as m/z.

General Experimental Procedures

General Procedure A: Schotten-Baumen Protection of Free Amino Acids

To a stirring solution of 10% sodium carbonate (weight to volume) in water (25 mL) was added the free amino acid (9.3 mmol). To this solution was added either di-tert-butyl dicarbonate or N-(Benzyloxycarbonyloxy)succinamide (18.6 mmol) followed by 1,4-dioxanes (18.6 mL). This solution was allowed to stir for approximately 15 hours at which point the reaction mixture was extracted with three 15 mL portions of diethyl ether. The aqueous layer was then acidified to a pH of 3 and immediately extracted with four to five 25 mL portions of ethyl acetate. The organic layers were then combined and washed with a 10 mL portion of brine, dried with $MgSO_4$, and evaporated to dryness. The crude material was immediately taken on with no further purification.

General Procedure B: Conversion of a Carboxylic Acid to a Primary Amide

To the stirring solution of the carboxylic acid (9.3 mmol) in 20 mL of DCM was added triethylamine (3.76 g). After cooling the solution to −25° C., iso-butylchloroformate (2.54 g) was added dropwise to the mixture. This mixture was stirred for approximately 45 minutes and analyzed by TLC. Upon completion of the reaction, 3.5 mL of a 28% solution of ammonium hydroxide in water was added to the reaction mixture (still at −25° C.) and stirred for an additional 30 minutes. After this time the mixture was warmed to r.t. and stirred for an additional 15 hours at this temperature. When the reaction was deemed complete by TLC, the reaction mixture was evaporated to an aqueous solution, diluted with 150 mL of EtOAc and extracted with four 15 mL portions of de-ionized water. The organic layer was washed once with brine, dried over $MgSO_4$ and evaporated to dryness. The crude mixture was taken on without further purification.

General Procedure C: Conversion of a Primary Amide to a Nitrile

The primary amide (9.3 mmol) and triethylamine (1.9 g) was taken up in 93 mL of anhydrous THF and cooled to 0° C. Upon cooling, trifluoroacetic anhydride (2.34 g) was added drop-wise to the reaction mixture; after 10 minutes of stirring at this low temperature the reaction mixture was allowed to warm to ambient temperature and evaporated to dryness. The crude organic mixture was taken up in 200 mL of EtOAc and extracted with four 15 mL portions of 1N HCl followed by one 10 mL portion of brine. The organic layer was then dried of $MgSO_4$ and evaporated to an oil. The crude product was purified by flash chromatography and identified by NMR analysis.

General Procedure D: De-Protection of N-Boc Protected Amino-Nitriles

To a stirring solution of the N-Boc protected amino-nitrile (1.2 mmol) in anhydrous DCM (12 mL) was added trifluoroacetic acid, drop-wise (12 mL) at room temperature. After 15 minutes the reaction mixture was evaporated to dryness. Three 5 mL portions of methanol were added to the crude oil and evaporated immediately; three 5 mL portions of diethyl ether were then added and evaporated in the same fashion to provide the trifluoroacetate salt as either a yellowish solid or oil, depending on the substrate. This salt was carried on immediately in the same reaction vessel.

General Procedure E: PyBOP Mediated Couplings of HCl or TFA Salts to Acids

To a suspension of either the HCl or TFA salt of an amine (0.43 mmols) in anhydrous DCM (9 mL) was added the acid (0.43 mmols) and PyBOP (0.223 g). Finally, diisopropylethylamine (0.222 g) was added and the reaction was allowed to stir for 15 hours. At this time the reaction mixture was evaporated to dryness and reconstituted in 100 mLs of EtOAc. The solution was extracted with four 15 mL portions of 1N HCl followed by one portion of brine. The organic layer was dried with $MgSO_4$ and evaporated to dryness. The crude organic material was purified by flash chromatography.

General Procedure F: Amide Formation from an Amine and an Acid Chloride

To a solution of a primary amine salt (1.68 mmol) in DCM (17 mLs) stirring at 0° C. was added diisopropylethyl amine (5.04 mmol) followed by an acid chloride (2.184 mmols). The reaction mixture was allowed to warm to ambient temperature slowly and stirred for an additional 15 hours. At this time the reaction mixture was evaporated to dryness and reconstituted in ethyl acetate (150 mLs). The solution was next extracted with three 15 mL equivalents of 1N HCl followed by one 15 mL equivalent of brine. The organic layer was then dried with magnesium sulfate, filtered through a fritted funnel and dried to an oil. The crude mixture was purified via flash chromatography.

General Procedure G: Conversion of Carboxylic Acids to Acid Chlorides

An acid (0.28 mmols) and a catalytic amount of dimethylformamide were dissolved in dichloromethane (2.8 mLs) and the solution was cooled to 0° C. To this solution was added oxalyl chloride (0.84 mmols) and the reaction mixture was warmed to room temperature. After stirring for 2 hours, the reaction mixture was evaporated to dryness; the crude material was taken up in 3 one mL portions of diethyl ether and evaporated. The oil was dried under vacuum for an additional 30 minutes and carried on.

General Procedure H: Direct Conversion of Nitriles to Amidines

A nitrile (0.21 mmols) was taken up in 2.1 mL of anhydrous methanol and 42 μL of a solution of 0.5 M sodium methoxide in methanol was immediately added. This mixture was allowed to stir for 15 hours at which time 0.231 mmols of ammonium chloride was added to the reaction. When the reaction appeared complete by TLC, the product was purified in one of two ways. The reaction mixture was evaporated to dryness and the crude material was taken up in chloroform and filtered through a fine fritted funnel. The eluent was collected and thoroughly dried under vacuum. Then the reaction mixture was taken up in $Et_2O$ and filtered again through a fine fritted funnel; the product was recovered as a white or off-white solid.

General Procedure I: Pinnick Oxidation of Aldehydes to Carboxylic Acids

An aryl aldehyde (3.05 mmol) was taken up in a 78 mL solution of 1:1 THF and tert-butyl alcohol followed by 1.71 g of 2-methyl-2-butene. In a separate flask 0.83 g of sodium chlorite and 1.26 g of sodium phosphate monobasic were dissolved in 13 mL of $H_2O$. Once fully dissolved, the aqueous solution was poured into the stirring organic solution and stirred vigorously. Upon completion by TLC, the reaction mixture was evaporated to dryness and reconstituted in 100 mLs of EtOAc. The organic solution was extracted with three 15 mL portions of 1N HCl followed by a single 10 mL portion of brine. The organic layer was finally dried over magnesium sulfate and evaporated to dryness. No further purification was necessary.

General Procedure J: Ether Synthesis from an Alkylbromide and an Alcohol

To a solution of an alcohol (13.12 mmol) in DMF (40 mL) at 0° C. was added 60% NaH in mineral oil (13.12 mmol) and let stir at that temperature for 45 min. The alkyl bromide (6.56 mmol) was then added and the reaction let to warm in the ice bath for 12 hours. The reaction was then cooled to 0° C. and slowly quenched with 1N HCl. The mixture was then extracted into three 200 mL portions ethyl acetate, dried with $Na_2SO_4$, and concentrated to a yellow oil. The title product was recovered after purification by flash chromatography.

General Procedure K: Ether Synthesis from an Alkyl Bromide and a Phenol

A phenol (8.2 mmols), alkyl bromide (12.3 mmols) and cesium carbonate (16.4 mmols) were dissolved in 14.4 mL of DMF. The reaction mixture was then heated to 80° C. until the starting phenol appeared consumed via TLC analysis. After this time, the reaction mixture was diluted with 200 mL of EtOAc and the solution was washed with eight 10 mL portions of $H_2O$ and two 10 mL portions of brine. The organic layer was then dried over $MgSO_4$ and evaporated to dryness. The title product was recovered in quantitative yield after purification by flash chromatography.

General Procedure L: Organocuprate Substitution of an Alkylbromide

To a solution of cuprous chloride (0.33 mmol) in $Et_2O$ (7 mL) at −78° C. was added a 2.0M solution BnMgBr in THF (13.1 mmol) followed by an alkyl bromide (6.52 mmol) and let warm to r.t. After reacting at r.t. for 20 hours, the reaction was cooled to 0° C. and quenched with 1 n HCl. The mixture was then extracted into three 200 mL portions ethyl acetate, dried with $Na_2SO_4$, and concentrated to a black oil. The title product was recovered after purification by flash chromatography.

General Procedure M: Hydroboration and Suzuki Coupling of an Olefin and Arylbromide An aryl aldehyde (3.05 mmol) was taken up in a 78 mL solution of 1:1 THF and tert-butyl alcohol followed by 1.71 g of 2-methyl-2-butene. In a separate flask 0.83 g of sodium chlorite and 1.26 g of sodium phosphate monobasic were dissolved in 13 mL of $H_2O$. Once fully dissolved, the aqueous solution was poured into the stirring organic solution and stirred vigorously. Upon completion by TLC, the reaction mixture was evaporated to dryness and reconstituted in 100 mLs of EtOAc. The organic solution was extracted with three 15 mL portions of 1N HCl followed by a single 10 mL portion of brine. The organic layer was finally dried over magnesium sulfate and evaporated to dryness. No further purification was necessary.

(Alternate Pathway for Hydroboration and Suzuki Coupling of an Olefin and Arylbromide.)

To a solution of alkene (4.52 mmol) in THF (23 mL) at r.t. was added a 0.5 M solution of 9-BBN (18 mL) and let stir for 12 hrs. 3 M $K_3PO_4$ (3 mL) was then added to the reaction and let stir for 10 mins. The reaction was then diluted with DMF (23 mL) followed by the addition of the aryl bromide (4.97 mmol) then $PdCl_2(dppf)$ (0.23 mmol) and let stir at r.t. for 6 hrs. The reaction was then extracted into three 200 mL portions ethyl acetate, dried with $Na_2SO_4$, and concentrated to a black oil. The product was recovered after purification by flash chromatography.

General Procedure N: Zinc Mediated Reduction of a Nitrobenzene to an Aniline

To a solution of a nitrobenzene (2.00 mmol) in AcOH (10 mL) at r.t. was added Zn dust by solid addition and let stir for 12 hrs. The reaction was then diluted with ethyl acetate and filtered through a pad of Celite™. The filtrate was evaporated to dryness and the product was recovered after purification by flash chromatography.

General Procedure O: Hydroboration/Oxidation of a Terminal Olefin to an Alcohol

To a solution of an alkene (4.3 mmol) in dry THF (2.9 mL) at 0° C. was added 9-BBN (0.5 M in THF, 9.4 mL, 4.7 mmol). The reaction was immediately brought to room temperature and allowed to react for 2 hours. Upon total consumption of starting alkene the solution cooled down to −5° C. and charged with EtOH (2.7 mL), 3 N NaOH (1.4 mL) and 30% $H_2O_2$ (1.5 mL). The reaction was brought immediately to room temperature and allowed to stir for 2 h. The reaction is then diluted with EtOAc and washed with 1 N HCl. The organic layer was dried with $Na_2SO_4$, filtered and concentrated to a crude oil. Crude material was subjected to flash chromatography.

General Procedure P: Azide Formation from a Primary Alcohol

To a solution of an alcohol (876 mg, 3.2 mmol) in DCM (32 mL) at 0° C. was added triethylamine (4.8 mmol) dropwise followed by methanesulfonyl chloride (3.5 mmol) dropwise. Reaction was immediately brought to room temperature and allowed to react for 2 hours. Upon consumption of starting material by TLC reaction is evaporated and reconstituted in EtOAc. Crude solution is filtered through silica gel and eluent is concentrated. Crude material is diluted in DMF (32 mL) and $NaN_3$ is added (32 mmol). Reaction is heated to 100° C. and allowed to react overnight. The reaction was quenched by the slow addition of brine and then diluted with EtOAc. The organic layer was washed with brine, dried, with $Na_2SO_4$, filtered and concentrated to a crude oil. Crude material was subjected to flash chromatography.

General Procedure Q: Azide Reduction to an Amine

To a solution of an azide (1.2 mmol) in EtOAc (12 mL) at room temperature was added palladium on carbon (0.1 mmol) and reaction fitted with a hydrogen balloon (1 atm). Reaction was allowed to stir for 24 hours. Reaction is diluted with EtOAc and filtered through a plug of Celite and concentrated. Crude material is diluted in DMF (12 mL) and chilled to 0° C. 1-cyano-1-cyclopropanecarboxylic acid (266 mg, 0.86 mmol), PyBOP (1.87 g, 3.6 mmol), and diisopropylethylamine (627 µL, 3.6 mmol) are added. The reaction is allowed to warm to room temperature overnight. The reaction was quenched by the slow addition of brine and then diluted with EtOAc. The organic layer was washed with brine, dried, with $Na_2SO_4$, filtered and concentrated to a crude oil. Crude material was subjected to flash chromatography.

Synthesis of Specific Intermediates (S)—N-(1-cyanoethyl)oleamide (1)

General procedures D was used to deprotect 1.17 mmols of (S)-tert-butyl 1-cyanoethylcarbamate to the corresponding amine. General procedure F was then use to couple to amine to 1.521 mmols of oleoyl chloride. After standard purification techniques, 0.62 mmols (53%) of the title product was recovered. $^1H$ NMR (500 MHz, $CDCl_3$) δ 6.08 (s, 1H), 5.40-5.28 (m, 2H), 5.00-4.90 (m, 1H), 4.12 (q, J=7.2, OH), 2.20 (dd, J=6.6, 8.5, 2H), 2.00 (dd, J=6.3, 12.0, 4H), 1.68-1.58 (m, 2H), 1.54 (d, J=7.2, 3H), 1.38-1.20 (m, 24H), 0.87 (t, J=6.9, 3H). $^{13}C$ NMR (126 MHz, $CDCl_3$) δ 172.49, 130.02, 129.66, 119.35, 36.11, 35.63, 31.88, 29.74, 29.68, 29.50, 29.31, 29.20, 29.14, 29.08, 27.20, 27.14, 25.30, 22.67, 19.43, 14.11.

N-(1-cyanocyclopropyl)-4-decylbenzamide (3)

General procedure E was used to couple 1.68 mmols of 1-amino-cyclpropanecarbonitrile and 1.68 mmols of 4-decylbenzoic acid. The reaction mixture was heated to 50° C. for 48 hours; after this time standard purification techniques were used to recover 0.84 mmols (50%) of the title product. $^1H$ NMR (500 MHz, $CDCl_3$) δ 7.70 (dd, J=3.2, 8.1, 2H), 7.21 (d, J=8.0, 2H), 2.66-2.58 (m, 2H), 1.59 (d, J=5.6, 4H), 1.36 (q, J=5.8, 2H), 1.32-1.20 (m, 15H), 0.87 (t, J=6.9, 3H). $^{13}C$ NMR (126 MHz, $CDCl_3$) δ 168.16, 148.04, 129.96, 128.74, 127.32, 120.30, 35.86, 31.88, 31.15, 29.59, 29.45, 29.31, 29.23, 22.67, 20.88, 16.91, 14.12.

VPC95287

General procedure H was used to convert 0.12 mmols of 3 to the title product. After standard purification techniques, 0.02 mmols (17%) of the title product was recovered and submitted for biological evaluation. $^1H$ NMR (500 MHz, $CD_3OD$) δ 7.81 (d, J=6.1, 2H), 7.30 (d, J=6.3, 2H), 2.67 (t, J=6.7, 2H), 1.75 (s, 2H), 1.63 (s, 2H), 1.56 (s, 2H), 1.29 (d, J=20.9, 14H), 0.89 (dd, J=4.5, 7.0, 3H). $^{13}C$ NMR (126 MHz, $CD_3OD$) δ 172.51, 169.93, 147.78, 130.20, 128.34, 128.04, 127.48, 35.32, 32.59, 31.63, 30.97, 29.27, 28.81, 28.66, 22.30, 18.15, 12.98. $t_R$=10.34 min.; m/z=344.5.

N-(1-cyanocyclopropyl)-4-octylbenzamide (4-C8)

General procedure G was used to convert 0.53 mmols of 4-octylbenzoic acid to an acid chloride. After standard purification techniques, the acyl-chloride was isolated in quantitative yield and carried on immediately. General procedure F was used to couple 0.41 mmols of 1-amino-1- cyclopropanecarbonitrile to 0.53 mmols of the acid chloride. Standard purification techniques were used to isolate 0.21 mmols (51%) of the title product. $^1$H NMR (500 MHz, CDCl$_3$) δ 7.74-7.67 (m, 2H), 7.21 (d, J=8.4, 2H), 7.12 (s, 1H), 2.68-2.58 (m, 2H), 1.59 (dd, J=5.8, 8.3, 4H), 1.35 (dd, J=5.9, 8.3, 2H), 1.33-1.21 (m, 10H), 0.87 (t, J=7.0, 3H). $^{13}$C NMR (126 MHz, CDCl$_3$) δ 168.06, 148.02, 129.96, 128.73, 127.27, 120.23, 35.85, 31.83, 31.13, 29.39, 29.21, 22.63, 20.88, 16.91, 14.08.

VPC96031

General procedure H was used to convert 0.17 mmols of 4-C8 to the corresponding amidine. After standard purification techniques, 0.04 mmols (24%) of the title product were recovered. $^1$H NMR (500 MHz, CD$_3$OD) δ 7.82 (d, J=8.3, 2H), 7.30 (d, J=8.2, 2H), 2.76-2.62 (m, 2H), 1.75 (dd, J=5.9, 8.5, 2H), 1.64 (dd, J=7.1, 14.3, 2H), 1.56 (dd, J=6.1, 8.4, 2H), 1.29 (dd, J=7.1, 15.0, 11H), 0.89 (t, J=7.0, 3H). $^{13}$C NMR (126 MHz, CD$_3$OD) δ 172.52, 169.94, 147.79, 130.21, 128.19, 127.47, 35.32, 32.59, 31.58, 30.98, 29.11, 28.97, 28.82, 22.29, 18.16, 12.99. LCMS: t$_R$=8.5 minutes; m/z=316.

N-(1-cyanocyclopropyl)-4-dodecylbenzamide
(4-C12)

General procedure G was used to convert 4-dodecylbenzoic acid (0.52 mmols) to the corresponding acyl chloride. After standard work up procedures, the intermediate was immediately subjected to conditions described in general procedure F in the presence of 1-amino-1-cyclopropanecarbonitrile hydrochloride (0.4 mmols). After flash chromatography, 0.15 mmols of the title product was recovered. $^1$H NMR (500 MHz, CDCl$_3$) δ 7.68 (d, J=7.1, 2H), 7.23 (d, J=7.5, 2H), 6.82 (s, 1H), 2.63 (t, J=7.7, 2H), 1.65-1.57 (m, 4H), 1.35 (t, J=7.0, 2H), 1.29-1.25 (m, 17H), 0.88 (t, J=6.5, 3H). $^{13}$C NMR (126 MHz, CDCl$_3$) δ 167.81, 148.06, 130.01, 128.75, 127.19, 120.07, 35.85, 31.89, 31.11, 29.61, 29.53, 29.42, 29.32, 29.20, 22.66, 20.88, 16.97, 14.08.

VPC96047.

General procedure H was used to convert 4-C12 (0.15 mmols) to the corresponding amidine. Upon previously described recrystallization procedures 0.06 mmols (40%) of the title product was recovered. $^1$H NMR (500 MHz, DMSO) δ 9.08 (s, 1H), 8.66 (bs, 4H), 7.81 (d, J=6.7, 2H), 7.27 (d, J=6.9, 2H), 2.60 (s, 2H), 1.65 (s, 2H), 1.54 (s, 2H), 1.37 (s, 2H), 1.21 (s, 19H), 0.83 (s, 3H). $^{13}$C NMR (126 MHz, DMSO) δ 172.22, 167.99, 147.01, 131.21, 128.45, 128.32, 35.38, 33.09, 31.74, 31.23, 29.45, 29.27, 29.16, 28.98, 22.54, 18.42, 14.42. LCMS: t$_R$=10.85 minutes; m/z=372.

N-(1-cyanocyclopropyl)-4-tetradecylbenzamide
(4-C14)

General procedure G was used to convert 0.61 mmols of 4-tetradecylbenzoic acid to an acid chloride. After standard purification techniques, the acyl-chloride was isolated in quantitative yield and immediately. General procedure F was used to couple 0.47 mmols of 1-amino-1-cyclopropanecarbonitrile. After standard purification techniques, 0.28 mmols (60%) of the title product was recovered. $^1$H NMR (300 MHz, CDCl$_3$) δ 7.68 (d, J=8.2, 2H), 7.23 (d, J=8.2, 2H), 6.85 (s, 1H), 2.63 (t, J=9, 2H); 1.64-1.55 (m, 4H), 1.35 (dd, J=5.8, 8.5, 2H), 1.25 (s, 20H), 0.87 (t, J=6.6, 3H). $^{13}$C NMR (75 MHz, CDCl$_3$) δ 168.05, 148.30, 130.19, 128.98, 127.43, 120.32, 36.09, 32.15, 31.38, 29.88, 29.68, 29.58, 29.45, 22.92, 21.10, 17.20, 14.36.

VPC96021

General procedure H was used to convert 0.26 mmols of 4-C14 to the title product. After standard purification techniques, 0.04 mmols (15%) of product was recovered and submitted for biological evaluation. $^1$H NMR (500 MHz, DMSO) δ 9.04 (s, 1H), 8.61 (bs, 4H), 7.81 (d, J=7.8, 2H), 7.27 (d, J=5.8, 2H), 2.60 (t, J=7.1, 2H), 1.65 (s, 2H), 1.54 (d, J=5.5, 2H), 1.37 (s, 2H), 1.24-1.21 (m, 21H), 0.83 (t, J=6.5, 3H). $^{13}$C NMR (126 MHz, DMSO) δ 172.23, 168.02, 147.03, 131.24, 128.45, 128.31, 127.93, 35.38, 33.12, 31.72, 31.20, 29.44, 29.25, 29.13, 28.98, 22.52, 18.40, 14.39. LCMS: t$_R$=12.3 minutes; m/z=400.

N-(1-cyanocloproyl)-4-hexadecylbenzamide
(4-C16)

General procedure G was used to convert hexadecanoic acid (0.58 mmols) to the corresponding acyl chloride. After standard work up techniques, the intermediated was coupled to 1-amino-1-cyclopropanecarbonitrile hydrochloride using the methods described in general procedure F. Upon flash chromatography 0.41 mmols of the title product was recovered. $^1$H NMR (500 MHz, CDCl$_3$) δ 7.68 (d, J=8.2, 2H), 7.23 (d, J=8.1, 2H), 6.81 (s, 1H), 2.63 (t, J=7.7, 3H), 1.64-1.58 (m, 4H), 1.35 (q, J=4.9, 2H), 1.33-1.21 (m, 27H), 0.88 (t, J=6.9, 3H). $^{13}$C NMR (126 MHz, CDCl$_3$) δ 167.79, 148.06, 130.01, 128.75, 127.19, 120.07, 97.26, 35.84, 31.90, 31.11, 29.66, 29.63, 29.54, 29.43, 29.33, 29.20, 22.67, 20.88, 16.96, 14.08.

VPC96055

General procedure H was used to convert 0.18 mmols of 16-C16 to the corresponding amidine. However, instead of methanol, ethanol was used to solubilize the starting material. After standard recrystallization techniques, 0.04 mmols (22%) of the title product was recovered as a white solid. $^1$H NMR (500 MHz, DMSO) δ 9.06 (s, 1H), 8.65 (bs, 4H), 7.81 (d, J=7.5, 2H), 7.27 (d, J=7.5, 2H), 2.67-2.56 (m, 2H), 1.65 (s, 2H), 1.54 (d, J=4.0, 2H), 1.37 (s, 2H), 1.21 (bs, 25H), 0.84 (t, J=5.4, 3H). $^{13}$C NMR (126 MHz, DMSO) δ 172.16, 168.01, 147.02, 131.21, 128.45, 128.31, 35.38, 33.11, 31.74, 31.24, 29.46, 29.27, 29.15, 28.99, 22.54, 18.41, 14.42. LCMS: t$_R$=12.4; m/z=428.

4-(heptyloxy)benzaldehyde (5-C7)

General procedure K was used to convert 4-hydroxybenzaldehyde (8.2 mmols) and 1-bromoheptane (12.3 mmols) to 6.6 mmols (80%) of the title product was recovered. $^1$H NMR (300 MHz, CDCl$_3$) δ 9.87 (s, 1H), 7.82 (d, J=8.8 Hz, 2H), 6.99 (d, J=8.7 Hz, 2H), 4.03 (t, J=6.5 Hz, 2H), 1.81 (quin., J=6 Hz, 1H), 1.24-1.53 (m, 8H), 0.89 (t, J=6.8 Hz, 3H); $^{13}$C NMR (75 MHz, CDCl$_3$) δ 191.0, 164.4, 132.13, 129.8, 114.9, 68.6, 31.9, 29.18, 29.1, 26.1, 22.7, 14.2.

4-(heptyloxy)benzoic acid (6-C7)

General procedure I was used to convert 5-C7 (1.5 g, 6.6 mmol) to 6-C7 (1.6 g, 6.6 mmol, 100%) $^1$H NMR (300 MHz, DMSO-d$_6$) δ 7.87 (d, J=8.7 Hz, 2H), 6.99 (d, J=8.8 Hz, 2H), 4.01 (t, J=6.4 Hz, 2H), 1.71 (quin., J=6.5 Hz, 2H), 1.47-1.19 (m, 4H), 0.86 (t, J=6.5 Hz, 3H); $^{13}$C NMR (75 MHz, DMSO-d$_6$) δ 167.0, 162.3, 131.3, 122.8, 114.17, 67.8, 31.2, 28.5, 28.4, 25.4, 22.0, 13.9.

N-(1-cyanocyclopropyl)-4-(heptyloxy)benzamide
(7-C7)

General procedure G was used to convert 1.00 mmols of 6-C7 to an acid chloride. After standard purification techniques, the acyl-chloride was isolated in quantitative yield and immediately. General procedure F was used to couple 0.84 mmols of 1-amino-1-cyclopropanecarbonitrile. After standard purification techniques, 0.20 mmols (24%) of the title product was recovered. $^1$H NMR (300 MHz, CDCl$_3$) δ 7.77 (d, J=8.8 Hz, 2H), 6.85 (d, J=8.8 Hz, 2H), 3.94 (t, J=6.5 Hz, 2H), 1.76 (quin., J=5 Hz, 2H), 1.53 (t, J=5.7 Hz, 2H), 1.25-1.45 (m, 8H), 0.88 (t, J=6.7 Hz, 3H); $^{13}$C NMR (75 MHz, CDCl$_3$) δ 168.2, 162.6, 129.4, 124.6, 120.7, 114.4, 68.3, 31.8, 29.8, 29.2, 29.1, 26.0, 22.7, 21.0, 16.88, 14.2.
VPC171117

General procedure H was used to convert 0.20 mmols of 7-C7 to the title product. After standard purification techniques, 0.13 mmols (65%) of product was recovered and submitted for biological evaluation. $^1$H NMR (500 MHz, CD$_3$OD) δ7.87 (d, J=8.6 Hz, 2H), 6.98 (d, J=8.7 Hz, 2H), 4.04 (t, J=6.4 Hz, 2H), 1.84-1.71 (m, 4H), 1.56 (bs, 2H), 1.52-1.43 (quin., J=7.5 Hz, 2H), 1.41-1.32 (m, 6H), 0.92 (t, J=6.8 Hz, 3H); $^{13}$C NMR (125 MHz, CD$_3$OD) δ 174.0, 170.9, 164.0, 130.8, 126.1, 115.20, 69.3, 34.0, 33.0, 30.3, 30.2, 27.1, 23.7, 19.6, 14.4.

4-(nonyloxy)benzaldehyde (5-C9)

General procedure K was used to convert 4-hydroxybenzaldehyde (8.2 mmols) and 1-bromononane (12.3 mmols) to 6.5 mmols (79%) of the title product was recovered. $^1$H NMR (300 MHz, CDCl$_3$) δ 9.88 (s, 1H), 7.83 (d, J=8.9 Hz, 2H), 6.99 (d, J=8.7 Hz, 2H), 4.04 (t, J=6.6 Hz, 2H), 1.76-1.85 (m, 2H), 1.14-1.53 (m, 12H), 0.88 (t, J=6.6 Hz, 3H); $^{13}$C NMR (75 MHz, CDCl$_3$) δ 164.40, 132.11, 114.86, 68.55, 31.98, 29.47, 29.37, 29.18, 28.90, 28.31, 26.08, 22.79, 14.23.

4-(nonyloxy)benzoic acid (6-C9)

General procedure I was used to convert 5-C9 (1.5 g, 6.5 mmol) to 6-C9 (1.6 g, 6.5 mmol, 100%) $^1$H NMR (300 MHz, DMSO-d$_6$) δ 7.87 (d, J=8.8 Hz, 2H), 6.99 (d, J=8.8 Hz, 2H), 4.02 (t, J=6.5 Hz, 2H), 1.71 (quin., J=6.8 Hz, 2H), 1.48-1.35 (m, 2H), 1.25 (bs, 12H), 0.85 (t, J=6.6 Hz, 3H); $^{13}$C NMR (75 MHz, CDCl$_3$) δ 167.0, 162.3, 131.3, 122.8, 114.2, 67.7, 31.3, 29.0, 28.7, 28.6, 28.5, 25.4, 22.1, 13.9.

N-(1-cyanocyclopropyl)-4-(nonyloxy)benzamide (7-C9)

General procedure G was used to convert 1.00 mmols of 6-C9 to an acid chloride. After standard purification techniques, the acyl-chloride was isolated in quantitative yield and immediately. General procedure F was used to couple 0.84 mmols of 1-amino-1-cyclopropanecarbonitrile. After standard purification techniques, 0.59 mmols (70%) of the title product was recovered. $^1$H NMR (300 MHz, CDCl$_3$) δ 7.71 (d, J=8.9 Hz, 2H), 6.90 (d, J=8.9 Hz, 2H), 3.99 (t, J=6.6 Hz, 2H), 1.79 (quin., J=6 Hz, 1H), 1.61-1.65 (m, 2H), 1.19-1.50 (m, 14H), 0.88 (t, J=6.8 Hz, 1H); $^{13}$C NMR (75 MHz, CDCl$_3$) δ 129.4, 114.7, 95.6, 68.6, 38.0, 32.2, 29.9, 29.6, 29.4, 26.3, 23.0, 17.3, 14.5.
VPC171147

General procedure H was used to convert 0.20 mmols of 7-C9 to the title product. After standard purification techniques, 0.08 mmols (40%) of product was recovered and submitted for biological evaluation. $^1$H NMR (500 MHz, CD$_3$OD) δ 7.88 (d, J=8.6 Hz, 2H), 6.97 (d, J=8.6 Hz, 2H), 4.03 (t, J=6.3 Hz, 2H), 1.78 (m, 4H), 1.56 (bs, 2H), 1.47 (bd, 2H), 1.29 (bs, 8H), 0.90 (t, J=6.7 Hz, 1H); $^{13}$C NMR (125 MHz, CD$_3$OD) δ 164.1, 130.8, 130.5, 126.1, 115.3, 115.2, 69.3, 33.1, 30.7, 30.5, 30.4, 30.3, 27.1, 23.8, 19.6, 17.0, 14.5; t$_R$=10.60 min, (m/z)=347.19.

4-(undecyloxy)benzaldehyde (5-C11)

General procedure K was used to convert 4-hydroxybenzaldehyde (8.2 mmols) and 1-bromononane (12.3 mmols) to 6.5 mmols (79%) of the title product was recovered. $^1$H NMR (300 MHz, CDCl$_3$) δ 9.87 (s, 1H), 7.82 (d, J=8.8 Hz, 2H), 6.99 (d, J=8.8 Hz, 2H), 4.03 (t, J=6.5 Hz, 3H), 1.76-1.87 (m, 2H), 1.26-1.48 (m, 16H), 0.88 (t, J=6.7 Hz, 3H); $^{13}$C NMR (75 MHz, CDCl$_3$) δ 191.0, 164.4, 132.1, 129.8, 114.9, 68.6, 34.3, 33.0, 32.1, 29.7, 29.6, 29.5, 29.2, 29.0, 28.3, 26.1, 22.8, 14.3.

4-(undecyloxy)benzoic acid (6-C11)

General procedure I was used to convert 5-C11 (1.5 g, 6.5 mmol) to 6-C11 (1.6 g, 6.5 mmol, 100%) $^1$H NMR (500 MHz, CDCl$_3$) δ 8.05 (d, J=8.8 Hz, 2H), 6.93 (d, J=8.8 Hz, 2H), 4.02 (t, J=6.6 Hz, 3H), 1.76-1.84 (m, 2H), 1.39-1.50 (m, 2H), 1.19-1.39 (m, 14H), 0.88 (t, J=6.8 Hz, 3H); $^{13}$C NMR (75 MHz, DMSO-d$_6$) δ 167.0, 162.3, 131.3, 122.8, 114.2, 67.7, 31.3, 29.0, 28.7, 28.5, 25.4, 22.1, 13.9.

N-(1-cyanocyclopropyl)-4-(undecyloxy)benzamide (7-C11)

General procedure G was used to convert 1.00 mmols of 6-C1 to an acid chloride. After standard purification techniques, the acyl-chloride was isolated in quantitative yield and immediately. General procedure F was used to couple 0.84 mmols of 1-amino-1-cyclopropanecarbonitrile. After standard purification techniques, 0.27 mmols (32%) of the title product was recovered. $^1$H NMR (500 MHz, CDCl$_3$) δ 7.71 (d, J=8.6 Hz, 2H), 6.90 (d, J=8.6 Hz, 2H), 3.98 (t, J=6.6 Hz, 2H), 1.79 (quin., J=5 Hz, 2H), 1.62 (dd, J=9.1, 6.3 Hz, 2H), 1.45 (quin., J=5 Hz, 2H), 1.35 (dd, J=9.0, 6.1 Hz, 2H), 1.20-1.32 (m, 14H), 0.88 (t, J=6.9 Hz, 3H); $^{13}$C NMR (125 MHz, CDCl$_3$) δ 168.2, 162.8, 129.6, 124.8, 120.8, 114.6, 68.5, 32.2, 29.90, 29.87, 29.68, 29.65, 29.4, 26.3, 23.0, 21.2, 17.2, 14.4.
VPC171167

General procedure H was used to convert 0.20 mmols of 7-C11 to the title product. After standard purification techniques, 0.07 mmols (35%) of product was recovered and submitted for biological evaluation. $^1$H NMR (500 MHz, CD$_3$OD) δ 7.88 (d, J=8.6 Hz, 2H), 6.97 (d, J=8.6 Hz, 2H), 4.03 (t, J=6.3 Hz, 2H), 1.81-1.74 (m, 4H), 1.56 (t, J=6.9 Hz, 2H), 1.47 (quin., J=6.3 Hz, 2H), 1.41-1.21 (m, 14H), 0.90 (t, J=6.7 Hz, 3H); $^{13}$C NMR (125 MHz, CD$_3$OD) δ 174.8, 171.7, 164.9, 131.68, 131.4, 126.9, 116.0, 70.1, 34.9, 33.9, 31.6, 31.4, 31.1, 28.0, 24.6, 20.4, 17.9, 15.3; t$_R$=10.69 min, (m/z)=374.16.

4-(tridecyloxy)benzaldehyde (5-C13)

General procedure K was used to convert 4-hydroxybenzaldehyde (8.2 mmols) and 1-bromononane (12.3 mmols) to 7.3 mmols (87%) of the title product was recovered. $^1$H NMR (300 MHz, CDCl$_3$) δ 9.88 (s, 1H), 7.83 (d, J=8.8 Hz, 2H), 6.99 (d, J=8.7 Hz, 2H), 4.04 (t, J=6.5 Hz, 2H), 1.76-1.88 (m, 2H), 1.52-1.08 (m, 20H), 0.88 (t, J=6.7 Hz, 3H).

4-(tridecyloxy)benzoic acid (6-C13)

General procedure I was used to convert 5-C31 (1.5 g, 7.3 mmol) to 6-C13 (1.6 g, 7.3 mmol, 100%) $^1$H NMR (300

MHz, CDCl₃) δ 7.87 (d, J=8.9 Hz, 2H), 6.98 (d, J=8.9 Hz, 2H), 4.01 (t, J=6.5 Hz, 2H), 1.80-1.71 (m, 2H), 1.49-1.13 (m, 20H), 0.85 (t, J=6.5 Hz, 3H); $^{13}$C NMR (75 MHz, CDCl₃) δ 166.9, 162.2, 131.3, 122.8, 114.1, 67.7, 35.1, 32.2, 31.3, 29.0, 28.9, 28.7, 28.5, 28.1, 27.5, 25.4, 22.1, 13.9.

N-(1-cyanocyclopropyl)-4-(tridecyloxy)benzamide (7-C13)

General procedure G was used to convert 1.00 mmols of 6-C13 to an acid chloride. After standard purification techniques, the acyl-chloride was isolated in quantitative yield and immediately. General procedure F was used to couple 0.84 mmols of 1-amino-1-cyclopropanecarbonitrile. After standard purification techniques, 0.27 mmols (32%) of the title product was recovered. $^1$H NMR (300 MHz, CDCl₃) δ 7.72 (d, J=8.9 Hz, 2H), 6.90 (d, J=8.9 Hz, 2H), 3.98 (t, J=6.6 Hz, 2H), 1.86-1.69 (m, 2H), 1.61 (dd, J=10.0, 7.3 Hz, 2H), 1.51-1.01 (m, 22H), 0.87 (t, J=6.0 Hz, 3H); $^{13}$C NMR (75 MHz, CDCl₃) δ 129.4, 129.3, 114.7, 68.6, 68.5, 51.6, 32.3, 30.0, 29.7, 29.4, 26.3, 17.3.
VPC171137

General procedure H was used to convert 0.20 mmols of 7-C13 to the title product. After standard purification techniques, 0.06 mmols (30%) of product was recovered and submitted for biological evaluation. $^1$H NMR (500 MHz, DMSO-d₆) δ 9.16 (s, 1H), 7.80 (d, J=8.1 Hz, 2H), 6.99 (d, J=8.1 Hz, 2H), 4.01 (t, J=6.3 Hz, 2H), 1.70 (quin., J=5 Hz, 2H), 1.53 (t, J=6.5 Hz, 2H), 1.38 (quin., J=6.5 Hz, 2H), 1.27 (bs, 18H), 0.85 (t, J=6.5 Hz, 3H); $^{13}$C NMR (125 MHz, CD₃OD) δ 167.7, 162.6, 130.3, 125.8, 122.1, 115.0, 68.7, 32.3, 30.0, 29.9, 29.7, 29.5, 26.4, 23.1, 21.3, 16.7, 14.9; $t_R$=11.57 min, (m/z)=402.22.

N-(1-cyanocyclopropyl)palmitamide (8)

General procedure F was used to couple 1.68 mmols of 1-amino-1-cyclopropanecarbonitrile to 2.184 mmols of palmitoyl chloride. After standard purification techniques, 1.3 mmols (77%) of the title product was recovered. $^1$H NMR (500 MHz, CDCl3) δ 5.95 (s, 1H), 2.16 (t, J=7.6, 2H), 1.65-1.59 (m, 2H), 1.58 (s, 1H), 1.57-1.53 (m, 2H), 1.39-1.15 (m, 28H), 0.88 (dd, J=6.0, 7.0, 3H). $^{13}$C NMR (126 MHz, CDCl₃) δ 119.97, 36.08, 31.91, 29.64, 25.17, 22.68, 20.32, 16.85, 14.25.
VPC95291

General procedure H was used to convert 0.18 mmols of 8 to the corresponding amidine. After standard purification techniques, 0.06 mmols (33%) of the title product were recovered. $^1$H NMR (500 MHz, CD₃OD) δ 2.28-2.23 (m, 1H), 2.16 (t, J=7.5, OH), 1.65 (dd, J=6.0, 8.3, 1H), 1.63-1.55 (m, 2H), 1.47 (dd, J=5.7, 8.2, OH), 1.38 (dd, J=6.0, 8.4, 1H), 1.29 (d, J=10.5, 19H), 1.18 (dd, J=5.6, 8.2, 1H), 0.90 (t, J=6.9, 3H). $^{13}$C NMR (126 MHz, CD₃OD) δ 176.72, 172.34, 35.17, 32.02, 31.65, 29.35, 29.33, 29.30, 29.18, 29.05, 29.02, 28.95, 28.91, 28.74, 25.11, 24.79, 22.30, 17.95, 15.39, 13.00. $t_R$=10.84 min.; m/z=339

N-(1-cyanocyclopropyl)oleamide (9)

General procedure F was used to 1.68 mmols of 1-amino-1-cyclopropanecarbonitrile to 2.184 mmols of oleoyl chloride. After standard purification techniques, 1.24 mmols (74%) of the title product was recovered. $^1$H NMR (500 MHz, CDCl₃) δ 6.53 (s, 1H), 5.43-5.25 (m, 2H), 2.17 (t, J=7.6, 2H), 1.99 (dd, J=6.5, 12.5, 4H), 1.60 (d, J=7.2, 2H), 1.52 (dd, J=5.7, 8.3, 2H), 1.39-1.15 (m, 24H), 0.87 (t, J=6.9, 3H). $^{13}$C NMR (126 MHz, CDCl₃) δ 174.09, 130.00, 129.66, 120.14, 97.26, 35.97, 31.88, 29.74, 29.68, 29.51, 29.30, 29.23, 29.14, 29.09, 27.20, 27.14, 25.22, 22.66, 20.39, 16.74, 14.11.
VPC95301

General procedure H was used to convert 0.44 mmols of 13 to the title product. After standard purification techniques, 0.1 mmols (23%) was recovered and submitted for biological evaluation. $t_R$=11.13 min.; m/z=364.31

1-cyano-N-(4-decylphenyl)cyclopropanecarboxamide (10-C10)

General procedure E was used to convert 1.00 mmol of 4-decylanaline to title product; isolated as a white solid, 325 mg (0.99 mmol, 99%): $R_f$=0.52 (20% EtOAc in hexanes); $^1$H NMR (300 MHz, CDCl3) δ 8.16 (s, 1H), 7.41 (d, J=8.4, 2H), 7.14 (d, J=8.4, 2H), 2.73-2.40 (m, 2H), 1.77 (dd, J=4.4, 8.2, 2H), 1.68-1.51 (m, 4H), 1.29 (m, 14H), 0.90 (t, J=6.6, 3H); $^{13}$C NMR (75 MHz, CDCl3) δ 163.54, 140.27, 134.81, 129.13, 120.87, 120.27, 77.83, 77.40, 76.98, 35.63, 32.16, 31.69, 29.86, 29.75, 29.60, 29.49, 22.95, 18.44, 14.39, 14.32.
VPC143033

General procedure H was used to convert 0.99 mmol of 10-C10 to the title product; white solid isolated, 191 mg (0.51 mmol, 51%): $^1$H NMR (500 MHz, DMSO) δ 9.69 (s, 1H), 9.50-8.33 (m, 4H), 7.47 (d, J=8.4, 2H), 7.10 (d, J=8.4, 2H), 2.50 (d, J=7.8, 2H), 1.66-1.34 (m, 6H), 1.22 (m, 14H), 0.83 (t, J=6.9, 3H); $^{13}$C NMR (126 MHz, DMSO) δ 168.27, 166.44, 138.41, 136.53, 128.64, 128.58, 121.33, 121.28, 34.98, 31.73, 31.44, 29.98, 29.45, 29.30, 29.13, 29.02, 22.54, 15.12, 14.41.

1-cyano-N-(4-undecylphenyl)cyclopropanecarboxamide (10-C11)

General procedure E was used to convert 1.00 mmol of 4-undecylanaline to title product; isolated as a white solid, 353 mg (0.99 mmol, 99%): $R_f$=0.56 (20% EtOAc in hexanes); $^1$H NMR (300 MHz, CDCl3) δ 8.11 (s, 1H), 7.40 (d, J=8.4, 2H), 7.15 (d, J=8.4, 2H), 2.76-2.38 (m, 2H), 1.77 (dd, J=4.4, 8.2, 2H), 1.56 (m, J=4.4, 8.2, 4H), 1.27 (m, 18H), 0.89 (t, J=6.6, 3H); $^{13}$C NMR (75 MHz, CDCl3) δ 163.57, 140.34, 134.70, 129.20, 120.80, 120.28, 35.65, 32.19, 31.70, 29.92, 29.76, 29.63, 29.50, 22.95, 18.45, 14.34.
VPC143081

General procedure H was used to convert 0.99 mmol of 10-C11 to the title product; white solid isolated, 183 mg (0.39 mmol, 39%): $^1$H NMR (500 MHz, DMSO) δ 9.69 (s, 1H), 9.50-8.33 (m, 4H), 7.45 (d, J=8.2, 2H), 7.12 (d, J=8.2, 2H), 2.50 (d, J=7.8, 2H), 1.66-1.34 (m, 6H), 1.22 (m, 18H), 0.83 (t, J=6.9, 3H); $^{13}$C NMR (126 MHz, DMSO) δ 168.22, 166.41, 138.46, 136.55, 128.69, 128.53, 121.33, 121.29, 34.98, 31.74, 31.47, 29.99, 29.45, 29.29, 29.13, 29.02, 22.54, 15.16, 14.49.

1-cyano-N-(4-dodecylphenyl)cyclopropanecarboxamide (10)

General procedure E was used to convert 1.00 mmol of 4-dodecylanaline to title product; isolated as a white solid, 353 mg (0.99 mmol, 99%): $R_f$=0.59 (20% EtOAc in hexanes); $^1$H NMR (300 MHz, CDCl3) δ 8.11 (d, J=8.4, 2H), 7.15 (d, J=8.4, 2H), 2.76-2.38 (m, 2H), 1.77 (dd, J=4.4, 8.2, 2H), 1.56 (m, J=4.4, 8.2, 4H), 1.27 (m, 18H), 0.89 (t, J=6.6, 3H); $^{13}$C NMR (75 MHz, CDCl3) δ 163.57, 140.34, 134.70, 129.20, 120.80, 120.28, 35.65, 32.19, 31.70, 29.92, 29.76, 29.63, 29.50, 22.95, 18.45, 14.34.

VPC143064

General procedure H was used to convert 0.99 mmol of 10 to the title product; white solid isolated, 183 mg (0.45 mmol, 45%): $^1$H NMR (500 MHz, DMSO) δ 9.69 (s, 1H), 9.50-8.33 (m, 4H), 7.45 (d, J=8.2, 2H), 7.12 (d, J=8.2, 2H), 2.50 (d, J=7.8, 2H), 1.66-1.34 (m, 6H), 1.22 (m, 18H), 0.83 (t, J=6.9, 3H); $^{13}$C NMR (126 MHz, DMSO) δ 168.22, 166.41, 138.46, 136.55, 128.69, 128.53, 121.33, 121.29, 34.98, 31.74, 31.47, 29.99, 29.45, 29.29, 29.13, 29.02, 22.54, 15.16, 14.49.

1-cyano-N-(4-tetradecylphenyl)cyclopropanecarboxamide (10-C14)

General procedure E was used to convert 1.00 mmol of 4-tetradecylanaline to title product; isolated as a white solid, 381 mg (0.99 mmol, 99%): $R_f$=0.67 (20% EtOAc in hexanes); $^1$H NMR (300 MHz, CDCl3) δ 8.11 (s, 1H), 7.40 (d, J=8.4, 2H), 7.15 (d, J=8.4, 2H), 2.76-2.38 (m, 2H), 1.77 (dd, J=4.4, 8.2, 2H), 1.56 (dd, J=4.4, 8.2, 4H), 1.27 (m, 20H), 0.89 (t, J=6.6, 3H); $^{13}$C NMR (75 MHz, CDCl3) δ 163.54, 140.32, 134.67, 129.24, 120.82, 120.28, 35.62, 32.16, 31.71, 29.92, 29.73, 29.63, 29.54, 22.92, 18.44, 14.31.

VPC143065

General procedure H was used to convert 0.99 mmol of 10-C14 to the title product; white solid isolated, 161 mg (0.37 mmol, 37%): $^1$H NMR (500 MHz, DMSO) δ 9.69 (s, 1H), 9.50-8.33 (m, 4H), 7.45 (d, J=8.2, 2H), 7.12 (d, J=8.2, 2H), 2.50 (d, J=7.8, 2H), 1.66-1.34 (m, 6H), 1.22 (m, 20H), 0.83 (t, J=6.9, 3H); $^{13}$C NMR (126 MHz, DMSO) δ 168.24, 166.43, 138.41, 136.52, 128.67, 128.51, 121.35, 121.29, 34.95, 31.74, 31.47, 29.97, 29.45, 29.30, 29.14, 29.02, 22.54, 15.16, 14.42.

1-cyano-N-(4-hexadecylphenyl)cyclonronanecarboxamide (10-C16)

General procedure E was used to convert 1.00 mmol of 4-hexadecylanaline to title product; isolated as a white solid, 409 mg (0.99 mmol, 99%): $R_f$=0.85 (20% EtOAc in hexanes); $^1$H NMR (300 MHz, CDCl3) δ 8.14 (s, 1H), 7.40 (d, J=8.4, 2H), 7.14 (d, J=8.4, 2H), 2.78-2.44 (m, 2H), 1.77 (dd, J=4.4, 8.2, 2H), 1.56 (dd, J=4.4, 8.2, 4H), 1.27 (m, 22H), 0.89 (t, J=6.7, 3H); $^{13}$C NMR (75 MHz, CDCl3) δ 163.50, 140.29, 134.78, 129.14, 120.83, 120.27, 35.63, 32.19, 31.71, 29.95, 29.77, 29.64, 29.51, 22.96, 18.44, 14.40.

VPC143066

General procedure H was used to convert 0.99 mmol of 10-C16 to the title product; white solid isolated, 125 mg (0.27 mmol, 27%): $^1$H NMR (500 MHz, DMSO) δ 9.69 (s, 1H), 9.50-8.33 (m, 4H), 7.45 (d, J=8.2, 2H), 7.12 (d, J=8.2, 2H), 2.50 (d, J=7.8, 2H), 1.66-1.34 (m, 6H), 1.22 (m, 22H), 0.83 (t, J=6.9, 3H); $^{13}$C NMR (126 MHz, DMSO) δ 168.25, 166.50, 138.51, 136.62, 128.69, 128.59, 121.41, 121.35, 34.99, 31.79, 31.41, 29.96, 29.45, 29.30, 29.12, 29.02, 22.54, 15.16, 14.39.

((oct-7-en-1-yloxy)methyl)cyclohexane (11)

General procedure J was used to convert 6.56 mmol of 7-bromo-1-heptene to 5.73 mmol (87%) of the title compound.

1-(7-(cyclohexylmethoxy)heptyl)-4-nitrobenzene (12)

General procedure M was used to convert 5.73 mmol of 11 and 6.30 mmol of 1-bromo-4-nitrobenzene to 3.72 mmol (65%) of the title compound.

4-(7-(cyclohexylmethoxy)heptyl)aniline (13)

General procedure N was used to convert 0.657 mmol of 12 to 0.616 mmol (94%) of the title compound.

1-cyano-N-(4-(7-(cyclohexylmethoxy)heptyl)phenyl)cyclopropanecarboxamide (14)

General procedure E was used to convert 0.616 mmol of 13 and 0.924 mmol of 1-cyanocyclopropanecarboxylic acid to 0.590 mmol (96%) of the title compound.

VPC143105

General procedure H was used to convert 0.590 mmol of 14 to 0.349 mmol (59%) of the title product and submitted for biological evaluation.

((hept-6-en-1-yloxy)methyl)benzene (11a)

General procedure J was used to convert 6.56 mmol of 7-bromo-1-heptene to 5.90 mmol (90%) of the title compound.

1-(7-(benzyloxy)heptyl)-4-nitrobenzene (12a)

General procedure M was used to convert 5.90 mmol of 11a and 6.49 mmol of 1-bromo-4-nitrobenzene to 4.03 mmol (68%) of the title compound.

4-(7-(benzyloxy)heptyl)aniline (13a)

General procedure N was used to convert 1.10 mmol of 12a to 1.05 mmol (95%) of the title compound.

N-(4-(7-(benzyloxy)heptyl)phenyl)-1-cyanocyclopropanecarboxamide (14a)

General procedure E was used to convert 1.05 mmol of 13a and 1.575 mmol of 1-cyanocyclopropanecarboxylic acid to 1.03 mmol (98%) of the title compound.

VPC143078

General procedure H was used to convert 1.03 mmol of 14a to 0.330 mmol (32%) of the title product and submitted for biological evaluation.

((hex-5-en-1-yloxy)methyl)cyclohexane (11b)

General procedure J was used to convert 7.48 mmol of 6-bromo-1-hexene to 5.21 mmol (70%) of the title compound.

1-(6-(cyclohexylmethoxy)hexyl)-4-nitrobenzene (12b)

General procedure M was used to convert 5.21 mmol of 11b and 5.73 mmol of 1-bromo-4-nitrobenzene to 1.35 mmol (26%) of the title compound.

4-(6-(cyclohexylmethoxy)hexyl)aniline (13b)

General procedure N was used to convert 1.35 mmol of 12b to 1.30 mmol (96%) of the title compound.

1-cyano-N-(4-(6-(cyclohexylmethoxy)hexyl)phenyl)cclopropanecarboxamide (14b)

General procedure E was used to convert 1.30 mmol of 13b and 1.95 mmol of 1-cyanocyclopropanecarboxylic acid to 1.29 mmol (99%) of the title compound.
VPC143113
General procedure H was used to convert 1.29 mmol of 14b to 0.581 mmol (45%) of the title product and submitted for biological evaluation.

((oct-7-en-1-yloxy)methyl)cyclohexane (11c)

General procedure J was used to convert 5.98 mmol of 8-bromo-1-octene to 4.56 mmol (77%) of the title compound.

1-(8-(cyclohexylmethoxy)octyl)-4-nitrobenzene (12c)

General procedure M was used to convert 4.56 mmol of 11c and 5.02 mmol of 1-bromo-4-nitrobenzene to 2.19 mmol (48%) of the title compound.

4-(8-(cyclohexylmethoxy)octyl)aniline (13c)

General procedure N was used to convert 2.19 mmol of 12c to 2.05 mmol (94%) of the title compound.

1-cyano-N-(4-(8-(cyclohexylmethoxy)octyl)phenyl)cyclopropanecarboxamide (14c)

General procedure E was used to convert 2.05 mmol of 13c and 3.08 mmol of 1-cyanocyclopropanecarboxylic acid to 2.01 mmol (98%) of the title compound.
VPC143126
General procedure H was used to convert 2.01 mmol of 14c to 0.679 mmol (34%) of the title product and submitted for biological evaluation.

2-((hept-6-en-1-yloxy)methyl)adamantane (11d)

General procedure J was used to convert 3.26 mmol of 7-bromo-1-heptene to 2.77 mmol (85%) of the title compound.

2-(((7-(4-nitrophenyl)heptyl)oxy)methyl)adamantane (12d)

General procedure M was used to convert 2.77 mmol of 11d and 3.05 mmol of 1-bromo-4-nitrobenzene to 1.30 mmol (47%) of the title compound.

4-(7-(adamantan-2-ylmethoxy)heptyl)aniline (13d)

General procedure N was used to convert 1.30 mmol of 12d to 1.30 mmol (100%) of the title compound.

N-(4-(7-(adamantan-2-ylmethoxy)heptyl)phenyl)-1-cyanocyclopropanecarboxamide (14d)

General procedure E was used to convert 1.30 mmol of 13d and 1.95 mmol of 1-cyanocyclopropanecarboxylic acid to 1.25 mmol (96%) of the title compound.
VPC143090
General procedure H was used to convert 1.25 mmol of 14d to 0.891 mmol (71%) of the title product and submitted for biological evaluation.

non-8-en-1-ylbenzene (15)

General procedure L was used to convert 5.98 mmol of 8-bromo-1-octene to 5.08 mmol (85%) of the title compound.

1-nitro-4-(9-phenylnonyl)benzene (16)

General procedure M was used to convert 5.08 mmol of 15 and 5.59 mmol of 1-bromo-4-nitrobenzene to 2.74 mmol (54%) of the title compound.

4-(9-phenylnonyl)aniline (17)

General procedure N was used to convert 2.74 mmol of 16 to 2.56 mmol (93%) of the title compound.

1-cyano-N-(4-(9-phenylnonyl)phenyl)cyclopropanecarboxamide (18)

General procedure E was used to convert 2.56 mmol of 17 and 3.84 mmol of 1-cyanocyclopropanecarboxylic acid to 2.40 mmol (94%) of the title compound.
VPC143129
General procedure H was used to convert 2.40 mmol of 18 to 1.12 mmol (47%) of the title product and submitted for biological evaluation.

oct-7-en-1-ylbenzene (15a)

General procedure L was used to convert 6.52 mmol of 7-bromo-1-heptene to 5.45 mmol (84%) of the title compound.

1-nitro-4-(8-phenyloctyl)benzene (16a)

General procedure M was used to convert 5.31 mmol of 15a and 5.84 mmol of 1-bromo-4-nitrobenzene to 3.42 mmol (71%) of the title compound.

4-(8-phenyloctyl)aniline (17a)

General procedure N was used to convert 3.42 mmol of 16a to 3.15 mmol (92%) of the title compound.

1-cyano-N-(4-(8-phenyloctyl)phenyl)cyclopropanecarboxamide (18a)

General procedure E was used to convert 3.15 mmol of 17a and 4.73 mmol of 1-cyanocyclopropanecarboxylic acid to 3.10 mmol (98%) of the title compound.
VPC143119
General procedure H was used to convert 3.10 mmol of 18a to 1.34 mmol (43%) of the title product and submitted for biological evaluation.

N-(1-cyanocyclopropyl)-4-(7-(cyclohexylmethoxy)heptyl)benzamide (21)

General procedure G was used to convert 1.89 mmols of 20 to an acid chloride. After standard purification techniques, the acyl-chloride was isolated in quantitative yield and immediately. General procedure F was used to couple 1.89 mmols of 1-amino-1-cyclopropanecarbonitrile. After standard purification techniques, 1.34 mmols (71%) of the title product was recovered
VPC14a1051

General procedure H was used to convert 1.34 mmol of 21 to 1.13 mmol (84%) of the title product and submitted for biological evaluation.

((hept-6-en-1-yloxy)methyl)cyclopentane (11e)

General procedure J was used to convert 3.26 mmol of 7-bromo-1-heptene to 2.86 mmol (88%) of the title compound.

4-(7-(cyclopentylmethoxy)heptyl)benzaldehyde (19a)

General procedure M was used to convert 2.86 mmol of 11e and 3.15 mmol of 1-bromo-4-nitrobenzene to 2.29 mmol (80%) of the title compound.

4-(7-(cyclopentylmethoxy)heptyl)benzoic acid (20a)

General procedure I was used to convert 3.15 mmol of 19a to 3.15 mmol (100%) of the title compound.

N-(1-cyanocyclopropyl)-4-(7-(cyclopentylmethoxy)heptyl)benzamide (21a)

General procedure G was used to convert 3.15 mmols of 20a to an acid chloride. After standard purification techniques, the acyl-chloride was isolated in quantitative yield and immediately. General procedure F was used to couple 3.15 mmols of 1-amino-1-cyclopropanecarbonitrile. After standard purification techniques, 2.05 mmols (65%) of the title product was recovered.
VPC143154

General procedure H was used to convert 2.05 mmol of 21a to 1.76 mmol (86%) of the title product and submitted for biological evaluation.

((dec-9-en-1-yloxy)methyl)cyclohexane (22)

General procedure J was used to convert 4.90 mmol of 10-bromo-1-decene to 3.62 mmol (74%) of the title compound.

10-(cyclohexylmethoxy)decan-1-ol (23)

General procedure O was used to convert 3.62 mmol of 22 to 2.72 mmol (75%) of the title compound. $^1$H NMR (300 MHz, CDCl$_3$) δ 4.33 (d, J=2.8 Hz, 1H), 3.53 (t, J=6.6 Hz, 2H), 3.30 (t, J=6.7 Hz, 2H), 3.12 (d, J=6.6 Hz, 2H), 2.18 (s, 1H), 1.52 (m, 16H), 1.20 (m, 8H), 0.83 (m, 2H). $^{13}$C NMR (75 MHz, CDCl$_3$) δ 76.90, 71.61, 71.18, 70.76, 69.57, 68.06, 64.21, 62.23, 60.28, 41.95, 38.33, 37.33, 34.66, 34.09, 33.53, 32.99, 32.48, 31.76, 30.35, 29.85, 27.76, 26.92, 26.74, 26.46, 26.15, 25.44, 22.98, 22.33, 20.75, 19.35, 14.26, 13.79.

(((10-azidodecyl)oxy)methyl)cyclohexane (24)

General procedure P was used to convert 2.72 mmol of 23 to 2.07 mmol (76%) of the title compound. $^1$H NMR (300 MHz, CDCl$_3$) δ 3.31 (t, J=6.6 Hz, 2H), 3.13 (d, J=6.5 Hz, 2H), 1.66 (m, 17H), 1.21 (m, 12H). $^{13}$C NMR (75 MHz, CDCl$_3$) δ 71.25, 69.78, 62.33, 58.18, 51.61, 38.26, 37.25, 33.85, 30.95, 30.82, 30.36, 29.93, 29.85, 29.63, 29.33, 29.03, 27.41, 26.89, 26.56, 26.37, 26.10, 25.86, 25.29, 23.33, 21.01, 14.34.

1-cyano-N-(10-(cyclohexylmethoxy)decyl)cyclopropanecarboxamide (26)

General procedure Q was used to convert 2.72 mmol of 24 to 0.626 mmol (23%) of the title compound. $^1$H NMR (300 MHz, CDCl$_3$) δ 6.61 (s, 1H) 3.33 (t, J=6.6 Hz, 2H), 3.23 (dd, J=13.4, 6.8 Hz, 2H), 3.14 (d, J=6.6 Hz, 2H), 1.54 (m, 17H), 1.19 (m, 11H). 0.83 (m, 4H). $^{13}$C NMR (75 MHz, CDCl$_3$) δ 165.21, 120.49, 71.28, 50.94, 40.85, 38.23, 32.44, 30.91, 30.37, 29.93, 29.63, 29.41, 27.17, 26.98, 26.88, 26.36, 26.10, 25.67, 23.87, 17.63, 13.64.
VPC143144

General procedure H was used to convert 0.626 mmol of 26 to 0.134 mmol (21%) of the title product and submitted for biological evaluation.

((dec-9-en-1-yloxy)methyl)cyclopentane (22a)

General procedure J was used to convert 4.90 mmol of 10-bromo-1-decene to 3.54 mmol (72%) of the title compound. $^1$H NMR (300 MHz, CDCl3) δ 5.78 (ddt, J=6.7, 10.2, 16.9, 1H), 4.92 (m, 2H), 3.37 (m, 4H), 2.52 (dq, J=7.2, 14.2, 1H), 2.02 (m, 3H), 1.85 (m, 2H), 1.70 (m, 2H), 1.53 (m, 3H), 1.30 (d, J=14.9, 8H). $^{13}$C NMR (75 MHz, CDCl$_3$) δ 139.12, 114.27, 71.24, 35.42, 34.00, 29.93, 29.65, 29.28, 29.11, 26.36, 25.30, 18.78.

10-(cyclopentylmethoxy)decan-1-ol (23a)

General procedure O was used to convert 3.54 mmol of 22a to 2.59 mmol (73%) of the title compound. $^1$H NMR (500 MHz, CDCl$_3$) δ 3.58 (t, J=6.7, 2H), 3.36 (m, 4H), 2.52 (dq, J=7.4, 14.8, 1H), 2.02 (m, 3H), 1.83 (m, 2H), 1.65 (m, 3H), 1.49 (m, 6H), 1.23 (dd, J=6.5, 13.9, 8H). $^{13}$C NMR (126 MHz, CDCl$_3$) δ 75.15, 70.77, 70.09, 59.99, 38.16, 36.81, 35.05, 31.83, 29.27, 28.05, 26.86, 25.22, 22.07, 20.62, 18.38, 13.94.

(((10-azidodecyl)oxy)methyl)cyclopentane (24a)

General procedure P was used to convert 2.59 mmol of 23a to 1.87 mmol (72%) of the title compound. $^1$H NMR (300 MHz, CDCl$_3$) δ 3.35 (t, J=7.0, 4H), 3.20 (t, J=6.9, 2H), 2.52 (s, 1H), 1.99 (s, 3H), 1.84 (d, J=6.0, 3H), 1.69 (d, J=9.8, 3H), 1.52 (s, 5H), 1.25 (s, 8H). $^{13}$C NMR (75 MHz, CDCl$_3$) δ 77.82, 71.24, 51.60, 35.39, 30.92, 29.90, 29.63, 29.33, 29.03, 27.41, 26.89, 26.33, 25.33, 23.31, 18.80.

1-cyano-N-(10-(cyclopentylmethoxy)decyl)cyclopropanecarboxamide (26a)

General procedure Q was used to convert 1.87 mmol of 24a to 0.511 mmol (27%) of the title compound. $^1$H NMR (300 MHz, CDCl$_3$) δ 6.63 (s, 1H), 3.36 (t, J=6.8 Hz, 4H), 3.24 (tt, J=18.4, 9.2 Hz, 2H), 2.51 (dq, J=14.4, 7.2 Hz, 1H), 2.01 (m, 2H), 1.84 (m, 2H), 1.58 (m, 14H), 1.25 (s, 8H). $^{13}$C NMR (75 MHz, CDCl$_3$) δ 165.24, 120.52, 75.74, 71.29, 53.77, 40.86, 35.37, 29.90, 29.62, 29.40, 26.98, 26.32, 25.38, 19.28, 18.82, 17.64, 13.66.

VPC14a1058

General procedure H was used to convert 0.511 mmol of 26a to 0.237 mmol (46%) of the title product and submitted for biological evaluation.

1-cyano-N-tetradecylcyclopropanecarboxamide (27)

General procedure E was used; white solid isolated, 304 mg (0.99 mmol, 99%): $R_f$=0.45 (20% EtOAc in hexanes); $^1$H NMR (300 MHz, CDCl3) δ 6.41 (s, 1H), 3.46-3.15 (m, 2H), 1.66 (dd, J=4.4, 8.1, 2H), 1.58-1.39 (m, 4H), 1.26 (m, 22H), 0.86 (t, J=6.7, 3H); $^{13}$C NMR (75 MHz, CDCl3) δ 165.22, 120.54, 40.89, 32.14, 29.87, 29.79, 29.71, 29.58, 29.45, 27.01, 22.91, 17.65, 14.34, 13.67.

VPC143057

General procedure H was used; white solid isolated, 150 mg (0.42 mmol, 42%): $^1$H NMR (300 MHz, DMSO) δ 8.96 (s, 4H), 7.82 (s, 1H), 3.02 (s, 2H), 1.28 (m, 22H), 0.83 (s, 3H); $^{13}$C NMR (75 MHz, DMSO) δ 168.55, 167.92, 31.98, 29.74, 29.56, 29.48, 29.40, 29.09, 27.04, 22.78, 14.86, 14.64.

1-cyano-N-hexadecylcyclopropanecarboxamide (27a)

General procedure E was used; white solid isolated, 319 mg (0.99 mmol, 99%): $R_f$=0.47 (20% EtOAc in hexanes); $^1$H NMR (500 MHz, CDCl3) δ 6.37 (s, 1H), 3.28 (dd, J=6.6, 13.7, 2H), 1.73-1.60 (m, 2H), 1.53 (d, J=7.3, 2H), 1.47 (dd, J=4.3, 8.1, 1H), 1.27 (m, 24H), 0.87 (t, J=6.9, 3H); $^{13}$C NMR (126 MHz, CDCl3) δ 164.99, 120.33, 40.68, 31.91, 29.67, 29.56, 29.48, 29.38, 29.22, 26.78, 22.68, 17.43, 14.12.

VPC143046

General procedure H was used; white solid isolated, 174 mg (0.45 mmol, 45%): $^1$H NMR (300 MHz, DMSO) δ 8.96 (s, 4H), 7.82 (s, 1H), 3.02 (s, 2H), 1.28 (m, 24H), 0.83 (s, 3H); $^{13}$C NMR (126 MHz, DMSO) δ 168.25, 166.50, 138.51, 136.62, 128.69, 128.59, 121.41, 121.35, 34.99, 31.79, 31.41, 29.96, 29.45, 29.30, 29.12, 29.02, 22.54, 15.16, 14.39.

1-cyano-N-octadecylcyclopronanecarboxamide (27b)

General procedure E was used; white solid isolated (0.99 mmol, 99%): $R_f$=0.47 (20% EtOAc in hexanes).

VPC14a1002

General procedure H was used; white solid isolated (0.05 mmol, 5%).

(S)-tert-butyl 2-cyanopyrrolidine-1-carboxylate (28)

To a flame dried flask was added 2 grams (9.3 mmols) of N-Boc proline followed by 93 mL of dichloromethane and 4.24 grams (41.85 mmols) of triethylamine. The reaction mixture was then cooled to −25° C. and 2.5 grams (18.6 mmols) of iso-butylchloroformate was added dropwise. After stirring for 45 minutes at this low temperature, 0.83 grams (49 mmol) of ammonia was added to the reaction mixture as a 7N solution in methanol. The flask was allowed to warm to ambient temperature and stir for an additional 16 hours. After this time, the reaction mixture was evaporated to dryness and reconstituted in 200 mL of EtOAc. The organic layer was washed four 15 mL portions of 1N HCl, dried with MgSO$_4$ and evaporated to dryness. The crude material was then immediately dehydrated to the nitrile according to general procedure E using 1.9 grams (18.88 mmols) of triethylamine and 2.34 grams (11.16 mmols) of trifluoroacetic anhydride in 93 mL of THF. After standard work-up and purification techniques (column chromatography, 25% EtOAc in hexanes), 0.91 grams (4.65 mmols, 50%) of the title product was recovered as a yellow oil. $^1$H NMR (300 MHz, CDCl$_3$) δ 4.53 (d, J=5.5 Hz, 0.5H), 4.48-4.38 (m, 0.5H), 3.57-3.41 (m, 1H), 3.41-3.22 (m, 1H), 2.31-1.92 (m, 4H), 1.47 (d, J=9.4 Hz, 9H). $^{13}$C NMR (75 MHz, CDCl$_3$) δ 153.25, 119.38, 81.64, 47.39, 45.93, 31.86, 31.01, 28.52, 24.88, 24.04.

(S)-1-(4-dodecylbenzoyl)pyrrolidine-2-carbonitrile (29)

General procedure D was used to deprotect 0.4 grams (2.05 mmols) of 28 using 21 mL of dichloromethane and trifluoroacetic acid. After standard work-up procedures, the TFA salt of 28 was coupled to 0.6 grams (2.05 mmols) of 4-dodecylbenzoic acid using 1.1 grams (2.05 mmols) of PyBOP and 1.1 grams (8.2 mmols) of N,N-diisopropylethylamine in 21 mL of dichloromethane according general procedure E and heating to 50° C. After previously described work-up and purification procedures (column chromatography, 25% EtOAc in hexanes), 0.17 grams (0.45 mmols, 22%) of the title product was recovered as an off-white solid. $^1$H NMR (500 MHz, CDCl$_3$) δ 7.50 (d, J=8.0 Hz, 2H), 7.22 (d, J=7.6 Hz, 2H), 4.96-4.84 (m, 1H), 3.73-3.63 (m, 1H), 5.62-3.52 (m, 1H), 2.68-2.58 (m, 2H), 2.39-2.26 (m, 1H), 2.24-2.10 (m, 1H), 2.06-1.96 (m, 1H), 1.67-1.55 (m, 1H), 1.39-1.18 (m, 18H), 0.87 (t, J=6.9 Hz, 3H). $^{13}$C NMR (126 MHz, CDCl$_3$) δ 170.18, 146.28, 128.40, 127.61, 127.17, 118.73, 49.51, 46.87, 35.84, 31.91, 31.20, 30.30, 29.65, 29.56, 29.46, 29.34, 29.23, 25.58, 22.68, 14.12.

VPC96091

General procedure H was used to convert 0.21 grams (0.56 mmols) of 29 to the title product using 112 μL of 0.5M sodium methoxide in methanol (0.003 grams, 0.056 mmols), 6 mL of anhydrous methanol and 0.033 grams (0.62 mmols) of ammonium chloride. After previously described recrystallization procedures 0.084 grams (0.2 mmols, 36%) of VPC96091 was recovered as a powdery white solid and submitted for biological evaluation. $^1$H NMR (500 MHz, CD$_3$OD) δ 7.63 (d, J=8.0 Hz, 2H), 7.30 (d, J=8.0 Hz, 2H), 4.73 (t, J=7.5 Hz, 1H), 3.87 (dd, J=15.4, 9.0 Hz, 1H), 3.73-3.60 (m, 1H), 2.67 (t, J=7.6 Hz, 2H), 2.54 (dd, J=13.3, 6.6 Hz, 1H), 2.12-1.93 (m, 2H), 1.71-1.56 (m, 1H), 1.34-1.28 (m, 18H), 0.90 (t, J=6.9 Hz, 3H). $^{13}$C NMR (126 MHz, CD$_3$OD) δ 171.79, 146.52, 131.91, 128.06, 127.63, 58.94, 50.59, 35.36, 31.66, 31.14, 31.03, 29.33, 29.28, 29.15, 29.06, 28.88, 25.27, 22.32, 13.03.

(S)-1-(4-undecylbenzoyl)pyrrolidine-2-carbonitrile (29a)

General procedure D was used to deprotect 0.447 grams (2.3 mmols) of 28. After standard work-up procedures, general procedure E was used to couple 2.3 mmols of the TFA salt of 28 to 0.635 grams (2.3 mmols) of 4-undecylbenzoic acid at 50° C. After work-up, 0.334 grams (0.94 mmols, 41%) of the title product was isolated as a yellow solid by flash chromatography (25% EtOAc in hexanes). $^1$H NMR (300 MHz, CDCl$_3$) δ 7.24 (dd, J=12.2, 4.4 Hz, 2H), 7.04 (t, J=7.7 Hz, 2H), 4.97 (s, 1H), 3.88 (s, 1H), 3.31 (dt, J=18.1, 9.0 Hz, 1H), 2.77-2.64 (m, 1H), 2.63-2.54 (m, 1H), 2.24-2.12 (m, 1H), 1.60 (dt, J=15.1, 7.3 Hz, 4H), 1.29 (d, J=10.9 Hz, 14H), 0.88 (t, J=6.7 Hz, 3H). $^{13}$C NMR (126 MHz, CDCl$_3$) δ 169.97, 146.29, 128.42, 128.18, 127.63, 127.17, 118.73, 49.51, 46.85, 46.20, 35.84, 31.91, 31.20, 30.27, 29.64, 29.61, 29.56, 29.46, 29.33, 29.23, 25.57, 22.68, 14.12.

VPC96077

General procedure H was used to convert 0.148 grams (0.42 mmols) of 29a to the title product. After standard recrystallization techniques, 0.068 grams (0.16 mmols, 38%) of the amidine was recovered as a powdery white solid.

(S)-1-(4-octylbenzoyl)pyrrolidine-2-carbonitrile (29b)

General procedure D was used to deprotect 0.4 grams (2.05 mmols) of 28 in 21 mL of dichloromethane and trifluoroacetic acid. After work-up, the TFA salt of 28 was then coupled to 0.6 grams (2.05 mmols) of 4-octylbenzoic acid with 1.1 grams (2.05 mmols) of PyBOP and 1.1 grams (8.2 mmols) of N,N-diisopropylethylamine in 21 mL of dichloromethane according to general procedure E and heating at 50° C. After previously described work-up and purification procedures (column chromatography, 25% EtOAc in hexanes) 0.256 grams (0.82 mmols, 40%) of the title product was recovered.

VPC95127

General procedure H was used to convert 0.1 grams (0.32 mmols) of (S)-1-(4-octylbenzoyl)pyrrolidine-2-carbonitrile to the title product using 0.032 mmols of sodium methoxide as a 0.5 M solution in methanol and 0.019 grams (0.352 mmols) of ammonium chloride. After standard work-up procedures, 0.039 grams (0.107 mmols, 33%) of the title product was recovered as an off white solid. $^1$H NMR (500 MHz, CD$_3$OD) δ 7.62 (d, J=5.6 Hz, 2H), 7.31 (d, J=7.8 Hz, 2H), 4.71 (dd, J=6.9, 4.4 Hz, 2H), 3.85 (s, 1H), 3.68 (s, 1H), 2.67 (t, J=7.8 Hz, 2H), 2.54 (d, J=9.1 Hz, 1H), 2.03 (d, J=24.3 Hz, 2H), 1.62 (d, J=13.3 Hz, 1H), 1.30 (m, 10H), 0.89 (t, J=6.7 Hz, 3H).

4-(octyloxy)benzaldehyde (30)

4-hydroxybenzaldehyde (8.2 mmols), 1-bromooctane (12.3 mmols) and cesium carbonate (16.4 mmols) were dissolved in DMF (13.7 mmols). The mixture was then heated to 80° C. and stirred for 3 hours. After this time, the reaction mixture was filtered through a fine fritted funnel; the eluent was collected and diluted with 200 mLs of EtOAc. The organic layer was extracted with seven 10 mL portions of H$_2$O and two 15 mL portions of brine. The organic layer was dried with MgSO$_4$ and evaporated to dryness. After purification by flash chromatography 7.8 mmols of the title product was recovered. $^1$H NMR (500 MHz, CDCl$_3$) δ 9.86 (d, J=2.9, 1H), 7.94-7.74 (m, 2H), 7.05-6.92 (m, 2H), 4.02 (td, J=3.1, 6.5, 2H), 1.88-1.73 (m, 2H), 1.44 (dd, J=6.8, 14.2, 2H), 1.39-1.21 (m, 8H), 0.99-0.81 (m, 3H). $^{13}$C NMR (126 MHz, CDCl$_3$) δ 190.76, 164.24, 131.95, 129.70, 114.71, 68.40, 31.77, 29.28, 29.03, 25.95, 22.63, 14.08.

4-(octyloxy)benzoic acid (31)

General procedure I was used to convert 7.8 mmols of 30 to the title product. After standard purification techniques, 7.8 mmols of the acid were recovered. $^1$H NMR (500 MHz, CDCl$_3$) δ 8.06 (d, J=8.8, 2H), 6.93 (dd, J=2.2, 9.3, 2H), 4.02 (t, J=6.6, 2H), 1.86-1.75 (m, 2H), 1.51-1.42 (m, 2H), 1.33 (ddd, J=7.5, 13.7, 18.7, 8H), 0.89 (t, J=6.9, 3H). $^{13}$C NMR (126 MHz, CDCl$_3$) δ 171.96, 163.68, 132.32, 121.33, 114.17, 68.28, 31.78, 29.31, 29.07, 25.97, 22.64, 14.08.

(S)—N-(1-cyanoethyl)-4-(octyloxy)benzamide (32)

General procedure D and E were used to deprotect 1.17 mmols of (S)-tert-butyl 1-cyanoethylcarbamate and couple the resulting amine to 1.17 mmols of 31. After standard purification techniques 0.35 mmols of the title product were recovered. $^1$H NMR (500 MHz, CDCl$_3$) δ 7.74 (d, J=8.9, 2H), 6.90 (d, J=8.8, 2H), 6.67 (s, 1H), 5.30-5.05 (m, 1H), 3.98 (t, J=6.6, 2H), 1.85-1.74 (m, 2H), 1.64 (d, J=7.2, 3H), 1.45 (s, 3H), 1.30 (d, J=19.1, 7H), 0.88 (t, J=6.9, 3H). $^{13}$C NMR (126 MHz, CDCl$_3$) δ 166.26, 162.49, 129.11, 124.52, 119.58, 114.40, 68.26, 36.25, 31.77, 29.30, 29.19, 29.07, 25.95, 22.63, 19.53, 14.08.

VPC95229

General procedure H was used to convert 0.35 mmols of 32 to the title product. After standard purification techniques, 1 mg of the title product was recovered and submitted for biological evaluation. $t_R$=7.9 min.; m/z=320.37.

3-(benzyloxy)benzaldehyde (33)

General procedure K was used to convert 3-hydroxybenzaldehyde (8.2 mmols) and benzyl bromide (12.3 mmols) to 1 (8.2 mmols, quant.) $^1$H NMR (500 MHz, CDCl$_3$) δ 9.98 (s, 1H), 7.51-7.44 (m, 4H), 7.44-7.39 (m, 1H), 7.38-7.33 (m, 1H), 7.26 (ddd, J=1.8, 3.5, 4.2, 1H), 5.13 (s, 2H). $^{13}$C NMR (126 MHz, CDCl$_3$) δ 192.08, 159.29, 137.81, 136.29, 130.13, 128.68, 128.22, 127.56, 123.70, 122.20, 113.22, 77.31, 77.06, 76.80, 70.20.

(3-(benzyloxy)phenyl)methanol (34)

The intermediate 33 (8.2 mmols) and calcium chloride (16.4 mmols) were dissolved in 55 mL of anhydrous ethanol and 27 mLs of THF. The solution was next cooled to 0° C. and sodium borohydride (16.4 mmols) was added slowly over several minutes to the reaction vessel. Upon warming to ambient temperature, the mixture was allowed to stir for an additional 15 hours. After this time, the flask was again cooled to 0° C. and the excess sodium borohydride was quenched with the addition of 5 mLs of 1N HCl. The aqueous layer was extracted with four 20 mL portions of EtOAc; the organic layers were then combined, washed with 10 mLs of brine and dried with MgSO$_4$. After evaporation, the crude organic material was purified by flash chromatography and 6.7 mmols of the title product was recovered. $^1$H NMR (300 MHz, CDCl$_3$) δ 7.49-7.24 (m, 5H), 7.06-6.88 (m, 2H), 5.08 (s, 2H), 4.66 (s, 2H), 1.78 (s, 1H). $^{13}$C NMR (75 MHz, CDCl$_3$) δ 129.88, 128.83, 128.21, 127.72, 119.60, 114.35, 113.45, 70.17, 65.46.

4-(3-(benzyloxy)benzyloxy)benzaldehyde (35)

To a stirring solution of triphenylphosphine (1.1 mmols) in THF (2 mLs) was added 34 (1.1 mmols). The solution was immediately cooled to 0° C. and diisopropyl azodicarboxylate (1.1 mmols) was added dropwise and the mixture was stirred at this low temperature for 15 minutes. After this time, 4-hydroxybenzaldehyde (1 mmol) was added to the reaction vessel, still stirring at 0° C. The mixture was warmed slowly to ambient temperature and stirred for 15 hours. At this time, the THF was evaporated, reconstituted in Et$_2$O and filtered through a small portion of silica gel. The eluent was collected and evaporated to dryness. The title product (0.45 mmols) was recovered after flash chromatography. ¹H NMR (300 MHz, CDCl₃) δ 9.89 (s, 1H), 7.91-7.77 (m, 2H), 7.50-7.30 (m, 6H), 7.03 (ddd, J=5.1, 11.5, 24.0, 5H), 5.13 (s, 2H), 5.08 (s, 2H). ¹³C NMR (75 MHz, CDCl₃) δ 191.04, 163.88, 159.36, 137.82, 136.98, 132.24, 130.09, 128.86, 128.29, 127.74, 120.05, 115.39, 114.79, 114.14, 77.70, 77.27, 76.85, 70.25.

4-(3-(benzyloxy)benzyloxy)benzoic acid (36)

General procedure I was used to oxidize 0.45 mmols of 35 to the corresponding carboxylic acid. The title product was recovered in quantitative yield; no further purification was carried out other than that outlined in the general procedure. The recovered product was extremely insoluble in deuterated NMR solvents and no spectra could be recovered. The acid was therefore carried on to amide coupling.

(S)-4-(3-(benzyloxy)benzyloxy)-N-(1-cyanoethyl) benzamide (37)

General procedures D and E were used to deprotect 0.45 mmols of (S)-tert-butyl 1-cyanoethylcarbamate and couple to 0.45 mmols of the acid 36. After purification by flash chromatography, 0.23 mmols of the title product was recovered. ¹H NMR (500 MHz, CDCl₃) δ 7.78-7.72 (m, 2H), 7.47-7.42 (m, 2H), 7.41-7.37 (m, 2H), 7.36-7.29 (m, 2H), 7.06 (s, 1H), 7.02 (s, 1H), 7.01-6.98 (m, 2H), 6.95 (dd, J=2.5, 8.2, 1H), 6.46 (s, 1H), 5.15 (dd, J=7.6, 14.9, 1H), 5.09 (s, 2H), 5.07 (s, 2H), 1.65 (d, J=7.2, 3H). ¹³C NMR (75 MHz, CDCl₃) δ 191.04, 163.88, 159.36, 137.82, 136.98, 132.24, 130.09, 128.86, 128.29, 127.74, 120.05, 115.39, 114.79, 114.14, 70.25.
VPC95219

General procedure H was used (with ammonium bromide in place of ammonium chloride) to convert 0.22 mmols of 37 to the corresponding amidine. Purification procedure B was used to purify the title product, which was carried on for biological evaluation. $t_R$=9.5 min.; m/z=404.15.

4-(7-(cyclohexylmethoxy)heptyl)benzaldehyde (38)

General procedure M was used to convert 2.45 mmol of 11 and 2.70 mmol of 1-bromo-4-nitrobenzene to 1.89 mmol (77%) of the title compound.

4-(7-(cyclohexylmethoxy)heptyl)benzoic acid (39)

General procedure I was used to convert 1.89 mmol of 38 to 1.89 mmol (100%) of the title compound.

(S)-1-(4-(7-(cyclohexylmethoxy)heptyl)benzoyl) pyrrolidine-2-carbonitrile (40)

General procedure G was used to convert 2.77 mmols of 39 to an acid chloride. After standard purification techniques, the acyl-chloride was isolated in quantitative yield and immediately to coupled 2.77 mmols of the TFA salt of (S)-pyrrolidine-2-carbonitrile according to general procedure F. After standard purification techniques, 1.23 mmols (44%) of the title product was recovered.
VPC143237

General procedure H was used to convert 1.23 mmol of 21 to 0.780 mmol (84%) of the title product. The amidine HCl sat is a clear gel that was isolated via flash chromatography with 15% MeOH/CHCl₃. The fractions were concentrated and the oil was filtered through a fine frit with chloroform to remove traces of silica gel. The clear and colorless oil was then mixed with 2N HCl in Et₂O and concentrated to the pure amidine HCl salt and submitted for biological evaluation.

(R)-tert-butyl 2-cyanopyrrolidine-1-carboxylate (41)

To a solution of 2 grams (9.3 mmols) of N-Boc-D-Proline in 19 mL of dichloromethane was added 4.2 grams (42 mmols) of triethylamine. The reaction mixture was cooled to −25° C. and 2.5 grams (18.6 mmols) of iso-butylchloroformate was added dropwise. After stirring at this low temperature for 45 minutes, 0.83 grams (49 mmols) of ammonia was added to the mixture as a 7M solution in methanol. The reaction vessel was warmed slowly to ambient temperature and the solution was stirred for an additional 16 hours. After this time, the reaction mixture was evaporated to dryness and reconstituted in 200 mL of EtOAc. The organic layer was washed with four 15 mL portions of 1N HCl, dried with MgSO₄ and evaporated to dryness. The crude material was immediately subjected to general procedure E using 2 grams (18.9 mmols) of triethylamine and 2.3 grams (11.16 mmols) of trifluoroacetic anhydride in 93 mL of THF. After previously described purification procedures (column chromatography, 25% EtOAc in hexanes), 0.8 grams (4.1 mmols, 44%) of the title product was recovered. ¹H and ¹³C NMR data were identical to that reported for 28.

(R)-1-(4-dodecylbenzoyl)pyrrolidine-2-carbonitrile (42)

General procedure D was used to deprotect 1.4 mmols of 41 using 14 mL of dichloromethane and trifluoroacetic acid. After previously described recrystallization techniques, the TFA salt of 41 was coupled to 0.4 grams (1.4 mmols) of 4-dodecylbenzoic acid using 0.73 grams (1.4 mmols) of PyBOP and 0.72 grams (5.6 mmols) of N,N-diisopropylethylamine in 14 mL of dichloromethane according to general procedure E. Using previously described work-up and purification techniques (column chromatography, 25% EtOAc in hexanes), yielded 0.2 grams (0.55 mmols, 39%) of the title product as an off-white solid. ¹H and ¹³C NMR data were identical to that of 29.
VPC96115

General procedure H was used to convert 0.27 grams (0.73 mmols) of 42 to the title product using 146 µL of 0.5M sodium methoxide in methanol (0.004 grams, 0.073 mmols), 7.3 mL of anhydrous methanol and 0.043 grams (0.8 mmols) of ammonium chloride. After previously described recrystallization procedures, 0.08 grams (0.19 mmols, 26%) of VPC96115 was recovered as a powdery white solid and submitted for biological evaluation. ¹H and ¹³C NMR data were identical to that of VPC96091.
VPC96143

To a solution of 0.293 grams (0.83 mmols) of 29a in anhydrous ethanol was added 0.132 grams (1.9 mmols) of hydroxylamine hydrochloride and 0.202 grams (2 mmols) of triethylamine. The mixture was heated to reflux for 2 hours at which time it was cooled to ambient temperature. The mixture was evaporated to dryness and taken up in 150 mL of chloroform. The organic layer was washed with three 5 mL portions of deionized water, one 5 mL portion of brine and dried of anhydrous MgSO₄. After purification by column chromatography (5% MeOH in CHCl₃), 0.83 mmols of the title product were recovered as an off-white gelatinous solid. ¹H NMR (500 MHz, CDCl₃) δ 7.43 (d, J=7.9 Hz, 2H), 7.19 (d, J=7.8 Hz, 2H), 5.45 (s, 1H), 5.07-4.98 (m, 1H), 3.55

(t, J=5.5 Hz, 1H), 3.47 (s, 1H), 2.60 (t, J=7.6 Hz, 2H), 2.37 (d, J=5.7 Hz, 1H), 2.02 (dd, J=19.5, 10.0 Hz, 2H), 1.79 (dd, J=11.3, 5.9 Hz, 1H), 1.67-1.50 (m, 2H), 1.26 (m, 16H), 0.86 (t, J=6.9 Hz, 3H). $^{13}$C NMR (126 MHz, CDCl$_3$) ? 172.00, 154.17, 145.53, 133.46, 128.27, 127.32, 59.48, 56.67, 50.34, 35.81, 31.89, 31.23, 29.56, 29.47, 29.24, 26.69, 25.31, 22.67, 14.12.

The assays below are standard literature reported assays known in the art for confirming and quantifying the activity of the disclosed compounds.

Single Point Sphingosine Kinase Assay

Sphingosine kinase activity was assessed as described previously (Kharel, Y., Lee, S., Snyder, A. H., Sheasley-O'Neill, S. L., Morris, M. A., Setiady, Y., Zhu, R, Zigler, M. A., Burcin, T. L., Ley, K., Tung, K. S. K., Engelhard, V. H., Macdonald, T. L. and Lynch, K. R. Sphingosine kinase 2 is required for modulation of lymphocyte traffic by FTY720. *J Biological Chemistry* 280: 36865-36872 (2005)). High levels of human sphingosine kinase type 1 (mSK1) and mouse sphingosine kinase type 2 (mSK2) were expressed in Sf9 insect cells by infection with cognate baculoviruses. Crude homogenates were incubated with γ-[$^{32}$P]ATP and 10 micromolar D-erythro-sphingosine in the presence of 100 micromolar concentrations of test compounds for 20 minutes at 37 C. The product, radiolabeled S1P, was isolated by extraction into organic solvents after acidification and displaced by thin layer chromatography. The radiolabeled S1P was scraped using the autoradiogram as a template and the amount of material determine by liquid scintillation counting. The results are illustrated in Table 1.

Determination of Ki Values.

Crude homogenates of Sf9 cells containing high levels of recombinant mouse SphK2 or human SphK1 were incubated with γ-[$^{32}$P]ATP and various concentrations (0 to 500 micromolar) of D-erythro-sphingosine for 20 minutes hour at 37 C in the presence of fixed concentration of test compound. The product, radiolabeled S1P, was isolated by extraction into organic solvents followed by thin layer chromatography, recovered and radioactivity measured by liquid scintillation counting. The Ki values so determined are given in Table 1 (above).

Exemplification of Pro-Drug Activity

Mice were dosed with 20 mpk of amidoxime, VPC96143, both IP and orally. S1P in plasma and organs was measured at times ASAP, 2 hrs and 24 hrs. The compound amidine, VPC96077, was also measured in plasma and organs at times ASAP, 2 hrs and 24 hrs.

Mice Numbering

51: dosed with 20 mpk amidoxime VPC96143 administered IP. Plasma extracted ASAP and 2 hrs. Organs harvested at 2 hrs.
52: dosed with 20 mpk amidoxime VPC96143 administered IP. Plasma extracted ASAP and 24 hrs. Organs harvested at 2 hrs.
53: dosed with 20 mpk amidoxime VPC96143 administered orally. Plasma extracted ASAP and 2 hrs. Organs harvested at 2 hrs.

The results are illustrated in FIGS. 7A-7D.

Figure 8A:
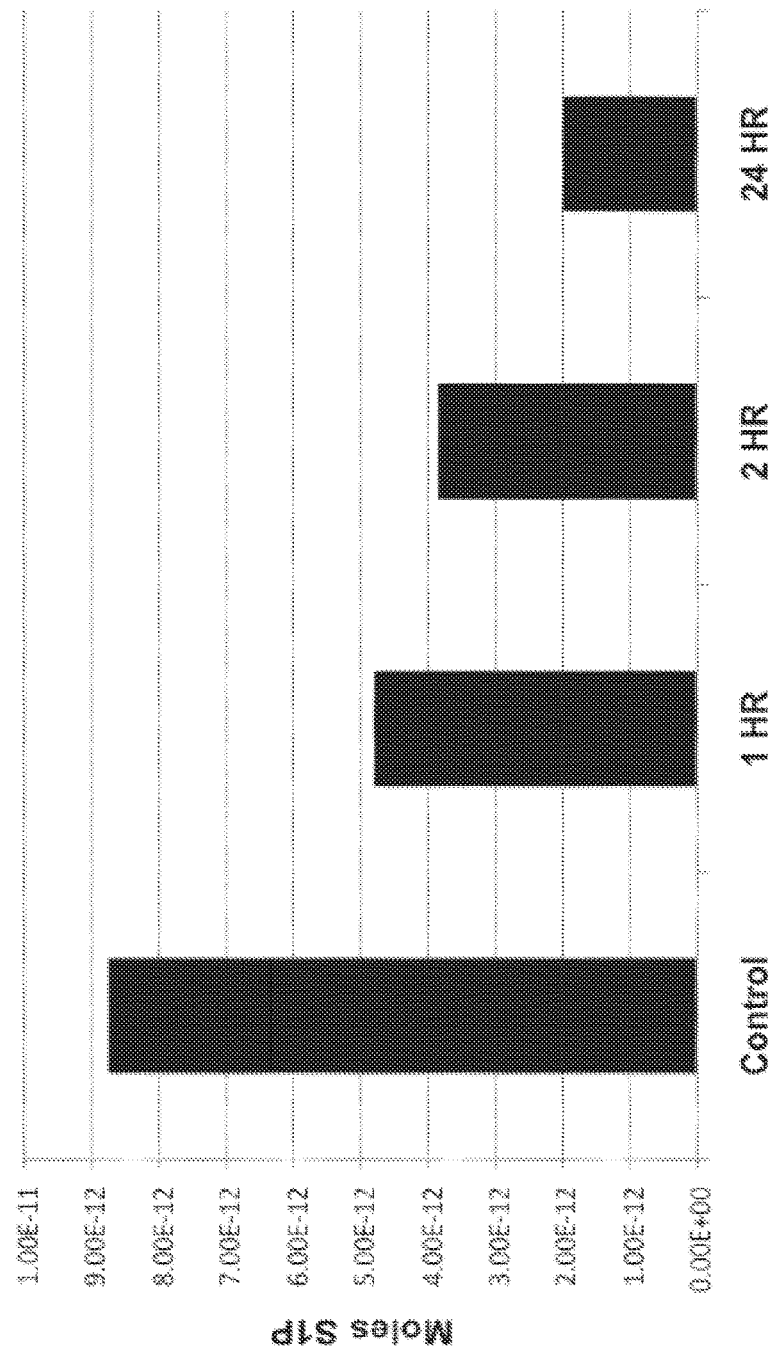
Figure 8B:
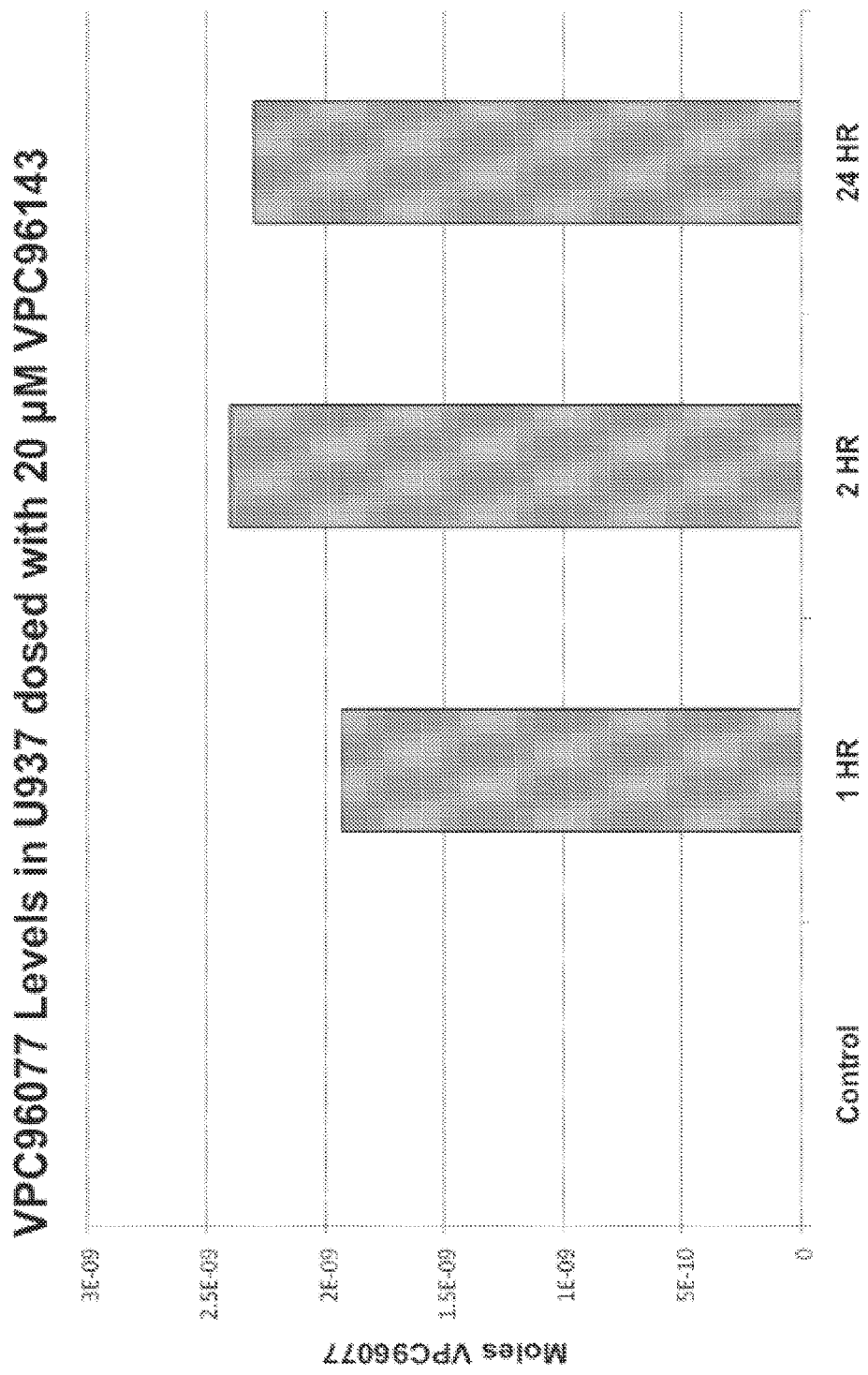

U937 cells (5 million) were treated with 20 μM of amidoxime, VPC96143. The accumulation of S1P was measured at 1 hr, 4 hr and 24 hrs. The levels of amidine, VPC96077 were also measured at 1 hr, 4 hrs and 24 hrs. The results are illustrated in FIGS. 8A-8B.

Figure 9B:
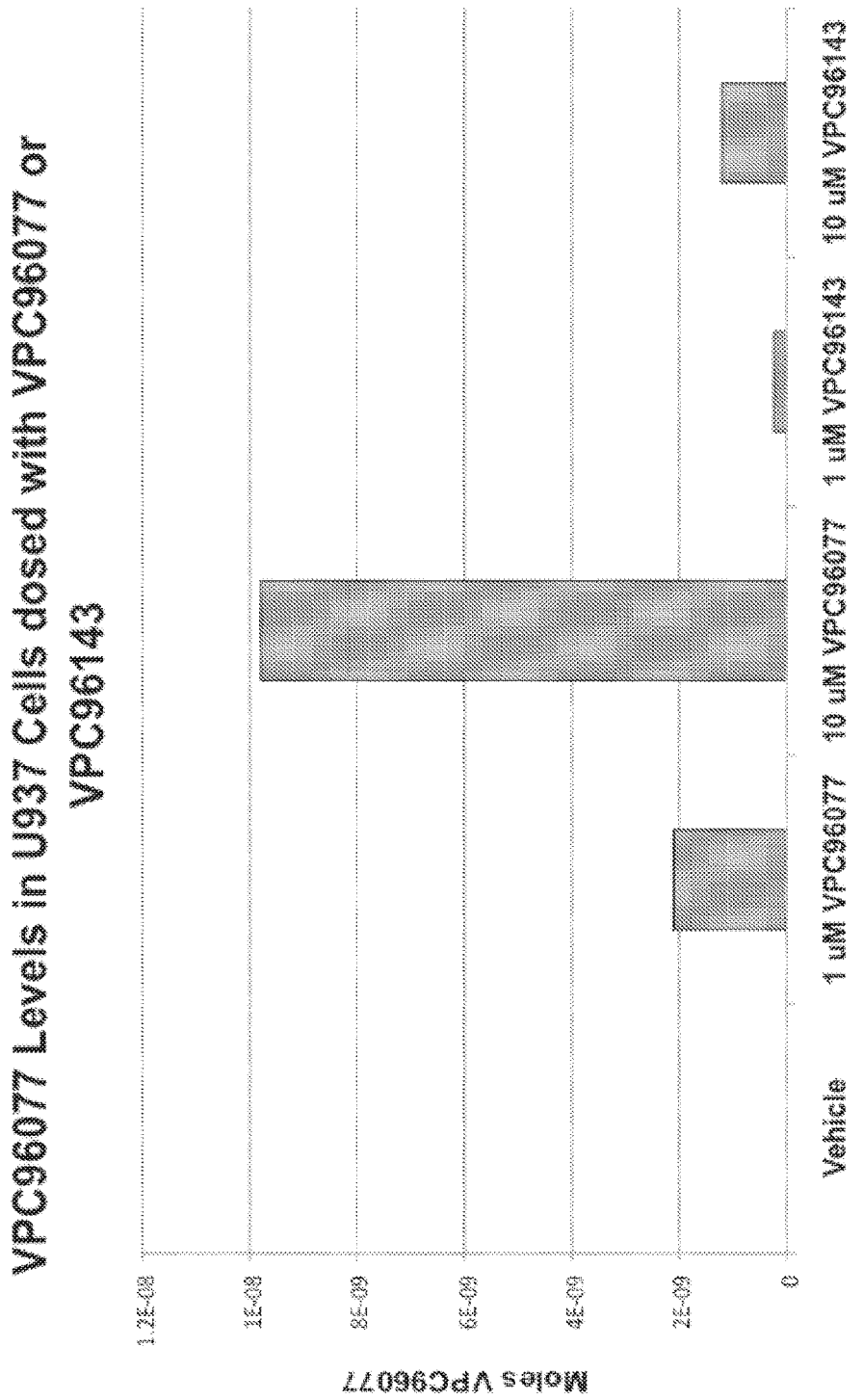

U937 cells (5 million) were treated with amidoxime, VPC96143, at concentrations of 1 μM or 10 μM, and amidine, VPC96077, at concentrations of 1 μM or 10 μM. The accumulation of S1P was measured 2 hrs post-dose. Also, the levels of amidine, VPC96077, were measured 2 hrs post-dose. The results are illustrated in FIGS. 9A-9B.

The accumulation of S1P and amidine and the drug to pro-drug ratio in organs, demonstrates the efficiency of conversion of amidoxime to amidine in target organs indicating that amidoximes are pro-drug forms of amidines.

The invention should not be construed to be, limited solely to the assays and methods described above, but should be construed to include other methods and assays as well. Other methods that are used but not described above are well known and within the competence of one of ordinary skill in the art of chemistry, biochemistry, molecular biology, and clinical medicine. One of ordinary skill in the art will know that other assays and methods are available to perform the procedures described above.

The abbreviations used above have their conventional meaning within the clinical, chemical, and biological arts. In the case of any inconsistencies, the present disclosure, including any definitions therein will prevail.

The invention claimed is:

1. A method for treatment of a disease selected from a neoplastic disease, an autoimmune disease, or asthma in a mammal suffering therefrom, comprising administering to said mammal an effective amount of a compound of formula IA:

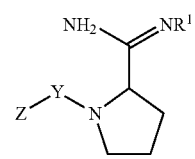

wherein
R$^1$ is hydrogen or OH;
Y is C=O (carbonyl);
Z is
A. (C$_{12}$-C$_{20}$)alkylaryl, wherein Z is optionally substituted with a (C$_6$-C$_{10}$)alkoxycycloalkyl, (C$_6$-C$_{10}$)alkoxyphenyl, phenyl, or a (C$_3$-C$_7$)cycloalkyl;
B. (C$_5$-C$_{12}$)alkyl-4-phenyl substituted with (C$_5$-C$_{10}$)cycloalkyl-O; or
C. a substituent selected from the group consisting of

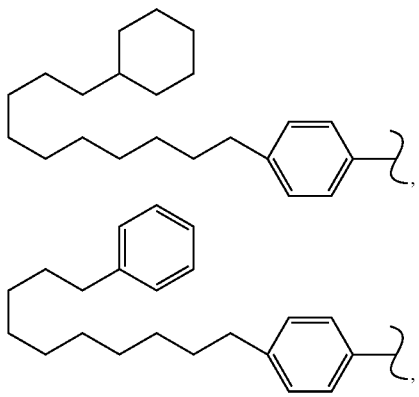

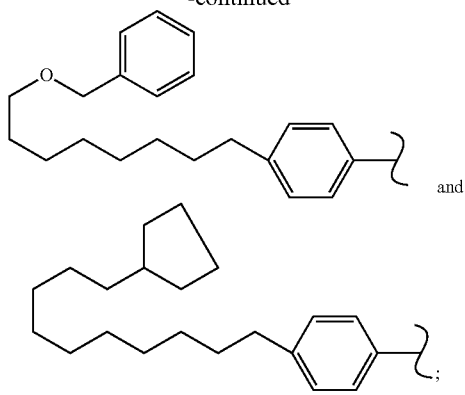
or a pharmaceutically acceptable salt or ester thereof.
2. The method of claim 1, wherein the disease is asthma or an autoimmune disease.
3. The method of claim 2, wherein the autoimmune disease is rheumatoid arthritis.
4. The method of claim 1, wherein the disease is asthma.
5. The method according to claim 1, wherein the compound is selected from the group consisting of:
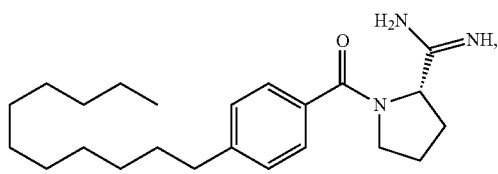
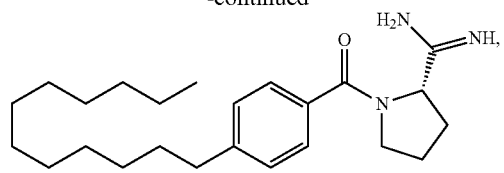
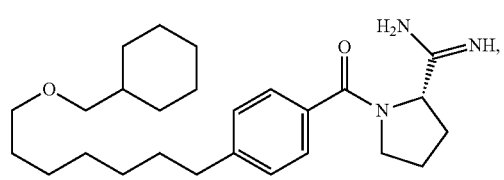
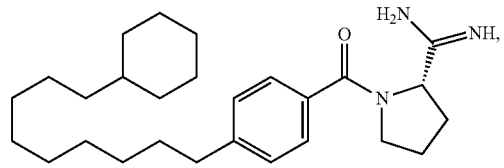
* * * * *